US010925962B2

(12) United States Patent
Saito et al.

(10) Patent No.: US 10,925,962 B2
(45) Date of Patent: Feb. 23, 2021

(54) POLYMERIC IGA-TYPE RECOMBINANT ANTIBODY AND USE THEREOF

(71) Applicants: Japan as represented by Director General of National Institute of Infectious Diseases, Tokyo (JP); Nippi, Incorporated, Tokyo (JP)

(72) Inventors: Shinji Saito, Tokyo (JP); Tadaki Suzuki, Tokyo (JP); Hideki Hasegawa, Tokyo (JP); Akira Ainai, Tokyo (JP); Kiyoko Goto, Tokyo (JP); Tomonori Ueno, Kashiwa (JP); Yuki Taga, Tokyo (JP)

(73) Assignee: Nippi, Incorporated, Tokyo (JP)

( * ) Notice: Subject to any disclaimer, the term of this patent is extended or adjusted under 35 U.S.C. 154(b) by 448 days.

(21) Appl. No.: 15/326,569

(22) PCT Filed: Jul. 21, 2015

(86) PCT No.: PCT/JP2015/070742
§ 371 (c)(1),
(2) Date: Feb. 24, 2017

(87) PCT Pub. No.: WO2016/010161
PCT Pub. Date: Jan. 21, 2016

(65) Prior Publication Data
US 2017/0340732 A1 Nov. 30, 2017

(30) Foreign Application Priority Data

Jul. 18, 2014 (JP) .............................. JP2014-148328

(51) Int. Cl.
| | | |
|---|---|---|
| *A61K 39/395* | (2006.01) | |
| *C07K 16/18* | (2006.01) | |
| *C12N 15/09* | (2006.01) | |
| *C07K 16/06* | (2006.01) | |
| *C12N 15/01* | (2006.01) | |
| *C12N 15/10* | (2006.01) | |
| *C12N 15/66* | (2006.01) | |
| *C07K 16/10* | (2006.01) | |
| *A61K 39/00* | (2006.01) | |

(52) U.S. Cl.
CPC .......... *A61K 39/395* (2013.01); *C07K 16/065* (2013.01); *C07K 16/18* (2013.01); *C12N 15/01* (2013.01); *C12N 15/09* (2013.01); *C12N 15/1086* (2013.01); *C12N 15/66* (2013.01); *A61K 2039/505* (2013.01); *A61K 2039/507* (2013.01); *C07K 16/10* (2013.01)

(58) Field of Classification Search
None
See application file for complete search history.

(56) References Cited

U.S. PATENT DOCUMENTS

| | | | | |
|---|---|---|---|---|
| 5,534,411 A | * | 7/1996 | Weltzin | .................. A61P 31/12 |
| | | | | 435/7.2 |
| 6,673,342 B1 | * | 1/2004 | Capra | .................... C07K 16/00 |
| | | | | 424/130.1 |
| 9,573,996 B2 | * | 2/2017 | Ariaans | ................ A61K 9/0053 |

FOREIGN PATENT DOCUMENTS

| | | |
|---|---|---|
| WO | 2013087914 A1 | 6/2013 |
| WO | 2014157429 A1 | 10/2014 |

OTHER PUBLICATIONS

Li et al., Sheng Wu Gong Cheng Xue Bao. Feb. 2011;27(2):219-25., abstract only.*
Johansen et al., Eur J Immunol. May 1999;29(5):1701-8.*
Stryer, L. Biochemistry, 4th edition, W.H. Freeman and Company, 1995, pp. 18-23.*
Li et al., J Immunol Res. 2014;2014:394127. doi: 10.1155/2014/394127. Epub Feb. 13, 2014.*
Virdi et al., Cell Mol Life Sci. Feb. 2016;73(3):535-45. doi: 10.1007/s00018-015-2074-0. Epub Oct. 28, 2015.*
Song et al., J Immunol. Jul. 15, 1995;155(2):715-21.*
Graham et al., Curr Opin HIV AIDS. Author manuscript; available in PMC May 1, 2016. Published in final edited form as: Curr Opin HIV AIDS. May 2015; 10(3): 129-134. doi: 10.1097/COH.0000000000000154.*
Vaerman J P et al: "Homogenous IgA monomers, dimers, trimers, and tetramers from the same IgA myeloma serum," Immunological Investigations, Informa Healthcare, US, vol. 24, No. 4, Jan. 1, 1995, pp. 631-641, XP009501644, ISSN: 0882-0139, DOI: 10.3109/08820139509066863.
Brian Moldt et al: "Simplifying the Synthesis of SIgA: Combication of dIgA and rhSC using affinity chromatography", Methods, vol. 65, No. 1, Jan. 1, 2014, pp. 127-132.
Stubbe H et al: "Polymeric IgA is superior to monomeric IgA and IgG carrying the same variable domain in preventing Clostridium difficile toxin A damaging of T84 monolayers", The Journal of Immunology, vol. 164, No. 4, Feb. 2000, pp. 1952-1960.
European Patent Office, Office Action issued in EP 15822054.1 dated Apr. 11, 2019, 6 pages.
Woof, J.M. and Russell, M.W., Structure and function relationships in IgA, Mucosal immunology, 4(6), 590-597, 2011.
Li, C.et al., Construction of a Chimeric Secretory IgA and Its Neutralization Activity against Avian Influenza Virus H5N1, Journal of Immunology Research, Feb. 13, 2014, vol. 2014, Article ID 394127, pp. 1-10.

(Continued)

*Primary Examiner* — Michael Szperka
(74) *Attorney, Agent, or Firm* — Wood Herron & Evans LLP

(57) ABSTRACT

Provided are: a polymeric IgA-type recombinant antibody; a medicine containing this polymeric IgA-type recombinant antibody as an active ingredient; a method for producing this polymeric IgA type antibody, the method including the step of coexpressing an IgA-type antibody heavy-chain protein, an antibody light-chain protein, an antibody J-chain protein, and a secretory component protein within a single cell; and a method for improving the antigen-binding activity or neutralizing activity of this antibody, the method including the step of making an antibody into a polymeric IgA-type.

13 Claims, 20 Drawing Sheets

Specification includes a Sequence Listing.

(56) References Cited

OTHER PUBLICATIONS

Johansen, F.E. et al., Recombinant expression of polymeric IgA: incorporation of J chain and secretory component of human origin, European Journal of Immunology, 1999, 29(5), pp. 1701-1708.
Muramatsu, M. et al., Comparison of Antiviral Activity between IgA and IgG Specific to Influenza Virus Hemagglutinin: Increased Potential of IgA for Heterosubtypic Immunity, PLOS One, Jan. 17, 2014, vol. 9, Issue 1, e85582.
Lorin, V. and Mouquet, H., Efficient generation of human IgA monoclonal antibodies, Journal of Immunological Methods, Apr. 22, 2015, 422, pp. 102-110.
Japanese Patent Office, Search Report in International Patent Appilcation No. PCT/JP2015/070742 dated Oct. 20, 2015.
Lullau E et al: "Antigen Binding Properties of Purified Immunoglobulin A and Reconstituted Secretory Immunoglobulin A Antibodies" Journal of Biological Chemistry, American Society for Biochemistry and Molecular Biology, vol. 271, No. 27, Jul. 5, 1996, pp. 16300-16309, XP002028581, ISSN: 0021-9258, DOI: 10.1074/JBC.271.27.16300.
Aoyama K et al: "Separation of different molecular forms of mouse IgA and IgM monoclonal antibodies by high-performance liquid chromatography on spherical hydroxyapatite beads," Journal of Immunological Methods, Elsevier Science Publishers B.V., Amsterdam, NL, vol. 162, No. 2, Jun. 18, 1993, pp. 201-210, XP023974805, ISSN: 0022-1759, DOI: 10.1016/0022-1759(93)90385-K.
Vaerman J P et al: "Homogenous IgA monomers, dimers, trimers, and tetramers from the same IgA myeloma serum," Immunological Investigations, Informa Healthcare, US, vol. 24, No. 4, Jan. 1, 1995, pp. 631-641, XP009501644, ISSN: 0882-0139, DOI: 10.1371/journal.pbio.1001336.
Xianying A. Cui et al: "pI80 Promotes the Ribosome-Independent Localization of a Subset of mRNA to the Endoplasmic Reticulum," PLOS Biology, vol. 10, No. 5, May 29, 2012, p. e1001336, XP55291786, DOI: 10.1371/journal.pbio.1001336.
Sorensen Vigdis et al: "Structural requirements for incorporation of J chain into human IgM and IgA," International Immunology, Oxford University Press: vol. 12, No. 1, Jan. 1, 2000, pp. 19-27, XP002430237, ISSN: 0953-8178, DOI: 10.1093/INTIMM/12.1.19.
S. Longet et al: "Human Plasma-derived Polymeric IgA and IgM Antibodies Associate with Secretory Component to Yield Biologically Active Secretory-like Antibodies," Journal of Biological Chemistry, vol. 288, No. 6, Dec. 18, 2012, pp. 4085-4094, XP55354168, ISSN: 0021-9258, DOI: 10.1074/jbc.M112.410811.
Michetti P et al: "Production and use of momclonal IgA antibodies complexed with recombinant secretory component for passive mucosal protection," Advances in Experimental Medicine and Biology: Springer, US, vol. 310, Jan. 1, 1991, pp. 183-185, XP002081162, ISSN: 0065-2598.
European Patent Office, Seach Report issued in European Patent Application No. 15822054.1 dated Dec. 1, 2017, 11 pages.
Zhang, B-Z et al., "Cloning of Genes by Genomic DNA Splicing for Secretory IgA Production," China Biotechnology (2008) 28(6):1-6.

* cited by examiner

POLYMERIC IGA-TYPE RECOMBINANT ANTIBODY AND USE THEREOF

TECHNICAL FIELD

The present invention relates to a polymeric IgA-type recombinant antibody and use thereof. Priority is claimed on Japanese Patent Application No. 2014-148328, filed on Jul. 18, 2014, the content of which is incorporated herein by reference.

BACKGROUND ART

The best features of antibodies are high levels of antigen-binding activity and specificity in which the antibodies strongly bind only to target antigens and do not bind to others. Antibodies have functional activities such as neutralizing activity and the like due to a combination of the antigen-binding activity and specificity, and thus have been widely used in the fields of bio-industry including therapeutic antibodies, diagnostic drugs, biological research tools, etc.

In recent years, since systems of producing large amounts of chimeric antibodies, humanized antibodies, and human antibodies have been established, therapeutic antibodies have become one major type of medicines. However, most monoclonal antibodies have an IgG type, and only the IgG type has been put to practical use especially for therapeutic antibodies.

In addition to IgG, there are isotypes such as IgM, IgA, IgD, IgE, and the like in the case of antibodies, and each has different in vivo functions. For example, IgG is the main antibody present in vivo in blood, but the main antibody in mucus or secretory fluid covering the mucous epithelium is IgA, which is in turn known to serve as a front-line in a biological defense mechanism against mucosal infections (for example, see Non-patent Literature 1).

Also, some antibodies such as IgA and IgM are known to function in vivo by forming polymers such as dimers and pentamers with antibodies having the same variable region. For example, polymeric IgA is known to be present in secretory fluids such as colostrum and saliva, and sera from patients with multiple myeloma.

Monomeric, dimeric, trimeric and tetrameric IgA are found to be included at various ratios in sera from patients with multiple myeloma. Also, the dimers and tetramers are reported to be included in secretory fluids. However, little is known about the biological significance of this polymeric antibody.

Also, technology of artificially producing dimeric IgA has already been reported, but the yield of the dimeric IgA is poor, and there is no example in which high functionality is achieved by converting IgG into an IgA type. Also, technology of artificially producing polymeric IgA such as trimeric or more IgA is not known.

CITATION LIST

Non-Patent Literature

[Non-Patent Literature 1]
Woof J. M. and Russell M. W., Structure and function relationships in IgA, Mucosal immunology, 4(6), 590-597, 2011

SUMMARY OF INVENTION

Technical Problem

So far, no technology of artificially making any monomeric antibody into a polymeric type is known. Also, there is no example in which an IgA-type antibody is produced on an industrial scale and applied industrially. Therefore, an object of the present invention is to provide a polymeric IgA-type recombinant antibody. Another object of the present invention is to provide a medicine containing the polymeric IgA-type recombinant antibody as an active ingredient. Still another object of the present invention is to provide a method of producing a polymeric IgA-type antibody. Yet another object of the present invention is to provide a method of improving antigen-binding activity of the antibody.

Solution to Problem

The present invention provides the following.
(1) A polymeric IgA-type recombinant antibody.
(2) The polymeric IgA-type recombinant antibody defined in (1), wherein an amino acid residue at position 458 of a heavy chain constant region is an amino acid residue derived from hydrophobic amino acids.
(3) The polymeric IgA-type recombinant antibody defined in (1) or (2), wherein a content of a tetramer is greater than or equal to 20 mol % of the total IgA.
(4) A medicine containing the polymeric IgA-type recombinant antibody defined in any one of (1) to (3) as an active ingredient.
(5) The medicine defined in (4), which is used for treatment or prevention of infections.
(6) A method of producing a polymeric IgA-type antibody, the method including the step of coexpressing an IgA-type antibody heavy-chain protein, an antibody light-chain protein, an antibody J-chain protein, and a secretory component protein in a single cell.
(7) The method defined in (6), wherein the IgA-type antibody heavy-chain protein is converted/modified from an IgG type to an IgA type by means of genetic recombination.
(8) The method defined in (6) or (7), wherein a p180 protein and an SF3b4 protein are further coexpressed in the single cell in the step.
(9) The method defined in any one of (6) to (8), wherein the single cell is a CHO
YA7 cell line (accession number: NITE BP-01535).
(10) The method defined in any one of (6) to (9), wherein the step is carried out by transfecting an expression vector for expressing an IgA-type antibody heavy-chain protein, an antibody light-chain protein, an antibody J-chain protein, and a secretory component protein into the single cell, and the expression vector has a cis-element, which an RNA-binding protein recognizes, binds to or interacts with, downstream from a promoter and also upstream from an initiation codon of nucleic acids coding for the IgA-type antibody heavy-chain protein, the antibody light-chain protein, the antibody J-chain protein, or the secretory component protein.
(11) The method defined in (10), wherein the cis-element includes one to several base sequences consisting of a sequence motif $GAN_1\text{-}(X)_n\text{-}ACN_2$ (where n is an integer ranging from 3 to 6, and $N_1$ and $N_2$ are each independently any one selected from A, T, G, and C.).

(12) The method defined in (10) or (11), wherein the cis-element consists of:

a base sequence set forth in any one selected from SEQ ID NOs: 21 to 23, a base sequence in which one to several bases are deleted, substituted or added in the base sequence set forth in any one selected from SEQ ID NOs: 21 to 23, and which the RNA-binding protein recognizes, binds to or interacts with, a base sequence having an identity of 80% or more to the base sequence set forth in any one selected from SEQ ID NOs: 21 to 23, and which the RNA-binding protein recognizes, binds to or interacts with, or a base sequence hybridizable under a stringent condition with nucleic acids having a base sequence complementary to nucleic acids having the base sequence set forth in any one selected from SEQ ID NOs: 21 to 23, and also which the RNA-binding protein recognizes, binds to or interacts with.

(13) A method of improving the antigen-binding activity or neutralizing activity of the antibody, the method including the step of making an antibody into a polymeric IgA type.

(14) The method defined in (13), wherein the antibody is an IgG-type antibody.

(15) The method defined in (13) or (14), wherein the step comprises the step of:

coexpressing an IgA-type antibody heavy-chain protein having a heavy-chain variable region of the antibody, a light-chain protein of the antibody, an antibody J-chain protein, and a secretory component protein in a single cell.

Advantageous Effects of Invention

According to the present invention, a polymeric IgA-type recombinant antibody can be provided. Also, a medicine containing the polymeric IgA-type recombinant antibody as an active ingredient can be provided. In addition, a method of producing a polymeric IgA-type antibody can be provided. Further, a method of improving the antigen-binding activity of the antibody can be provided.

DESCRIPTION OF EMBODIMENTS

Description of Terms

Figure 1:
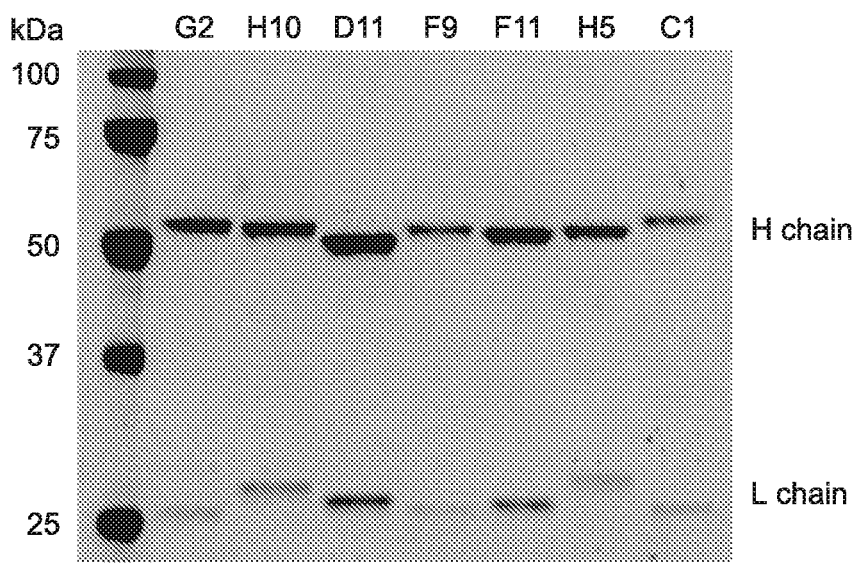
FIG. 1 is an image showing results of running respective clones of an expressed and purified recombinant monoclonal IgG1 antibody on sodium dodecyl sulfate (SDS) polyacrylamide gel electrophoresis (SDS-PAGE) to stain the recombinant monoclonal IgG1 antibody with Simply Blue (trademark) Safe Stain.

In the context of IgA-type antibodies, the terms used in the related art will be described below.

(Monomeric IgA (mIgA))

In serum, IgA is mainly present as a monomeric IgA that has a molecular weight of approximately 170,000, and IgA1 is a main component.

(Dimeric IgA (dIgA))

A dimeric IgA is a dimeric IgA that is produced by plasma cells present in the mucosal lamina propria, and represents a molecule in which a heavy chain, a light chain and a J chain are present at a ratio of 4:4:1. In the dimeric IgA, IgA2 accounts for approximately half.

(Polymeric IgA (pIgA))

Conventionally, dimeric or higher IgA recognized by a polymeric Ig receptor is often generally referred to as a polymeric IgA. That is, as a complex in which a heavy chain, a light chain and a J chain are present at a composition ratio of 4:4:1, a dimeric IgA in which two IgA molecules are associated via an antibody J-chain protein (a joining chain) is a main ingredient, and the term "polymeric IgA" is used both when it includes a secretory component protein (SC protein) and when it does not include an SC protein.

That is, cases in which a polymeric IgA (a complex in which a heavy chain, a light chain and a J chain are present at a composition ratio of 4:4:1) secreted by plasma cells is referred to as a "polymeric IgA," cases in which a S-IgA (a complex in which a heavy chain, a light chain, a J chain and SC are present at a composition ratio of 4:4:1:1) secreted by mucosal epithelial cells is referred to as a "polymeric IgA," and cases in which it could refer to either are occasionally found, and thus these cases are not strictly distinguished. A component having a higher molecular weight than the dimeric IgA is detected based on the mobility in electrophoresis and the behaviors in gel filtration chromatography, and is often referred to as a polymeric IgA since the component is expected to be dimeric or higher. However, since the component is not distinguished from aggregates, a specific molecular structure of the component is not known.

(Polymeric Immunoglobulin Receptor (Polymeric Ig Receptor (pIgR)))

pIgR expressed on cell membranes in the basal side of mucosal epithelial cells is a type I transmembrane protein that belongs to an immunoglobulin superfamily, and is composed of an extracellular domain region, a transmembrane region, and an intracytoplasmic region. pIgR specifically recognizes and binds to a dimeric/polymeric Ig molecule including a J chain, which are produced by plasma cells existing in the mucosal lamina propria, and is transferred to an apical side in a state in which the pIgR is bound to the dimeric/polymeric Ig molecule after incorporation into epithelial cells. A cleavage between the extracellular domain region and the transmembrane region of the pIgR is needed to release the dimeric/polymeric Ig molecule from epithelial cells into a surface of the mucosa, and the dimeric/polymeric Ig molecule is secreted as S-IgA into the lumenal mucosal layer after the cleavage by a proteolytic enzyme in the epithelial cells. Based on the fact that the extracellular domain region of pIgR becomes a component of the IgA complex, this domain of pIgR is referred to as a secretory component protein (SC protein). The pIgR plays the same role in introduction of a pentameric IgM.

The SC protein is a highly glycosylated polypeptide that corresponds to an extracellular domain region of pIgR and having a molecular weight of approximately 70 kDa. The SC protein has five immunoglobulin-like domains from the N-terminus thereof, which are sequentially named D1 to D5. Among these, D1 to D3 are required to bind to the dimeric IgA. In particular, D1 has a structure similar to complementarity-determining regions (CDRs) of variable regions of immunoglobulins, and thus plays an important role in binding to the dimeric IgA. Thr27-Thr33 in CDR1 of D1 is involved in this interaction. Also, Glu53-Gly54 in a CDR2 loop of D1 is also reported to be involved in the interaction. The J chain is a polypeptide chain having a molecular weight of 15 kDa, has an N-linked sugar chain, and is folded to form an immunoglobulin structure. When comparing J chains of mammals and birds, the J chains have very high homology in terms of the primary structure and are cross-reactively detected as antigen with species-specific antibody, and thus the basic characteristics of the J chains are considered to be conserved among organisms. The J chain is essential for the dimeric IgA to interact with pIgR. It is thought that a dimeric IgA in which the J chain is introduced combines with SC due to the interaction between D1 of pIgR and an Fc region of IgA or between pIgR and the J chain, followed by the formation of S—S bond between a $311^{th}$ Cys residue of an IgAC α2 domain and a $467^{th}$ Cys residue of D5 of SC. (Mucosal immunology, 4(6), 590-597, 2011, Hiroshi Kiyono (2010). Clinical Mucosal Immunology, Synergy International, Inc.)

(Secretory IgA (S-IgA))

S-IgA refers to a dimeric or higher IgA complex that is secreted by mucosal epithelial cells and includes an SC protein. In the case of the secretory dimeric IgA (S-dIgA), a heavy chain, a light chain, a J chain and SC are present at a composition ratio of 4:4:1:1.

(Difference Between Polymeric IgA and Secretory Polymeric IgA)

Since it is technically difficult to analyze the characteristics, such as a molecular weight, of the polymeric IgA produced by plasma cells present in the mucosal lamina propria, a detailed molecular formation process of forming a secretory polymeric IgA is unknown.

That is, it is unclear that which of dimer, trimer, tetramer, and the like is the major secretory polymeric IgA produced by the plasma cells in vivo, whether polymerization occurs in epithelial cells, and which type plays a critical role in biological defense in mucosal tissues. A trace of IgA having a higher molecular weight than a dimer (approximately 440 kDa) is detected, but is not distinguished from aggregates.

(Definition of Polymeric IgA in this Specification)

In this specification, a polymeric antibody having a secretory component (SC) protein in a molecule thereof is referred to as a secretory antibody. Also, the polymeric antibody is often indicated as follows.

Monomeric antibody=mIgA
Dimeric antibody=dIgA
Secretory dimeric antibody=S-dIgA
Secretory trimeric antibody=S-tIgA
Secretory tetrameric antibody=S-qIgA
Tetrameric or higher secretory polymeric antibody=S-pIgA
Recombinant monomeric antibody=rmIgA
Recombinant dimeric antibody=rdIgA
Recombinant secretory dimeric antibody=recombinant S-dIgA (rS-dIgA)
Recombinant secretory trimeric antibody=recombinant S-tIgA (rS-tIgA)
Recombinant secretory tetrameric antibody=recombinant S-qIgA (rS-qIgA)

Tetrameric or higher recombinant secretory polymeric antibody=recombinant S-pIgA (rS-pIgA)

Here, when an antibody has a secretory component (SC) protein in a molecule thereof, "S-" is attached to the molecular name. An antibody having no SC in a molecule thereof is not marked with "S-." Also, an association state of a molecule is indicated by abbreviating the molecule before IgA. A monomer is marked with "m," a dimer is marked with "d," a trimer is marked with "t," a tetramer is marked with "q," and a tetramer or higher polymer is marked with "p." Also, a monomeric antibody and a recombinant monomeric antibody may be referred to as a "monomer" without particular distinction. In addition, a dimeric antibody, a secretory dimeric antibody, a recombinant dimeric antibody, and a recombinant secretory dimeric antibody may be referred to as a "dimer" without particular distinction. Additionally, a secretory trimeric antibody and a recombinant secretory trimeric antibody may be referred to as a "trimer" without particular distinction. Also, a secretory tetrameric antibody and a recombinant secretory tetrameric antibody may be referred to as a "tetramer" without particular distinction. Further, a tetrameric or higher secretory antibody and a tetrameric or higher recombinant secretory polymeric antibody may be referred to as a "polymer" without particular distinction.

[Polymeric IgA-Type Recombinant Antibody]

According to one embodiment, the present invention provides a polymeric IgA-type recombinant antibody. The polymeric IgA-type recombinant antibody according to this embodiment may further include polymerized recombinant IgA antibody converted from originally a non-IgA type by means of genetic recombination.

Non-IgA-type antibodies may, for example, include non-IgA-type antibodies such as human antibodies, non-human mammal-derived antibodies, rodent-derived antibodies, bird-derived antibodies, and the like, but the present invention is not limited thereto. Also, a class of antibodies is not particularly limited, and may, for example, include IgG-type, IgM-type, IgE-type, IgD-type, IgY-type antibodies, etc.

For example, an IgG-type antibody may be converted into an IgA type by transplanting a variable region of an IgG-type antibody into a backbone framework of an IgA-type antibody. Alternatively, the IgG-type antibody may be converted into an IgA type by transplanting only a CDR region of the IgG-type antibody into a CDR region of the IgA-type antibody. A subclass of IgA may be either an IgA1 type or an IgA2 type.

Also, in immunoglobulin molecules, it is known that there are allotypes with genetically distinct antigenicity found among individuals within the same species. In many cases, the allotypes are often caused by mutation of one to several amino acids in a constant region of the immunoglobulin molecule.

In general, two allotypes (IgA2m(1) and IgA2m(2)) are found in human IgA2, and it is reported that there is a third allotype called IgA2(n). In this specification, IgA2 may be any one of the allotypes.

The polymeric IgA-type recombinant antibody according to this embodiment preferably includes a secretory component (SC) protein in a molecule thereof. Also, the polymeric IgA-type recombinant antibody is preferably a dimer or higher, more preferably a trimer or higher, and further preferably a tetramer or higher.

As will be described later, the present inventors have first succeeded in efficiently producing a polymeric IgA-type recombinant antibody. With the antibody according to this embodiment, the IgA-type recombinant antibody is industrially applicable.

In the polymeric IgA-type recombinant antibody according to this embodiment, an amino acid residue at position 458 of a constant region of a heavy chain is preferably an amino acid residue derived from hydrophobic amino acids.

As will be described later in examples, the present inventors have found that a ratio of trimeric/tetrameric antibodies may be significantly increased when the amino acid residue at position 458 of the heavy chain constant region is the amino acid residue derived from hydrophobic amino acids.

The hydrophobic amino acids may include isoleucine (I), leucine (L), methionine (M), tryptophan (W), and glycine (G). Among these, isoleucine is preferred because isoleucine has high activity to further increase a ratio of trimeric/tetrameric antibodies.

The polymeric IgA-type recombinant antibody according to this embodiment may be a mixture of dimeric, trimeric and tetrameric antibodies. Also, a monomer may be mixed. The polymeric IgA-type recombinant antibody according to this embodiment includes a tetramer at a content of 20 mol % or more of the total IgA. The content of the tetramer is preferably greater than or equal to 30 mol %, more preferably greater than or equal to 40 mol %, further preferably greater than or equal to 50 mol %, and particularly preferably greater than or equal to 60 mol % of the total IgA.

The ratio of monomeric, dimeric, trimeric/tetrameric antibodies in the polymeric IgA-type recombinant antibody may, for example, be measured by size exclusion chromatography, as will be described later in examples. Peaks of the trimer and tetramer may not be separated in some cases upon measurement by the size exclusion chromatography, as will be described later in examples. In this case, the polymeric IgA-type recombinant antibody according to this embodiment preferably includes the trimer/tetramer (trimer or tetramer) at a content of 20 mol % or more, more preferably 30 mol % or more, further preferably 40 mol % or more, particularly preferably 50 mol % or more, and most preferably 60 mol % or more of the total IgA.

As will be described later in examples, the dimeric IgA has a molecular weight of 300 to 400 kDa. Also, the trimeric IgA has a molecular weight of 500 to 600 kDa. In addition, the tetrameric IgA has a molecular weight of 700 to 800 kDa. The molecular weights of IgA may be measured by mass spectrometry and the like under mild iontophoresis conditions which are, for example, achieved by lowering a degree of vacuum in the vicinity of an iontophoresis port, as will be described later in examples.

In the polymeric IgA-type recombinant antibody according to this embodiment, the antibody may be a chimera of an IgA-type antibody and a non-IgA-type antibody. In this specification, the IgA-type antibody refers to an antibody having an amino acid sequence which is at least partially derived from an IgA-type antibody. That is, the IgA-type antibody may also be a protein with which a typical anti-IgA polyclonal antibody reacts.

As will be described later in examples, the present inventors have found that the polymeric antibodies have higher antigen-binding activity or neutralizing activity against antigens than the monomeric antibodies.

According to one embodiment, the present invention provides a method of quantifying components of a polymeric IgA-type antibody, which includes the step of performing mass spectrometry using each of peptides having an amino acid sequence set forth in SEQ ID NOs: 70 to 97 as an internal standard. Also, when a stable isotope-labeled IgA antibody is produced by adding stable isotope-labeled amino acids into IgA antibody-secreting cells and culturing the IgA antibody-secreting cells using the method disclosed in Taga Y., et al., Stable isotope-labeled collagen: a novel and versatile tool for quantitative collagen analyses using mass spectrometry, J. Proteome Res. 13 (8), 3671-3678, 2014, the stable isotope-labeled IgA antibody may be used as an internal standard. The polymeric IgA-type antibody is preferably derived from a human being. Also, the components may include an IgA1 antibody heavy chain, an IgA2 antibody heavy chain, a λ-type antibody light chain, a κ-type antibody light chain, a J chain, and an SC.

According to one embodiment, the present invention provides standards for quantifying components of the polymeric IgA-type antibody, which includes a set of peptides having amino acid sequences set forth in SEQ ID NOs: 70 to 97.

[Medicines]

According to one embodiment, the present invention provides a medicine containing the polymeric IgA-type recombinant antibody as an active ingredient. The medicine according to this embodiment is preferably used for treatment or prevention of infections. The infections may include infections caused by pathogens such as parasites, bacteria, fungi, viruses, abnormal prions, etc.

A main antibody in mucus or secretory fluid covering the mucous epithelium is IgA, but IgA is not practically used as an antibody medicine although the IgA is known to serve as a front-line in a biological defense mechanism against mucosal infections.

The present inventors have conducted research to develop a intranasal vaccine using a whole inactivated influenza virus vaccine as a next-generation influenza vaccine, characterized by safe and simple inoculation of an inactivated whole virion of influenza virus as vaccine antigen. So far, in addition to basic research using animals, clinical research with recruited healthy adult volunteers shows good results, and the research is entering a clinical development stage for the purpose of practical application.

In this process, the present inventors have found that among IgA antibodies, which are considered to play an important role in protection against viral infections in respiratory mucosa of subjects who received a nasal inactivated influenza vaccine, polymeric antibodies larger than dimers are present and have a higher influenza virus-neutralizing activity than monomeric and dimeric antibodies.

Also, as will be described later in examples, the present inventors first succeeded in efficiently producing a polymeric IgA-type recombinant antibody, and have found that the polymeric IgA-type recombinant antibody has higher influenza virus-neutralizing activity and HA protein-binding activity than monomeric and dimeric antibodies.

Therefore, the medicine according to this embodiment is usefully used as a therapeutic or prophylactic agent against mucosal infections such as influenza, RS virus infection, severe acute respiratory syndrome (SARS), Middle Eastern respiratory syndrome (MERS), acquired immune deficiency syndrome (AIDS), etc.

Also, as will be described later, the polymeric IgA-type recombinant antibody may bind to and neutralize influenza virus, RS virus, etc. even when used in a small amount.

Therefore, the medicine according to this embodiment could be an antibody medicine for respiratory administration that may be applied as a prophylactic or therapeutic agent against the infections, an in vitro diagnostic agent, an antibody for research use, etc.

For a prophylactic purpose, the medicine according to this embodiment may be administered to a subject at high risk of being infected by viruses causing the infections. Alternatively, the medicine may be administered to a patient whose morbidity in the infections is identified for a therapeutic purpose and the purpose of preventing the virus from spreading.

The medicine according to this embodiment may be administered after the medicine is prepared into formulations such as powders, liquids, etc. For the purpose of enhancing the retention of a sprayed antibody, for example, a nasal excipient usually contained in nasal sprays for allergic rhinitis already available on the market may be added to the medicine according to this embodiment.

The medicine according to this embodiment may be administered by spraying it onto the nasal mucosa, administered by inhalation into the lower respiratory tract using a nebulizer, etc.

The administration by spraying onto the nasal mucosa may, for example, be performed in the same manner as for the nasal whole particle-inactivated influenza vaccine as disclosed in Ainai A, et al., Intranasal vaccination with an inactivated whole influenza virus vaccine induces strong antibody responses in serum and nasal mucus of healthy adults, Hum Vaccin Immunother. 9(9), 1962-1970, 2013.

When the therapeutic or prophylactic agent of this embodiment is administered by spraying it onto the nasal mucosa, for example, the therapeutic or prophylactic agent may be sprayed into both nostrils at an amount of 250 µL per nostril. Also, an amount of the administered antibody may be in a range of several hundred µg to several mg per inoculation (500 µL). For spraying, for example, a spray device used for nasal whole inactivated influenza virus vaccine may be used. Also, the therapeutic or prophylactic agent may be sprayed twice (morning and evening) to 4 times (once every 6 hours) a day. The administration period may, for example, be one week.

Also, when the medicine according to this embodiment is administered by inhalation into the lower respiratory tract, for example, a generally used aerosol-type inhaler may be used. An amount of the inhaled antibody may, for example, be several mg to several tens of mg per inhalation. Also, the antibody may be inhaled approximately twice a day (morning and evening). The administration period may, for example, be one week.

The medicine according to this embodiment may be administered to a human being, or, for example, a domestic animal such as a horse, a cow, a goat, a sheep, a pig, etc.; a pet such as a dog, a cat, etc.; a primate such as a chimpanzee, a gorilla, a cynomolgus monkey, etc.; a rodent such as a mouse, a rat, a guinea pig, etc.

In the medicine according to this embodiment, the IgA heavy chain, the IgA light chain, the J chain, the secretory component protein (hereinafter also referred to as "SC") preferably have amino acid sequences derived from a target animal (a target animal type). Here, the target animal type means that the constant regions of the IgA heavy chain and the IgA light chain coding for the polymeric antibody have amino acid sequences of constant regions of an IgA heavy chain and an IgA light chain of the target animal. Also, the animal type targeted by the J chain and the secretory component protein means that the J chain and the secretory component protein have amino acid sequences of a J chain and a secretory component protein of the target animal. The amino acid sequences of the IgA heavy chain, the IgA light chain, the J chain, and the secretory component protein may include mutations as long as the amino acid sequences have a desired antigen-binding activity.

[Method of Producing a Polymeric IgA-Type Antibody]

According to one embodiment, the present invention provides a method of producing a polymeric IgA-type antibody, which includes the step of coexpressing an IgA-type antibody heavy-chain protein, an antibody light-chain protein, an antibody J-chain protein, and a secretory component protein in a single cell. The polymeric IgA-type antibody may be a recombinant antibody.

As described above, pIgR expressed on cell membranes in the basal side of mucosal epithelial cells specifically recognizes and binds to a J chain protein in dimeric/polymeric Ig molecules produced by plasma cells present in the mucosal lamina propria, and incorporates dimeric/polymeric Ig molecules combind with the J chain protein into cells. Even after incorporation into epithelial cells, the pIgR is transferred to an apical side in a state in which the pIgR is bound to the dimeric/polymeric Ig molecule. In this case, a cleavage between an extracellular domain region and a transmembrane region of the pIgR occurs so that the pIgR is released from the inside of the epithelial cells into a surface of the mucosa.

That is, the IgA-type antibody heavy-chain protein, the antibody light-chain protein, the antibody J-chain protein, and the secretory component protein may not be coexpressed in vivo in a single cell.

In this regard, the present inventors have first succeeded in unexpectedly producing a polymeric IgA-type antibody by coexpressing a secretory component protein in a single cell together with an IgA-type antibody heavy-chain protein, an antibody light-chain protein, and an antibody J-chain protein. According to the production method of this embodiment, the polymeric IgA-type antibody is industrially applicable.

When the polymeric IgA-type antibody is administered to a subject as a medicine, the antibody J-chain protein and the secretory component protein preferably have amino acid sequences derived from an animal species as a target. Also, the antibody J-chain protein and the secretory component protein may be chimeras having amino acid sequences derived from a plurality of animal species.

According to this embodiment, the IgA-type antibody heavy-chain protein may be obtained by converting an originally non-IgA-type antibody into an IgA type by means of genetic recombination. The non-IgA-type antibody is not particularly limited, and may, for example, include a non-IgA-type human antibody, a non-human mammal-derived antibody, a rodent-derived antibody, a bird-derived antibody, etc. Also, a class of antibodies is not particularly limited, and may, for example, include IgG-type, IgM-type, IgE-type, IgD-type, IgY-type antibodies, etc.

For example, the IgG type antibody may be converted into an IgA type by transplantation of the variable region of the IgG type antibody into the backbone framework of the IgA-type antibody. Alternatively, the conversion from IgG type antibody to IgA type antibody could be performed by the graft of only CDR region of the IgG type antibody into the corresponding region of IgA type antibody. A subclass of IgA may be an IgA1 type or an IgA2 type.

Host cells may include mammalian cells, insect cells, etc. The mammalian cells may include 293F cells, CHO cells, CHO YA7 cells, etc., and the CHO YA7 cells are particularly preferred. The insect cells may include an Sf9 cell line, an Sf21 cell line, etc.

According to one embodiment, the present invention provides a method of producing a polymeric IgA-type antibody, which includes the step of coexpressing an IgA-type antibody heavy-chain protein, an antibody light-chain protein, an antibody J-chain protein, a secretory component protein, a p180 protein, and an SF3b4 protein in a single cell. The polymeric IgA-type antibody may be a recombinant antibody. An amino acid sequence of the p180 protein is set forth in SEQ ID NO: 98, and a base sequence coding for the p180 protein is set forth in SEQ ID NO: 99. Also, an amino acid sequence of the SF3b4 protein is set forth in SEQ ID NO: 100, and a base sequence coding for the SF3b4 protein is set forth in SEQ ID NO: 101.

Formation of polysomes on the endoplasmic reticulum membrane within the corresponding cell may be promoted by expressing the p180 protein and the SF3b4 protein in the cell. Here, the polysome refers to one molecule of mRNA bound to a plurality of ribosomes present on the endoplasmic reticulum membrane within the cell. As a result of promotion of the polysome formation, the protein synthesis ability may be enhanced, thereby improving production efficiency of a target protein. Suitable host cells are as described above. Also, the human p180 protein is a type I transmembrane protein present in the endoplasmic reticulum, and is composed of a short intracytoplasmic region, a transmembrane region, and a cytoplasmic domain region. From the analysis of the cDNA sequence which has already been identified, it is known that the cDNA sequence has a domain that is highly conserved among species in the vicinity of the N terminus of the cytoplasmic domain and shows very strong basicity (at positions 27 to 197 of SEQ ID NO: 98), followed by a basic repetitive sequence, and it is also known that there are at least three types of molecular species whose repeat numbers are 54, 26, and 14 (Ogawa-Goto K. et al., An endoplasmic reticulum protein, p180, is highly expressed in human cytomegalovirus-permissive cells and interacts with the tegument protein encoded by UL48, J. Virol., 76 (5), 2350-2362, 2002.). According to this embodiment, although a p180 protein having any repeat number may be used, a p180 protein having a repeat number of 54 is preferred. The C-terminal side of the p180 protein forms a coiled-coil domain, and, in the coiled-coil domain, a $945^{th}$ to $1,540^{th}$ region set forth in SEQ ID NO: 98 interacts with the SF3b4 protein to play an important role in promoting the polysome formation (Ueno T. et al., Regulation of polysome assembly on the endoplasmic reticulum by a coiled-coil protein, p180, Nucleic Acids Res., 40 (7), 3006-3017, 2012.).

Therefore, it is possible to efficiently produce the polymeric IgA-type antibody using the production method according to this embodiment.

An mRNA precursor transcribed from intracellular DNA is converted into mature mRNA by removing an intron moiety by splicing. This process is performed with a macrocomplex consisting of small nuclear RNA (snRNA) and proteins, which is referred to as a spliceosome. There are five types of small nuclear ribo-nucleoprotein complexes (snRNPs) in the spliceosome, and the SF3b4 protein is a constituent of U2-snRNP, and has an RNA-binding domain.

The present inventors have found that the SF3b4 protein predominantly increases in a membrane fraction containing endoplasmic reticulum in the cytoplasm, and the SF3b4 protein bound to mRNA also interacts with a coiled-coil domain of the p180 protein to promote localization of mRNA to the endoplasmic reticulum, resulting in enhanced abilities to synthesize or secrete proteins.

Therefore, when a nucleic acid coding for a target protein is expressed in cells in which expression of the p180 protein and the SF3b4 protein is enhanced, mRNA transcribed from the corresponding nucleic acid interacts with the SF3b4 protein or the p180 protein, or the mRNA interacts with the SF3b4 protein, and the SF3b4 protein then interacts with a coiled-coil domain of the p180 protein, thereby promoting the localization of the mRNA to the endoplasmic reticulum to enhance the abilities to synthesize or secrete the target protein in these cells.

According to this embodiment, the p180 protein may be a protein consisting of an amino acid sequence set forth in SEQ ID NO: 98, a protein consisting of an amino acid sequence having a sequence identity of 80% or more, preferably 85% or more, more preferably 90% or more, and particularly preferably 95% or more to the amino acid sequence set forth in SEQ ID NO: 98, and having a function of promoting formation of polysomes on the intracellular endoplasmic reticulum membrane, a protein consisting of an amino acid sequence having a sequence similarity of 80% or more, preferably 85% or more, more preferably 90% or more, and particularly preferably 95% or more to the amino acid sequence set forth in SEQ ID NO: 98, and having a function of promoting formation of polysomes on the intracellular endoplasmic reticulum membrane, a protein consisting of an amino acid sequence in which one to several amino acids are deleted, substituted or added in the amino acid sequence set forth in SEQ ID NO: 98, and having a function of promoting formation of polysomes on the intracellular endoplasmic reticulum membrane, a protein consisting of an amino acid sequence coded for by a base sequence having a sequence identity of 80% or more, preferably 85% or more, more preferably 90% or more, and particularly preferably 95% or more to a base sequence set forth in SEQ ID NO: 99, and having a function of promoting formation of polysomes on the intracellular endoplasmic reticulum membrane, or a protein consisting of an amino acid sequence coded for by a base sequence hybridizable under a stringent condition with nucleic acids consisting of a base sequence complementary to the base sequence set forth in SEQ ID NO: 99, and having a function of promoting formation of polysomes on the intracellular endoplasmic reticulum membrane. Also, the p180 protein may be derived from a mammal other than a human being.

Also, the SF3b4 protein may be a protein consisting of an amino acid sequence set forth in SEQ ID NO: 100, a protein consisting of an amino acid sequence having a sequence identity of 80% or more, preferably 85% or more, more preferably 90% or more, and particularly preferably 95% or more to the amino acid sequence set forth in SEQ ID NO: 100, and having an ability to synthesize or secrete proteins as a target product when expressed in cells, which is identical to that of the protein consisting of the amino acid sequence set forth in SEQ ID NO: 100, a protein consisting of an amino acid sequence having a sequence similarity of 80% or more, preferably 85% or more, more preferably 90% or more, and particularly preferably 95% or more to the amino acid sequence set forth in SEQ ID NO: 100, and having an ability to promote synthesis or secretion of proteins as a target product when expressed in cells, which is identical to that of the protein consisting of the amino acid sequence set forth in SEQ ID NO: 100, a protein consisting of an amino acid sequence in which one to several amino acids are deleted, substituted or added in the amino acid sequence set forth in SEQ ID NO: 100, and having an ability to promote synthesis or secretion of proteins as a target product when expressed in cells, which is identical to that of the protein consisting of the amino acid sequence set forth in SEQ ID NO: 100, a protein consisting of an amino acid sequence coded for by a base sequence having a sequence identity of 80% or more, preferably 85% or more, more preferably 90% or more, and particularly preferably 95% or more to a base sequence set forth in SEQ ID NO: 101, and having an ability to promote synthesis or secretion of proteins as a target product when expressed in cells, which is identical to that of the protein consisting of the amino acid sequence set forth in SEQ ID NO: 100, or a protein consisting of an amino acid sequence coded for by a base sequence hybridizable under a stringent condition with nucleic acids consisting of a base sequence complementary to the base sequence set forth in SEQ ID NO: 101, having a function of promoting formation of polysomes on the intracellular endoplasmic reticulum membrane.

According to one embodiment, the present invention provides a method of producing a polymeric IgA-type antibody, which includes the step of expressing an IgA-type antibody heavy-chain protein, an antibody light-chain protein, an antibody J-chain protein, and a secretory component protein in a CHO YA7 cell line (name of depository authority: National Institute of Technology and Evaluation, Patent Microorganisms Depositary (NPMD), address of depository authority: #122, 2-5-8 Kazusakamatari, Kisarazu-shi, Chiba 292-0818, Japan, deposit date: Feb. 13, 2013, accession number: NITE BP-01535). The polymeric IgA-type antibody may be a recombinant antibody.

The CHO YA7 cell line is a cell line established by the present inventors, and constitutively expresses the p180 protein and the SF3b4 protein in cells. Therefore, the polymeric IgA-type antibody may be efficiently produced using the production method according to this embodiment.

According to one embodiment, the present invention provides a method of producing a polymeric IgA-type antibody, which includes the step of coexpressing an IgA-type antibody heavy-chain protein, an antibody light-chain protein, an antibody J-chain protein, and a secretory component protein in a single cell. Here, the step is performed by transfecting an expression vector for expressing the IgA-type antibody heavy-chain protein, the antibody light-chain protein, the antibody J-chain protein and the secretory component protein into the cell, the expression vector has a cis-element, which an RNA-binding protein recognizes, binds to or interacts with, downstream from a promoter and also upstream from an initiation codon of nucleic acids coding for the IgA-type antibody heavy-chain protein, the antibody light-chain protein, the antibody J-chain protein, or the secretory component protein. The polymeric IgA-type antibody may be a recombinant antibody.

The cis-element preferably includes one to several base sequences consisting of a sequence motif $GAN_1\text{-}(X)_n\text{-}ACN_2$ (where n is an integer ranging from 3 to 6, and $N_1$ and $N_2$ are each independently one of A, T, G, and C).

The present inventors have found that, when the cis-element is present in a 5'-'untranslated region of a mature mRNA, an RRM protein that recognizes the corresponding cis-element binds to the corresponding cis-element, and enhances transport/localization of mRNA onto a membrane of the endoplasmic reticulum that is a site of protein synthesis, resulting in increased translation efficiency.

Therefore, the polymeric IgA-type recombinant antibody may be more efficiently produced using the production method according to this embodiment. Suitable host cells are as described above.

The cis-element may be a nucleic acid fragment that consists of a base sequence set forth in any one selected from SEQ ID NOs: 21 to 23, a base sequence in which one to several bases are deleted, substituted or added in the base sequence set forth in any one selected from SEQ ID NOs: 21 to 23, and which the RNA-binding protein recognizes, binds to or interacts with, a base sequence having an identity of 80% or more, preferably 85% or more, more preferably 90% or more, and particularly preferably 95% or more to the base sequence set forth in any one selected from SEQ ID NOs: 21 to 23, and which the RNA-binding protein recognizes, binds to or interacts with, or a base sequence hybridizable under a stringent condition with a nucleic acid consisting of a base sequence complementary to a nucleic acid consisting of the base sequence set forth in any one selected from SEQ ID NOs: 21 to 23, and which the RNA-binding protein recognizes, binds to or interacts with. The cis-element may be a nucleic acid fragment consisting of a unnatural base sequence. The nucleic acid fragment may include DNA, RNA, cDNA, etc.

According to this specification, the number of bases to be deleted, substituted or added may, for example, be in a range of 1 to 30, for example in a range of 1 to 15, for example in a range of 1 to 10, and for example in a range of 1 to 5. Also, the number of amino acids to be deleted, substituted or added may, for example, be in a range of 2 to 40, for example in a range of 2 to 30, for example in a range of 2 to 20, for example in a range of 2 to 10, for example in a range of 2 to 7, for example in a range of 2 to 5, for example 5, for example 4, for example 3, and for example 2.

According to this specification, the identity of an amino acid sequence refers to an identity between two target amino acid sequences, and is indicated by a percentage (%) of matched amino acid residues in an optimal alignment of amino acid sequences constructed using a mathematical algorithm known in the related art. The identity of the amino acid sequence may be determined by visual inspection and mathematical calculation, and may be calculated using a homology search program (for example, BLAST, FASTA), a sequence alignment program (for example, ClustalW), genetic information-processing software (for example, GENETYX (registered trademark)), etc. known in the related art.

According to this specification, the identity of the amino acid sequence may be specifically calculated under a default setting condition (Version 2.1, Alignment type: slow, Protein Weight Matrix: Gonnet, GAP OPEN: 10, GAP EXTENSION: 0.1) using a phylogenetic analysis program ClustalW (http://clustalw.ddbj.nig.ac.jp/index.php?lang=ja) published on the website of DDBJ (DNA Data Bank of Japan).

According to this specification, the similarity of an amino acid sequence refers to a similarity between two target amino acid sequences, and is indicated by a percentage (%) of matched amino acid residues and amino acid residues showing similarity in an optimal alignment of amino acid sequences constructed using a mathematical algorithm known in the related art. It is understood that the similarity of the amino acid sequence is indicated by the relationship of amino acid residues whose physicochemical properties are similar to each other, and amino acids belonging to the same groups are, for example, referred to as similar amino acid residues in groups such as aromatic amino acids (Phe, Tyr, and Trp), hydrophobic amino acids (Ala, Leu, Ile, Val, Gly, Pro, Met, Phe, and Trp), aliphatic amino acids (Ala, Leu, Ile, and Val), polar amino acids (Asn and Gln), basic amino acids (Lys, Arg, and His), acidic amino acids (Asp and Glu), amino acids containing a hydroxyl group (Ser and Thr), and amino acids with a small side chain (Gly, Ala, Ser, Thr, and Met). The amino acid residue showing this similarity is expected to have no influence on the phenotypes of proteins. Like the identity, the similarity of the amino acid sequence may be determined by visual inspection and mathematical calculation, and may be calculated using a homology search program (for example, BLAST, PSI-BLAST, and HMMER), genetic information-processing software (for example, GENETYX (registered trademark)), etc. known to those skilled in the related art.

According to this specification, the similarity of the amino acid sequence may be specifically calculated under a default setting condition (Unit size to compare is set to 2) by executing Protein vs. Protein Global Homology using a GENETYX (registered trademark) network version (ver. 11.1.3; GENETYX CORPORATION).

According to this specification, the identity of a base sequence refers to an identity of two target base sequences, and is indicated by a percentage (%) of matched nucleic acids in an optimal alignment of base sequences constructed using a mathematical algorithm known in the related art.

A representative computer program for calculating the identity of a base sequence may include a Wisconsin Package version 10.0 program "GAP" (Devereux, et al., 1984, Nucl. Acids Res., 12: 387) of the Genetics Computer Group (GCG; Madison, Wis.), a BLASTN program (version 2.2.7) available through the National Medical Library website: http://www.ncbi.nlm.nih.gov/blast/bl2seq/bls.html, or an UW-BLAST 2.0 algorithm.

According to this specification, the term "under a stringent condition," for example, refers to a method described in Molecular Cloning-A LABORATORY MANUAL SECOND EDITION (Sambrook et al., Cold Spring Harbor Laboratory Press).

For example, hybridization may be performed by incubating target sequences at 55 to 70° C. for several hours to overnight in a hybridization buffer including 5×SSC (a composition of 20×SSC: 3M sodium chloride, 0.3M citric acid solution, pH 7.0), N-lauroylsarcosine at 0.1% by weight, SDS at 0.02% by weight, a blocking reagent for hybridization of nucleic acids at 2% by weight, and formamide at 50%. Also, a washing buffer used for washing after the incubation is preferably a 1×SSC solution containing SDS at 0.1% by weight, more preferably a 0.1×SSC solution containing SDS at 0.1% by weight.

As long as the cis-element is included in any one or more of the expression vectors containing the IgA-type antibody heavy-chain protein, the antibody light-chain protein, the antibody J-chain protein, and the secretory component protein, the cis-element may have an effect of improving an expression or secretion level of the polymeric IgA-type antibody.

As will be described later, by using the method according to this embodiment, it is possible to prepare a polymeric antibody 26 times to 35 or more times as efficiently as in the conventional methods. Moreover, the monoclonal tetrameric antibody (rS-qIgA) against influenza viruses prepared by such a method has an antigen-binding activity higher than that of the monomeric antibody, and shows 100 or more times the neutralizing activity.

[Method of Improving the Antigen-Binding Activity or Neutralizing Activity of an Antibody]

According to one embodiment, the present invention provides a method of improving the antigen-binding activity or neutralizing activity of the antibody, which includes the step of making an antibody into a polymeric IgA type.

The step of making an antibody into a polymeric IgA type preferably includes the step of coexpressing an IgA-type antibody heavy-chain protein having a heavy-chain variable region of the antibody, a light-chain protein of the antibody, an antibody J-chain protein, and a secretory component protein in a single cell.

The antigen binding activity of an antibody refers to the ability of an antibody to bind to a target molecule per se, but the specificity refers to the ability to not bind to substances other than the target molecule, and a site that exists only in the target molecule is required as a recognition site (an epitope) to ensure high specificity. Although the antigen-binding activity and specificity are generated due to the diversity of sequences of variable regions of the antibody molecules, it is difficult to predict the antigen-binding activity and specificity to the target molecule from the sequences of the variable regions, and antibodies having high antigen-binding activity and specificity need to be cloned from antibody gene in antibody-producing cells generated in a living subject such as a mouse, or a library of artificially prepared variable regions using any methods. Also, since both the specificity and the antigen-binding activity independently depend on the sequences of the variable regions, it is very difficult to improve the antigen-binding activity in an artificial manner without a change in the specificity of the obtained antibody, that is, without a change in the epitope to be recognized.

On the other hand, as will be described later, the present inventors have found that the polymeric IgA-type antibody may be produced by coexpressing the IgA-type antibody heavy-chain protein, the antibody light-chain protein, the antibody J-chain protein, and the secretory component protein in a single cell. Suitable host cells are as described above.

Also, the present inventors have found that the antigen-binding activity or neutralizing activity of the antibody may be improved by making a monomeric antibody into a polymer. For example, as will be described later, the virus-neutralizing activity per 1 mole of the antibody may be improved by a factor of 100 or more, compared to the monomeric antibody, by making the monomeric antibody into a polymer.

Antibodies to be improved in the antigen-binding activity or neutralizing activity are not particularly limited, and may, for example, include a human antibody, a non-human mammal-derived antibody, a rodent-derived antibody, a bird-derived antibody, etc. Also, a class of antibodies is not particularly limited, and may, for example, include IgG-type, IgM-type, IgE-type, IgA-type, IgD-type, and IgY-type antibodies, etc. The antigen-binding activity or neutralizing activity may be improved without a change in specificity of pre-existing antibodies using the method according to this embodiment.

The method according to this embodiment may be applied by binding a variable region of the interesting antibody to a constant region of the IgA-type antibody to convert the antibody into an IgA type by means of genetic recombination. For example, an IgG-type monoclonal antibody may be converted into an IgA-type monoclonal antibody by transplanting a variable region of the IgG-type monoclonal antibody to the backbone framework of an IgA-type antibody. Alternatively, the IgG-type monoclonal antibody may be converted into an IgA type by transplanting only CDR region of the antibody to be improved in the antigen-binding activity into the CDR region of the IgA-type antibody. A subclass of IgA may be an IgA1 type or an IgA2 type.

The method according to this embodiment is highly versatile as technology capable of converting an IgG-type monoclonal antibody, which has a variable region that recognizes the same epitope, into a high-binding type and a high-activity type. Therefore, the method may be widely applied to products using monoclonal antibodies such as antibodies for medicines, diagnostic antibodies used for immunochromatography, immunohistochemistry, ELISA, etc., and other antibodies for research applications, etc.

To indicate the positions of the amino acid residues in the amino acid sequence of the constant region of the IgA1 antibody, the numbering disclosed by Liu Y S et al. (Complete covalent structure of a human IgA1 immunoglobulin. Science. 1976; 193: 1017-20) was used in this specification. Also, to indicate the positions of amino acid residues of constant regions of IgA2 antibody allotypes (IgA2m1, IgA2m2, and IgA2(n)), the constant region of each of the IgA2 antibody allotypes and the constant region of the IgA1 antibody were aligned, and the numbering of the amino acid residues of the corresponding IgA1 antibody was used. A sequence of amino acids at positions 224 to 236 (STPPTPSPSTPPT) of the IgA1 antibody was omitted since there were no corresponding amino acids in the IgA2 antibody allotypes.

EXAMPLES

Hereinafter, the present invention will be described with reference to experimental examples thereof, but the present invention is not intended to be limited by the following experimental examples.

Experimental Example 1: Isolation of Variable Region Gene of Human-Derived Antibody Induced by Nasal Whole Inactivated Influenza Virus Vaccine and Preparation of Monoclonal IgG1 Antibody Using the Same (Vaccination and Recovery of Peripheral Blood Lymphocytes)

A whole inactivated virion vaccine for a highly pathogenic avian influenza virus A/H5N1 was nasally inoculated into healthy adults twice at a three-week interval (250 μL per nostril; a total dose of 500 μL). An inactivated whole particle vaccine containing 45 μg of hemagglutinin (HA) was used as the vaccine. Peripheral blood was collected after 7 days of the second vaccination, and peripheral blood lymphocytes were collected using a blood cell separation solution, Lymphoprep (trademark) (AXIS-SHIELD).

(Isolation of Antibody-Producing Plasma Cells and cDNA Preparation)

Isolation of antibody-producing plasma cells induced in peripheral blood by intranasal vaccination was performed using FACS Aria (BD Bioscience). A cell population of cell surface markers CDT, CD3⁻, CD4⁻, CD10⁻, CD20⁻, Ig CD19$^{low}$, CD27$^{high}$, and CD38$^{high}$ was collected as antibody-producing plasma cells, and separated and collected as single cells. Single antibody-producing plasma cells were collected in a 96-well plate in which 9 μL of sterile water including 45 ng of carrier RNA was dispensed into each well. Preparation of cDNA was performed based on the article of T. Tiller et al. (J Immunol Methods, 329, 112-24, 2008). Specifically, 6 μL of a mixture containing Superscript III RT (Life Technologies Inc.), Randam Hexamer (Life Technologies Inc.), RNaseOUT (Life Technologies Inc.), and dNTP mix (QIAGEN N.V.) was added to each well in which the cells were collected, and then reacted at 50° C. for 50 minutes and at 85° C. for 5 minutes to prepare cDNA.

(Determination of Antibody Isotypes)

Using 2 μL of the prepared cDNA, isotypes of an antibody heavy chain isolated in each well were determined by Real-time PCR. TaqMan probes and primers were prepared for each of constant regions of IgG, IgA, and IgM. The TaqMan probes for IgG IgA, and IgM were labeled with FAM, HEX, and Cy5, respectively. Analysis was performed using LightCycler 480 (F. Hoffmann-La Roche, Ltd.) using QuantiTect Multiplex PCR NoROX Master Mix (QIAGEN N.V.).

(Amplification and Sequencing of Antibody Variable Region Genes)

Amplification of an antibody variable region gene was performed based on the article of T. Tiller et al. (J Immunol Methods, 329, 112-24, 2008). Specifically, a mixture including 11.5 µL of HotStarTaq DNA polymerase (QIAGEN N.V.), dNTP mix, and a primer set for amplifying each of the antibody variable region genes was added to 1 µL of the prepared cDNA, and subjected to the first PCR reaction. Also, the second PCR reaction was performed using a primer set designed further inside for each of the genes included in 1 µL of the resulting PCR product. In any PCR reaction, amplification was performed under conditions of one cycle of 95° C. for 15 minutes, 43 cycles of 94° C. for 30 seconds, 58° C. for 20 seconds and 72° C. for 60 seconds, and one cycle of 72° C. for 2 minutes. Also, the base sequence analysis (sequencing) of PCR products was performed using a conventional method.

(Cloning of Antibody Variable Region Gene into Expression Vector)

PCR of an antibody variable region gene was performed according to the instructions using PrimeSTAR (registered trademark) MAX DNA Polymerase (TaKaRa). The above-described first PCR product was used as a template, and a pair of primers suitable for a locus to be amplified were selected as the primers based on the sequencing results of the above-described second PCR product. The PCR conditions were 25 cycles at 98° C. for 10 seconds, 55° C. for 5 seconds, and 72° C. for 10 seconds. The PCR product was purified according to the instructions using MonoFas (registered trademark) DNA Purification Kit I (GL Sciences Inc.), and eluted in 30 µL of Buffer C.

The purified PCR product was digested with restriction enzymes under suitable conditions using AgeI-HF (all chains), and SalI-HF (a heavy chain), BsiWI (a κ chain) or XhoI (a κ chain) (commercially available from NEB Co.) in a total volume of 30 µL. Expression vectors γ1 HC (a heavy chain), κ LC (a κ chain), and κ LC (a λ chain) corresponding to the respective chains were also enzymatically digested with the same combination of restriction enzymes. The restriction enzyme product was purified according to the instructions using MonoFas (registered trademark) DNA Purification Kit I (GL Sciences Inc.), and eluted in 20 µL of Buffer C.

Ligation of DNA digested with the restriction enzymes was performed in a total volume of 10 µL according to the instructions using a DNA ligation kit <Mighty Mix> (TaKaRa). Competent Quick DH5α (TOYOBO) was transformed with 10 µL of the ligation products by heating the competent cells at 42° C. Plasmid extraction was performed according to the instructions using a PureYield (trademark) plasmid miniprep system (Promega Corporation).

Next, four clones were sequenced per gene. A sequencing reaction of the extracted plasmid was performed according to the instructions using a BigDye (registered trademark) Terminator v3.1 Cycle sequencing kit (Life Technologies Inc.). The reaction product was purified according to the instructions using BigDye XTerminator (trademark) kit (Life Technologies Inc.), and sequenced using an Applied Biosystems 3130 genetic analyzer (Life Technologies Inc.). Alignment analysis of the read sequence and the sequence of the second PCR product was performed to select a sample holding the most consensus sequence.

(Expression of Recombinant Monoclonal IgG1 Antibody)

An Expi293 (trademark) expression system (Life Technologies Inc.) was used according to the instructions to produce a recombinant antibody. As one example, a 30 mL system will be described below.

It was confirmed that Expi293F cells subcultured had a density of more than $3.0 \times 10^6$ cells/mL and survival rate of more than 95%, and the cells were not aggregated. The number of cells was adjusted to $2.9 \times 10^6$ cells/mL using an Expi293 expression medium warmed at 37° C. 25.5 mL of the prepared cell suspension was transferred to a disposable Erlenmeyer flask equipped with a vent filter cap, returned to an incubator for cell culture set to 37° C. and 8% $CO_2$, and cultured by shaking at 125 rpm. 30 µg of plasmid DNA (15 µg each of a heavy chain and a light chain of IgG) was added to 1.5 mL of an Opti-MEM I medium. 80 µL of an Expi-Fectamine 293 reagent was added to 1.5 mL of a separately prepared Opti-MEM I medium. After a DNA solution and an ExpiFectamine solution were incubated at room temperature for 5 minutes, a total volume of the DNA solution was added to an ExpiFectamine solution, and then incubated at room temperature for 20 to 30 minutes. After a transfection mix was added to the cells, the cells were returned to an incubator for cell culture set to 37° C. and 8% $CO_2$, and cultured by shaking at 125 rpm. After 16 to 18 hours of transfection, 150 µL of ExpiFectamine 293 Transfection Enhancer 1 and 1.5 mL of ExpiFectamine 293 Transfection Enhancer 2 were added. The cells were returned to an incubator for cell culture set to 37° C. and 8% $CO_2$, and cultured by shaking at 125 rpm. A supernatant was collected after 6 days of the transfection.

(Purification of Recombinant Monoclonal IgG1 Antibody)

Cell debris was removed by centrifugation at 1,000×g for 10 minutes, and a supernatant was then filtered with a Millex-HV filter unit (Millipore Corporation). Purification of the recombinant antibody was performed according to the instructions using a CaptureSelect (trademark) human Fc affinity matrix (Life Technologies Inc.). Specifically, a column was equilibrated with a 10-column volume of phosphate-buffered saline (PBS), loaded with a sample, and washed with a 10-column volume of PBS. Then, the antibody was eluted with a 5-column volume of 0.1M glycine-HCl (pH 3.0), and the resulting eluate was neutralized with 1M Tris-HCl (pH 9.0). The column was re-equilibrated with a 10-column volume of PBS. A concentration of the antibody was measured using NanoDrop (Thermo Scientific Ltd.). The antibody was concentrated according to the instructions using an Amicon (registered trademark) ultracentrifugal filter device (Millipore Corporation). In a Zeba Desalt spin column (Thermo Scientific Ltd.), the buffer of the eluate was replaced with a phosphate buffer (PB, pH 7.4) according to the instructions. After the buffer replacement, the concentration was measured using NanoDrop.

(Confirmation of Recombinant Monoclonal IgG1 Antibody)

To confirm the purified antibody, SDS polyacrylamide gel electrophoresis (SDS-PAGE) was performed according to the instructions using a NuPAGE (registered trademark) Bis-Tris gel (Life Technologies Inc.). FIG. 1 is an image showing results of the SDS-PAGE. It was confirmed that the antibody clones G2, H10, D11, F9, F11, H5, and C1 were converted to IgG1 types. The expression levels varied depending on the clones. In a 40 mL culture system, approximately 40 mg of the clone B12, approximately 4 mg of the clone D11, approximately 1.5 mg of the clone F9, approximately 2.1 mg of the clone F11, and 1 mg of the clone H5 were able to be prepared.

Experimental Example 2: Preparation of Monoclonal IgA Antibody Carrying the Same Variable Region as Monoclonal IgG Antibody Whose Characteristics are Analyzed An IgA-type recombinant antibody was prepared using the following method. The IgG1 antibodies prepared in Experimental Example 1 are not particularly limited, and antibodies having known sequences may be made into IgA types using the following method.

(Preparation of α1 HC Expression Vector)

An expression vector α1 HC containing a constant region gene of the IgA1 antibody was prepared. PCR of the constant region gene of the IgA1 antibody was performed according to the instructions using PrimeSTAR (registered trademark) MAX DNA Polymerase (TaKaRa).

Specifically, the constant region gene of the IgA1 antibody was amplified using pFUSE-CHIg-hA1 (InvivoGen Ltd.) as a template. The PCR conditions were 30 cycles at 98° C. for 10 seconds, 55° C. for 5 seconds, and 72° C. for 30 seconds. The PCR product was purified according to the instructions using MonoFas (registered trademark) DNA Purification Kit I (GL Sciences Inc.), and eluted in 30 μL of Buffer C. The purified PCR product and a γ1 HC plasmid were digested with restriction enzymes XhoI and HindIII-HF (commercially available from NEB Co.) at 37° C. in a total volume of 30 μL. The restriction enzyme-digested products were purified according to the instructions using MonoFas (registered trademark) DNA Purification Kit I (GL Sciences Inc.), and eluted in 20 μL of Buffer C. Ligation of the restriction enzyme-digested DNAs was performed in a total volume of 10 μL according to the instructions using a DNA ligation kit <Mighty Mix> (TaKaRa). 10 μL of the ligation product was warmed at 42° to be transformed into Competent Quick DH 5α.

Plasmid extraction was performed according to the instructions using a PureYield (trademark) Plasmid Miniprep System (Promega Corporation). A sequencing reaction of the extracted plasmid was performed according to the instructions using a BigDye (registered trademark) Terminator v3.1 Cycle sequencing kit (Life Technologies Inc.). The reaction products were purified according to the instructions using a BigDye XTerminator (trademark) kit (Life Technologies Inc.), and sequenced using an Applied Biosystems 3130 genetic analyzer (Life Technologies Inc.).

(PCR Cloning of Antibody Variable Region Gene into α1 HC Expression Vector)

PCR of the antibody variable region gene was performed according to the instructions using PrimeSTAR (registered trademark) MAX DNA Polymerase (TaKaRa). Using the antibody gene cloned into the γ1 HC expression vector as a template, a reverse primer was replaced with a primer for the α1 HC expression vector, and the PCR conditions were 25 cycles at 98° C. for 10 seconds, 55° C. for 5 seconds, and 72° C. for 5 seconds.

The PCR product was purified according to the instructions using MonoFas (registered trademark) DNA Purification Kit I (GL Sciences Inc.), and eluted in 30 μL of Buffer C. The purified PCR product and an α1 HC expression vector were digested with restriction enzymes under suitable conditions using AgeI-HF and NheI-HF (commercially available from NEB Co.) in a total volume of 30 μL. The restriction enzyme-digested product was purified according to the instructions using MonoFas (registered trademark) DNA Purification Kit I (GL Sciences Inc.), and eluted in 20 μL of Buffer C. Ligation of the restriction enzyme-digested DNAs was performed in a total volume of 10 μL according to the instructions using a DNA ligation kit <Mighty Mix> (TaKaRa). 10 μL of the ligation product was warmed at 42° C. to be transformed into Competent Quick DH 5α (TOYOBO).

Plasmid extraction was performed according to the instructions using a PureYield (trademark) Plasmid Miniprep System (Promega Corporation). A sequencing reaction of the extracted plasmid was performed according to the instructions using a BigDye (registered trademark) Terminator v3.1 Cycle sequencing kit (Life Technologies Inc.). The reaction product was purified according to the instructions using a BigDye XTerminator (trademark) kit (Life Technologies Inc.), and sequenced using an Applied Biosystems 3130 genetic analyzer (Life Technologies Inc.). Based on the sequencing results, it was confirmed that antibody variable region gene cloned into α1 HC expression vector was identical to the antibody gene cloned into the γ1 HC expression vector.

(Expression of Recombinant Monoclonal IgA1 Antibody)

An Expi293 (trademark) expression system (Life Technologies Inc.) was used according to the instructions to produce a recombinant antibody. As one example, a 30 mL system will be described below.

It was confirmed that Expi293F cells subcultured had a density of more than $3.0 \times 10^6$ cells/mL and survival rate of more than 95%, and the cells were not aggregated. The number of cells was adjusted to $2.9 \times 10^6$ cells/mL using an Expi293 expression medium warmed at 37° C. 25.5 mL of the prepared cell suspension was transferred to an disposable Erlenmeyer flask equipped with a vent filter cap, returned to an incubator for cell culture set to 37° C. and 8% $CO_2$, and cultured by shaking at 125 rpm. 30 μg of plasmid DNA (15 μg each of a heavy chain and a light chain of IgA1) was added to 1.5 mL of an Opti-MEM I medium. 80 μL of an ExpiFectamine 293 reagent was added to 1.5 mL of a separately prepared Opti-MEM I medium. After a DNA solution and an ExpiFectamine solution were incubated at room temperature for 5 minutes, a total volume of the DNA solution was added to an ExpiFectamine solution, and then incubated at room temperature for 20 to 30 minutes. After a transfection mix was added to the cells, the cells were returned to an incubator for cell culture set to 37° C. and 8% $CO_2$, and cultured by shaking at 125 rpm. After 16 to 18 hours of transfection, 150 μL of ExpiFectamine 293 Transfection Enhancer 1 and 1.5 mL of ExpiFectamine 293 Transfection Enhancer 2 were added. The cells were returned to an incubator for cell culture set to 37° C. and 8% $CO_2$, and cultured by shaking at 125 rpm. A supernatant was collected after 6 days of the transfection.

(Purification of Recombinant Monoclonal IgA1 Antibody)

Cell debris was removed by centrifugation at 1,000×g for 10 minutes, and a supernatant was then filtered with a Millex-HV filter unit (Millipore Corporation). Purification of the recombinant antibody was performed according to the instructions using a CaptureSelect (trademark) human IgA affinity matrix (Life Technologies Inc.). Specifically, a column was equilibrated with a 10-column volume of phosphate-buffered saline (PBS), loaded with a sample, and washed with a 10-column volume of PBS. Then, the antibody was eluted with a 5-column volume of 0.1M glycine-HCl (pH 3.0), and the resulting eluate was neutralized with 1M Tris-HCl (pH 9.0). The column was re-equilibrated with a 10-column volume of PBS. A concentration of the antibody was measured using NanoDrop (Thermo Scientific Ltd.). The antibody was concentrated according to the instructions using an Amicon (registered trademark) ultra-centrifugal filter device (Millipore Corporation). In a Zeba Desalt spin column (Thermo Scientific Ltd.), the buffer of the eluate was replaced with a phosphate buffer (PB, pH 7.4) according to the instructions. After the buffer replacement, the concentration was measured using NanoDrop.

(Confirmation of Recombinant Monoclonal IgA1 Antibody)

Figure 2:
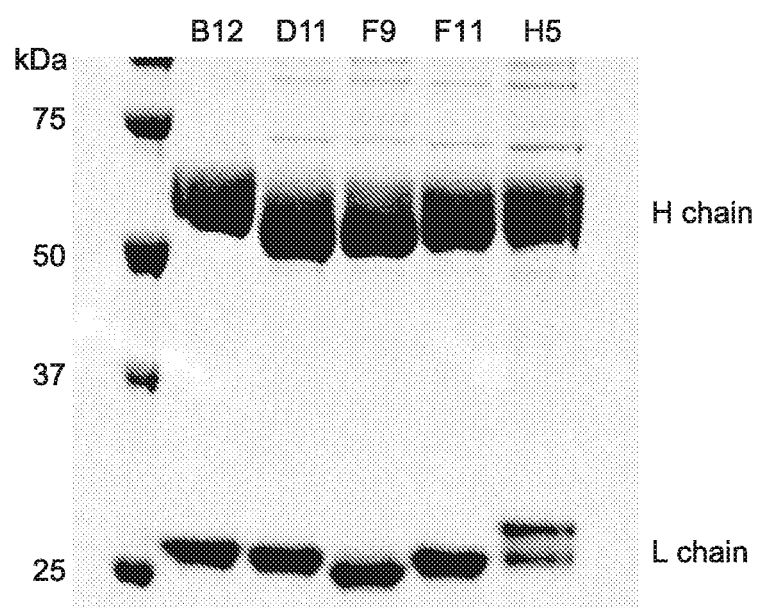
FIG. 2 is an image showing results of running respective clones of an expressed and purified recombinant monoclonal IgA1 antibody on SDS polyacrylamide gel electrophoresis (SDS-PAGE) to stain the recombinant monoclonal IgA1 antibody with Simply Blue (trademark) Safe Stain.

To confirm the purified antibody, SDS polyacrylamide gel electrophoresis (SDS-PAGE) was performed according to the instructions using a NuPAGE (registered trademark) Bis-Tris gel (Life Technologies Inc.). FIG. 2 is an image showing results of the SDS-PAGE. It was confirmed that the antibody clones B12, D11, F9, F11, and H5 were converted to IgA1 types.

Experimental Example 3: Production of Monoclonal IgA Antibody Dimer

A dimeric IgA1-type antibody was prepared using the IgA1 antibody expression construct prepared in Experimental Example 2.

(Cloning of Antibody J Chain)

An artificial gene (SEQ ID NO: 24) in which an XhoI cleavage site and a Kozak sequence were added to the 5' side of a coding sequence (CDS) of the J chain (GenBank accession no. NM_144646) and a NotI cleavage site was added to the 3' side of the CDS was synthesized for the antibody J chain using an artificial gene synthesis service (Operon Biotechnologies Inc.). A J chain gene was digested with restriction enzymes under suitable conditions using XhoI and NotI-HF (commercially available from NEB Co.). Then, the restriction enzyme-digested product was cloned into a pCXSN vector (a mammalian cell expression vector composed of a CMV promoter and SV40 polyA) digested with the same restriction enzymes to obtain pCXSN-hJC which was a plasmid for expressing the antibody J chain.

(Expression of Dimeric IgA1-Type Antibody)

An Expi293 (trademark) expression system (Life Technologies Inc.) was used according to the instructions to produce a dimeric IgA1-type antibody. As one example, a 30 mL system will be described below.

It was confirmed that Expi293F cells subcultured had a density of more than $3.0 \times 10^6$ cells/mL and survival rate of more than 95%, and the cells were not aggregated. The number of cells was adjusted to $2.9 \times 10^6$ cells/mL using an Expi293 expression medium warmed at 37° C. 25.5 mL of the prepared cell suspension was transferred to a disposable Erlenmeyer flask equipped with a vent filter cap, returned to an incubator for cell culture set to 37° C. and 8% $CO_2$, and cultured by shaking at 125 rpm. Plasmid DNA (a J chain-expressed group: 12 μg each of a heavy chain and a light chain of IgA1, and 6 μg of a J chain; and a J chain-unexpressed group: 15 μg each of the heavy chain and light chain of IgA1) was added to 1.5 mL of an Opti-MEM I medium.

80 μL of an ExpiFectamine 293 reagent was added to 1.5 mL of a separately prepared Opti-MEM I medium. After a DNA solution and an ExpiFectamine solution were incubated at room temperature for 5 minutes, a total volume of the DNA solution was added to an ExpiFectamine solution, and then incubated at room temperature for 20 to 30 minutes. After a transfection mix was added to the cells, the cells were returned to an incubator for cell culture set to 37° C. and 8% $CO_2$, and cultured by shaking at 125 rpm. After 16 to 18 hours of transfection, 150 μL of ExpiFectamine 293 Transfection Enhancer 1 and 1.5 mL of ExpiFectamine 293 Transfection Enhancer 2 were added. The cells were returned to an incubator for cell culture set to 37° C. and 8% $CO_2$, and cultured by shaking at 125 rpm. A supernatant was collected after 6 days of the transfection.

(Purification of Expressed IgA1 Antibody)

Cell debris was removed by centrifugation at 1,000×g for 10 minutes, and a supernatant was then filtered with a Millex-HV filter unit (Millipore Corporation). Purification of the recombinant antibody was performed according to the instructions using a CaptureSelect (trademark) human IgA affinity matrix (Life Technologies Inc.). Specifically, a column was equilibrated with a 10-column volume of phosphate-buffered saline (PBS), loaded with a sample, and washed with a 10-column volume of PBS. Then, the antibody was eluted with a 5-column volume of 0.1M glycine-HCl (pH 3.0), and the resulting eluate was neutralized with 1M Tris-HCl (pH 9.0). The column was re-equilibrated with a 10-column volume of PBS. A concentration of the antibody was measured using NanoDrop (Thermo Scientific Ltd.). The antibody was concentrated according to the instructions using an Amicon (registered trademark) ultra-centrifugal filter device (Millipore Corporation). In a Zeba Desalt spin column (Thermo Scientific Ltd.), the buffer of the eluate was replaced with a phosphate buffer (PB, pH 7.4) according to the instructions. After the buffer replacement, the concentration was measured using NanoDrop.

(Confirmation of Expressed IgA1 Antibody)

Figure 3:
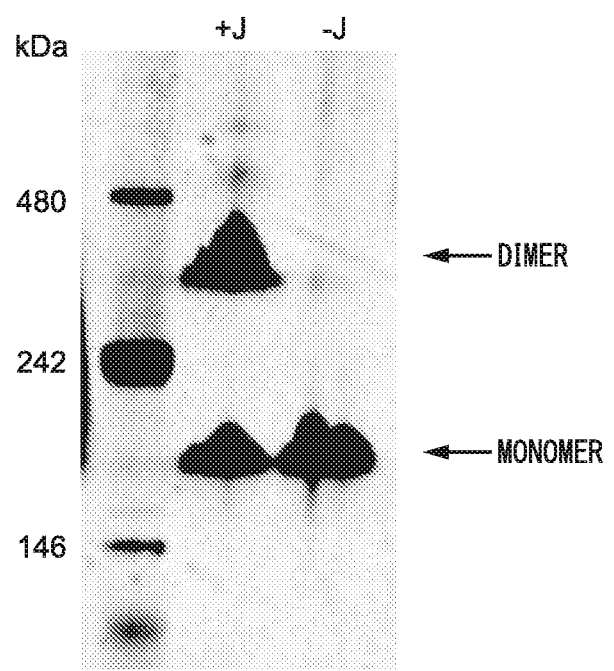
FIG. 3 is an image showing results of running an IgA1 antibody, which is expressed and purified upon non-coexpression of a J chain or coexpression of the J chain, on blue native polyacrylamide gel electrophoresis (BN-PAGE) to stain the IgA1 antibody with a staining solution (0.02% Coomassie R-250, 30% methanol, and 10% acetic acid).

To confirm the purified antibody, blue native polyacrylamide gel electrophoresis (BN-PAGE; 3-13%, Invitrogen) was performed. FIG. 3 is an image showing results of the BN-PAGE. It was confirmed that a band of the monomeric IgA type recombinant antibody was observed in the J chain-unexpressed group (−J), whereas, in addition to a monomer band, a band of the dimeric IgA type recombinant antibody was observed in the J chain-expressed group (+J).

Experimental Example 4: Production of Monoclonal IgA Antibody Polymer

A polymeric IgA1-type antibody was prepared using the IgA1 antibody expression construct prepared in Experimental Example 2.

(Cloning of Secretory Component (SC))

The artificial DNA fragment in which an XhoI cleavage site and a Kozak sequence were added to the 5' side of $185^{th}$ to $2005^{th}$ residues of a polymeric immunoglobulin receptor (GenBank accession no. NM_002644) and a HindIII cleavage site, a thrombin cleavage site, a histidine tag, and a NotI cleavage site were added to the 3' side of the $185^{th}$ to $2005^{th}$ residues were designed and two artificial DNA fragments (i.e., a 5'-side fragment and a 3'-side fragment) were synthesized so as to overlapped each other using GeneArt (registered trademark) Strings (trademark) DNA fragments (Life Technologies Inc.). Overlap PCR in which a Prime-STAR (registered trademark) MAX DNA Polymerase (TaKaRa) was used was performed using the two synthesized DNA fragments as templates to amplify a gene fragment coding for the secretory component (SC) (SEQ ID NO: 25). Then, the amplified gene fragment was digested with restriction enzymes XhoI and NotI, and cloned into a pCXSN vector to obtain a secretory component expression plasmid pCXSN-hSC-HisTag. Also, inverse PCR was performed using the pCXSN-hSC-HisTag as a template to prepare pCXSN-hSC expressing only the secretory component, from which the HindIII cleavage site, the thrombin cleavage site, and the histidine tag added to the 3' side were removed. The polymeric antibody was able to be prepared using either plasmid as the secretory component.

(Expression of Polymeric IgA1-Type Antibody)

An Expi293 (trademark) expression system (Life Technologies Inc.) was used according to the instructions to produce a polymeric IgA1-type antibody. As one example, a 30 mL system will be described below.

It was confirmed that Expi293F cells subcultured had a density of more than $3.0 \times 10^6$ cells/mL and survival rate of more than 95%, and the cells were not aggregated. The number of cells was adjusted to $2.9 \times 10^6$ cells/mL using an Expi293 expression medium warmed at 37° C. 25.5 mL of the prepared cell suspension was transferred to a disposable Erlenmeyer flask equipped with a vent filter cap, returned to an incubator for cell culture set to 37° C. and 8% $CO_2$, and cultured by shaking at 125 rpm. Plasmid DNA (12 μg each of a heavy chain and a light chain of IgA1, and 6 μg each of a J chain and a secretory component) was added to 1.5 mL of an Opti-MEM I medium.

80 μL of an ExpiFectamine 293 reagent was added to 1.5 mL of a separately prepared Opti-MEM I medium. After a DNA solution and ExpiFectamin solution were incubated at room temperature for 5 minutes, a total volume of the DNA solution was added to an ExpiFectamine solution, and then incubated at room temperature for 20 to 30 minutes. After a transfection mix was added to the cells, the cells were returned to an incubator for cell culture set to 37° C. and 8% $CO_2$, and cultured by shaking at 125 rpm. After 16 to 18 hours of transfection, 150 μL of ExpiFectamine 293 Transfection Enhancer 1 and 1.5 mL of ExpiFectamine 293 Transfection Enhancer 2 were added. The cells were returned to an incubator for cell culture set to 37° C. and 8%

$CO_2$, and cultured by shaking at 125 rpm. A supernatant was collected after 6 days of the transfection.

(Purification of Expressed IgA1 Antibody)

Cell debris was removed by centrifugation at 1,000×g for 10 minutes, and a supernatant was then filtered with a Millex-HV filter unit (Millipore Corporation). Purification of the recombinant antibody was performed according to the instructions using a CaptureSelect (trademark) human IgA affinity matrix (Life Technologies Inc.). Specifically, a column was equilibrated with a 10-column volume of phosphate-buffered saline (PBS), loaded with a sample, and washed with a 10-column volume of PBS. Then, the antibody was eluted with a 5-column volume of 0.1M glycine-HCl (pH 3.0), and the resulting eluate was neutralized with 1M Tris-HCl (pH 9.0). The column was re-equilibrated with a 10-column volume of PBS. A concentration of the antibody was measured using NanoDrop (Thermo Scientific Ltd.). The antibody was concentrated according to the instructions using an Amicon (registered trademark) ultra-centrifugal filter device (Millipore Corporation). In a Zeba Desalt spin column (Thermo Scientific Ltd.), the buffer of the eluate was replaced with a phosphate buffer (PB, pH 7.4) according to the instructions. After the buffer replacement, the concentration was measured using NanoDrop.

(Size Fractionation of Polymeric IgA1-Type Antibody)

The concentrated polymeric IgA1-type antibody was fractionated by gel filtration chromatography using AKTA explorer10 (GE Healthcare). Superose6 10/300 GL (GE Healthcare) was used as the column. Dulbecco's phosphate-buffered saline (DPBS) was flushed according to the following protocol: a flow rate of 0.5 mL/min, a column equilibration of 1.5 column volume, and an elution of 0.5 mL per fraction (a total column volume of 1.5).

Eluted samples were collected for each fraction, and fractions containing IgA were concentrated using an Amicon (registered trademark) ultra-centrifugal filter device (Millipore Corporation). In a Zeba Desalt spin column (Thermo Scientific Ltd.), the buffer of the sample was replaced with a phosphate buffer (PB, pH 7.4) according to the instructions. After the buffer exchange, the concentration was measured using NanoDrop.

Figure 4:
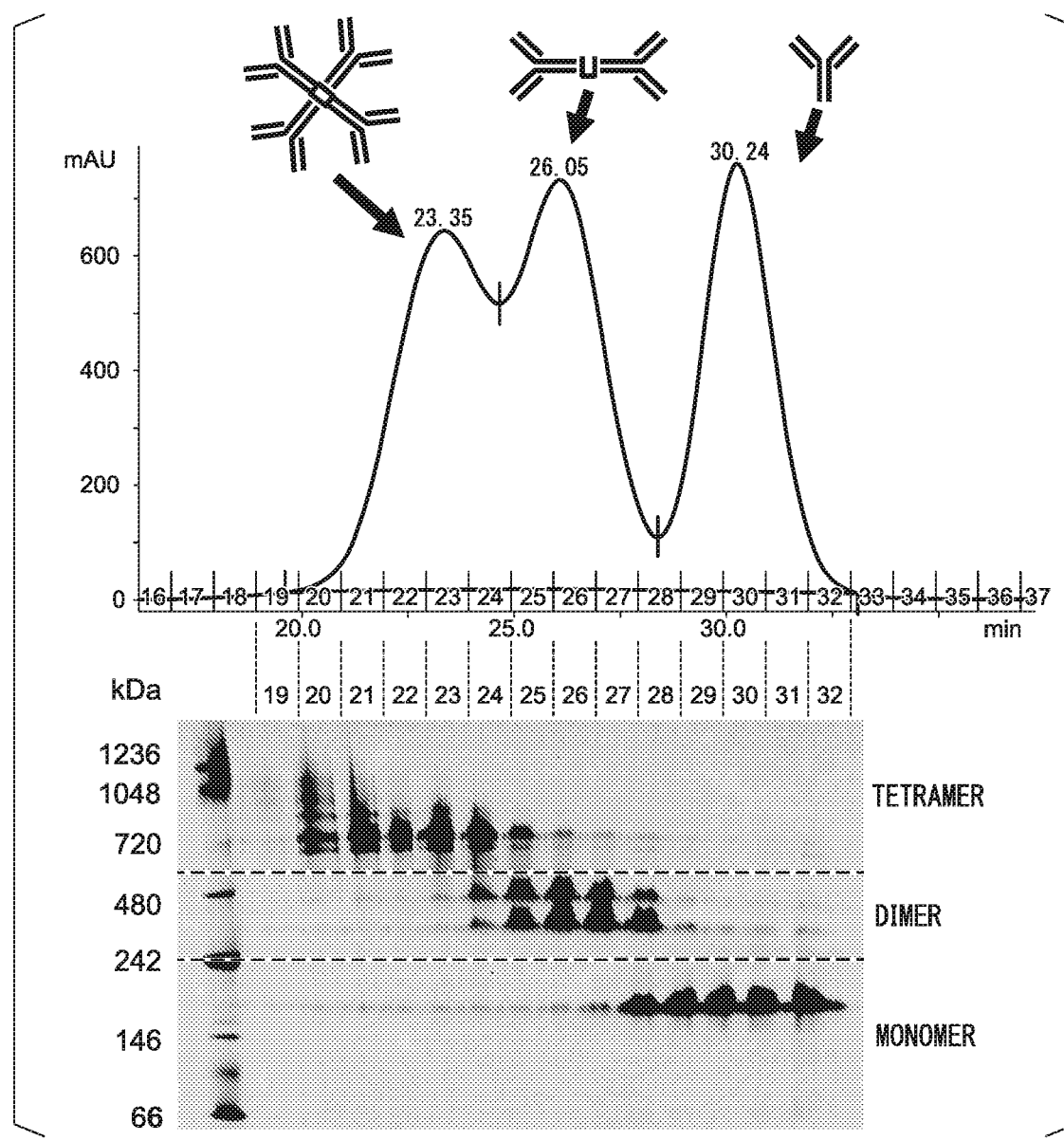
FIG. 4 is a chart of gel filtration chromatography for size fractionation of a polymeric IgA1 antibody, and an image showing results of running respective fractions on blue native polyacrylamide gel electrophoresis (BN-PAGE) to stain the fractions with a staining solution (0.02% Coomassie R-250, 30% methanol, 10% acetic acid).
Figure 5A:
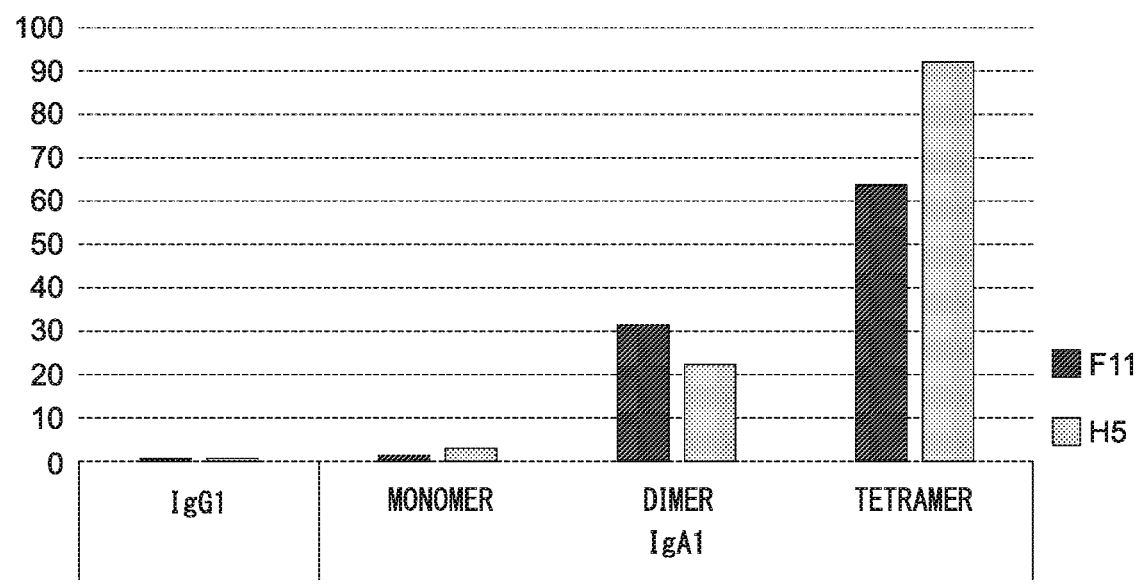
FIG. 5A is a graph illustrating ratios of neutralizing activities of a monomeric IgA1-type antibody, a dimeric IgA1-type antibody and a tetrameric IgA1-type antibody when the influenza virus-neutralizing activity of a monomeric IgG1-type antibody is set to 1. Each of the ratios represents a ratio of the neutralizing activity per unit weight of a protein.
Figure 5B:
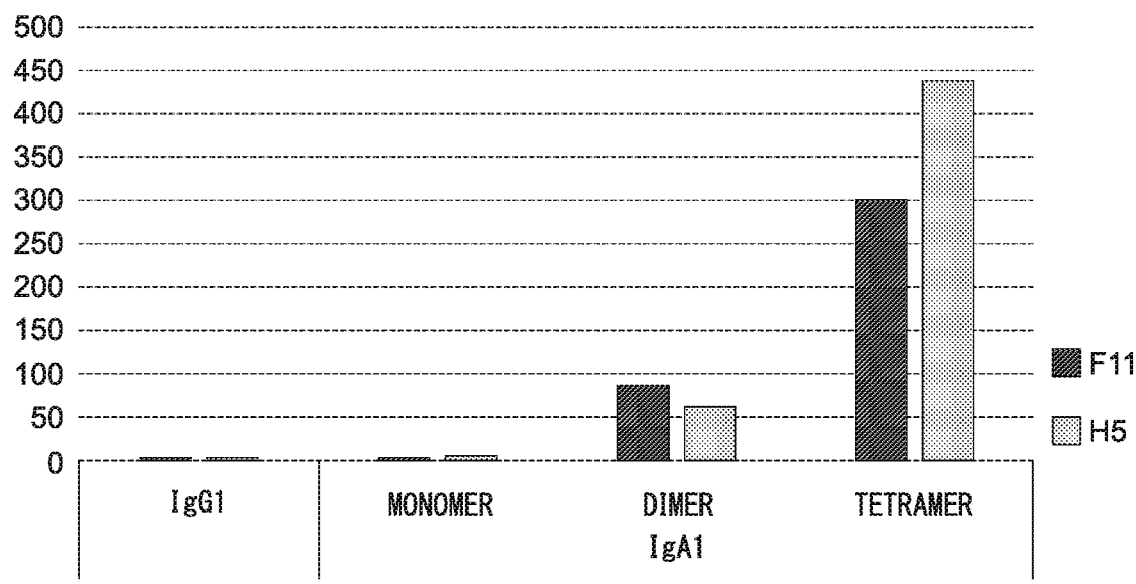
FIG. 5B is a graph illustrating ratios of neutralizing activities of the monomeric IgA1-type antibody, the dimeric IgA1-type antibody and the tetrameric IgA1-type antibody when the influenza virus-neutralizing activity of the monomeric IgG1-type antibody is set to 1. Each of the ratios represents a ratio of the neutralizing activity per molecule.

Next, antibodies contained in each fraction were confirmed using blue native PAGE (BN-PAGE) under non-reducing conditions. FIG. 4 is a chart of gel filtration chromatography, and an image showing results of the BN-PAGE for the antibodies contained in fractions 19 to 32. It was revealed that tetramers, dimers and monomers were included in the expressed IgA1-type antibody. This result was the first report that a tetrameric IgA-type recombinant antibody was prepared.

Experimental Example 5: Examination of Influenza Virus-Neutralizing Activity

A human IgG1 antibody against influenza viruses was prepared in Experimental Example 1, and an IgA1 antibody having the same variable region as the corresponding IgG1 antibody was prepared in Experimental Example 2. Also, polymeric IgA1-type antibodies were prepared in Experimental Examples 3 and 4. Then, the influenza virus-neutralizing activity was examined using these antibodies.

The neutralizing activity of each of the prepared antibodies was quantified by measuring the minimum neutralization concentration using a microneutralization test. Two-fold serial dilutions of a sample were prepared, and mixed with a virus solution of 100 $TCID_{50}$ (100 times a 50% tissue culture infective dose), and the resulting mixture was then incubated at 37° C. for 30 minutes. Thereafter, this mixture was added to MDCK cells (a cell line derived from a canine kidney), and cultured for 4 days. Then, a value obtained by dividing a concentration of the sample by the maximum dilution ratio of the sample, in which a cytopathic effect by influenza viruses was not able to be determined under a microscope, was used as the minimum neutralization concentration. It meant that the lower the minimum neutralization concentration was, the higher the virus-neutralizing activity was.

(Influenza Virus-Neutralizing Activity of Monomeric Recombinant Antibody)

The influenza virus-neutralizing activity was measured using monomeric IgG1-type antibody and monomeric IgA1-type antibody of the antibody clones G2, H10, D11, F9, F11, H5, B12, and C1. An A/H5N1 strain (clade 2.1) and an A/H1N1 strain were used as the viruses.

The results are listed in Table 1. It meant that the lower the minimum neutralization concentration was, the higher the virus-neutralizing activity was. It was apparent that the antibodies of the clones F11 and H5 showed good neutralizing activity against both the H5N1 strain and the H1N1 strain.

TABLE 1

Minimum antibody concentration (minimum neutralization concentration) at which clones of each of monomeric IgG1-type and monomeric IgA1-type antibodies may neutralize influenza viruses

| | A/H5N1 (clade 2.1) | | A/H1N1 | |
| --- | --- | --- | --- | --- |
| Clone names | Minimum neutralization concentration of monomeric IgG1 type (µg/mL) | Minimum neutralization concentration of monomeric IgA1 type (µg/mL) | Minimum neutralization concentration of monomeric IgG1 type (µg/mL) | Minimum neutralization concentration of monomeric IgA1 type (µg/mL) |
| G2 | >250 | — | >250 | — |
| H10 | >250 | — | 250 | — |
| D11 | >250 | >250 | 250 | >250 |
| F9 | >250 | >250 | 250 | 15.6 |
| F11 | 250 | 125 | 0.98 | 0.98 |
| H5 | 250 | 62.5 | 125 | >250 |
| B12 | >250 | >250 | >250 | >250 |
| C1 | >250 | — | >125 | — |

(Influenza Virus-Neutralizing Activity of Dimeric IgA1-Type Recombinant Antibody)

The influenza virus-neutralizing activity was measured in the same manner as described above using the monomeric and dimeric IgA1-type antibodies of the antibody clones D11, F9, F11, H5 and B12. An A/H5N1 strain (clade 2.1) and an A/H1N1 strain were used as the viruses.

The results are listed in Table 2. It meant that the lower the minimum neutralization concentration was, the higher the virus-neutralizing activity was. In spite of the same structure of the variable regions of the antibodies, the dimeric antibodies tended to have higher virus-neutralizing activity than the monomeric antibodies.

TABLE 2

Minimum antibody concentration (minimum neutralization concentration) at which clones of each of monomeric and dimeric IgA1-type antibodies may neutralize influenza viruses

| | A/H5N1 (clade 2.1) | | A/H1N1 | |
|---|---|---|---|---|
| Clone names | Minimum neutralization concentration of monomeric IgA1 type (μg/mL) | Minimum neutralization concentration of dimeric IgA1 type (μg/mL) | Minimum neutralization concentration of monomeric IgA1 type (μg/mL) | Minimum neutralization concentration of dimeric IgA1 type (μg/mL) |
| D11 | >250 | 250 | 31.3 | 15.6 |
| F9 | >100 | >250 | >100 | >250 |
| F11 | >250 | 15.6 | 7.8 | 0.98 |
| H5 | >125 | 125 | >125 | >250 |
| B12 | >250 | >250 | 125 | 62.5 |

(Influenza Virus-Neutralizing Activity of Tetrameric IgA1-Type Recombinant Antibody)

The influenza virus-neutralizing activity was measured in the same manner as described above using the monomeric, dimeric and tetrameric IgA1-type antibodies of the antibody clones F9, F11 and H5. An A/H5N1 strain (clade 2.1) was used as the virus. The results are listed in Table 3. It meant that the lower the minimum neutralization concentration was, the higher the virus-neutralizing activity was.

In spite of the same structure of the variable regions of the antibodies, the dimeric antibodies tended to have higher virus-neutralizing activity than the monomeric antibodies, and the tetrameric antibodies tended to have higher virus-neutralizing activity than the dimeric antibodies.

TABLE 3

Minimum antibody concentration (minimum neutralization concentration) at which clones of each of monomeric, dimeric and tetrameric IgA1-type antibodies may neutralize influenza viruses

| | A/H5N1 (clade 2.1) | | |
|---|---|---|---|
| Clone names | Minimum neutralization concentration of monomeric IgA1 type (μg/mL) | Minimum neutralization concentration of dimeric IgA1 type (μg/mL) | Minimum neutralization concentration of tetrameric IgA1 type (μg/mL) |
| F9 | >125 | >125 | >125 |
| F11 | >125 | 15.6 | 7.8 |
| H5 | 90 | 15.6 | 3.9 |

(Increase in Influenza Virus-Neutralizing Activity Through Polymerization)

To compare the activities of the neutralizing abilities of the monomeric IgG1-type antibody, the monomeric IgA1-type antibody, the dimeric IgA1-type antibody, and the tetrameric IgA1-type antibody for the antibody clones F11 and H5, the neutralizing activity ratios of the monomeric IgA1-type antibody, the dimeric IgA1-type antibody and the tetrameric IgA1-type antibody were indicated when it was assumed that the virus-neutralizing activity of the monomeric IgG1-type antibody was set to 1 as shown in FIGS. 5A and 5B. An A/H5N1 strain (clade 2.1) was used as the virus.

FIG. 5A is a graph illustrating the neutralizing activity ratios of the monomeric IgA1-type antibody, the dimeric IgA1-type antibody, and the tetrameric IgA1-type antibody per unit amount of proteins when it is assumed that the virus-neutralizing activity of the monomeric IgG1-type antibody is set to 1.

FIG. 5B is a graph illustrating the neutralizing activity ratios of the monomeric IgA1-type antibody, the dimeric IgA1-type antibody, and the tetrameric IgA1-type antibody per unit number of molecules when it is assumed that the virus-neutralizing activity of the monomeric IgG1-type antibody is set to 1.

In both of the clones F11 and H5, an increase in the virus-neutralizing activity was observed when the clones F11 and H5 were converted from IgG1 types into IgA1 types, and a further increase in the neutralizing activity was observed through dimerization and tetramerization. Also, the virus-neutralizing activity per 1 mole of antibody was observed to increase to 100-fold or more of the monomer through tetramerization.

Experimental Example 6: Analysis of Base Sequences and Amino Acid Sequences of Antibodies Base sequences and amino acid sequences of heavy chains and light chains for the antibody clones F11 and H5 were analyzed using IgBLAST (http://www.ncbi.nlm.nih.gov/igblast/). Also, the complementarity determining regions (CDRs) were determined using the method by Dr. Andrew C. R. Martin (http://www.bioinf.org.uk/abs/). The correspondences between the sequence numbers in the sequence listing and the respective base sequences and amino acid sequences are listed in Table 4. The light chain of the clone F11 was a κ chain. Also, the light chain of the clone H5 was a λ chain.

TABLE 4

Table of correspondences of base sequences and amino acid sequences of respective antibody clones

| SEQ ID NO: | Clones | Notes | |
|---|---|---|---|
| 1 | F11 | Heavy chain CDR-H1 | Amino acid sequence |
| 2 | F11 | Heavy chain CDR-H2 | Amino acid sequence |
| 3 | F11 | Heavy chain CDR-H3 | Amino acid sequence |
| 4 | F11 | Light chain CDR-L1 | Amino acid sequence |
| 5 | F11 | Light chain CDR-L2 | Amino acid sequence |
| 6 | F11 | Light chain CDR-L3 | Amino acid sequence |
| 7 | F11 | Heavy chain variable region | Amino acid sequence |
| 8 | F11 | Light chain variable region | Amino acid sequence |
| 9 | H5 | Heavy chain CDR-H1 | Amino acid sequence |
| 10 | H5 | Heavy chain CDR-H2 | Amino acid sequence |
| 11 | H5 | Heavy chain CDR-H3 | Amino acid sequence |
| 12 | H5 | Light chain CDR-L1 | Amino acid sequence |
| 13 | H5 | Light chain CDR-L2 | Amino acid sequence |
| 14 | H5 | Light chain CDR-L3 | Amino acid sequence |
| 15 | H5 | Heavy chain variable region | Amino acid sequence |
| 16 | H5 | Light chain variable region | Amino acid sequence |
| 17 | F11 | Heavy chain variable region | Base sequence |
| 18 | F11 | Light chain variable region | Base sequence |
| 19 | H5 | Heavy chain variable region | Base sequence |
| 20 | H5 | Light chain variable region | Base sequence |

Experimental Example 7: Examination of Antigen-Binding Activity

Preparation of a recombinant viral glycoprotein expression vector, and expression and purification of a recombinant viral glycoprotein were performed in the same manner as in Experimental Example 9 as will be described later. The antigen-binding activity against an influenza virus HA protein was examined for the antibody clones B12 and F11 using the monomeric IgA1-type antibody, the dimeric IgA1-type antibody, and the tetrameric IgA1-type antibody.

50 µL of a recombinant HA protein (1 µg/mL, derived from an A/H5N1 strain) was added to a 96-well half plate, stationarily incubated at 4° C. overnight, and then blocked.

Next, two-fold serial dilutions of each antibody sample were reacted overnight at 4° C. After being washed with PBST, the Goat anti-Human IgA Antibody Alkaline Phosphatase Conjugated (BETHYL LABORATORIES), which had been diluted to 2,500 times, were reacted at room temperature for an hour. Subsequently, a chromogenic reaction was performed using a phosphatase substrate (SIGMA), and the absorbance at a wavelength of 405 nm was measured using a wavelength of 690 nm as a reference wavelength. Based on the measured absorbance, the minimum binding concentration of each of the antibodies to the HA protein was determined.

The results are listed in Tables 5 and 6. In the antibody clone F11, an increase in binding activity to HA derived from the viruses (A/H5N1 (clade 2.1)) in the same clade as the vaccines (clade 2.1) was observed in the dimers and tetramers, compared to the monomers. Also, the strongest antigen-binding activity to HA derived from viruses (A/H5N1 (clade 1)) in the different clade as the vaccine was observed in the tetramers.

In addition, it was revealed that the clones having antigen binding activity in the monomeric antibodies had improved antigen binding activity through polymerization.

TABLE 5

Minimum antibody concentration (minimum binding concentration) at which clones of each of monomeric, dimeric and tetrameric IgA1-type antibodies may bind to influenza virus HA (A/H5N1 (clade 2.1)

| | A/H5N1 (clade 2.1) | | |
|---|---|---|---|
| Clone names | Minimum binding concentration of monomeric IgA1 type (µg/mL) | Minimum binding concentration of dimeric IgA1 type (µg/mL) | Minimum binding concentration of tetrameric IgA1 type (µg/mL) |
| B12 | >100 | >100 | 100 |
| F11 | 1 | 0.06 | 0.06 |

TABLE 6

Minimum antibody concentration (minimum binding concentration) at which clones of each of monomeric, dimeric and tetrameric IgA1-type antibodies may bind to influenza virus HA(A/H5N1 (clade 1))

| | A/H5N1 (clade 1) | | |
|---|---|---|---|
| Clone names | Minimum binding concentration of monomeric IgA1 type (µg/mL) | Minimum binding concentration of dimeric IgA1 type (µg/mL) | Minimum binding concentration of tetrameric IgA1 type (µg/mL) |
| B12 | >100 | >100 | >100 |
| F11 | >5 | 0.63 | 0.31 |

Experimental Example 8: Expression-Enhancing Effect of Polymeric Antibodies Using CHO YA7 Cells and Cis-Element Cis-element #1 set forth in SEQ ID NO: 22 was introduced downstream from a promoter of pCXSN-hJC which was an expression plasmid for the above-described antibody J chain protein and upstream from an initiation codon of the J chain protein to obtain pCXSN-cis#1-hJC. Based on the genetic sequence analysis, it was confirmed that the cis-element was inserted in the correct direction.

Also, cis-element #2 set forth in SEQ ID NO: 23 was introduced downstream from a promoter of pCXSN-hSC which was an expression plasmid for the above-described secretory component and upstream from an initiation codon of the secretory component protein to obtain pCXSN-cis#2-hSC. Based on the genetic sequence analysis, it was confirmed that the cis-element was inserted in the correct direction.

$1 \times 10^5$ CHO YA7 cells, which are a cell line coexpressing the p180 protein and the SF3b4 protein, and $1 \times 10^5$ control CHO cells were transfected with 0.5 µg of each of four expression plasmids, for example, the IgA1 antibody heavy chain expression plasmid and the full-length light chain expression plasmid, both of which were constructed in Experimental Example 2, pCXSN-cis#1-hJC, and pCXSN-cis#2-hSC, using a lipofection method.

After both of the cells were cultured for 24 hours in a DMEM medium containing 0.5 mL of 5% fetal bovine serum, 10 µL of each of the culture supernatants was isolated on BN-PAGE in the same manner as in Experimental Example 3, and transferred to a PVDF membrane, and then detected with a peroxidase-labeled anti-human IgA antibody (Bethyl Co.) to evaluate an ability to produce a polymeric IgA-type antibody.

Figure 6:
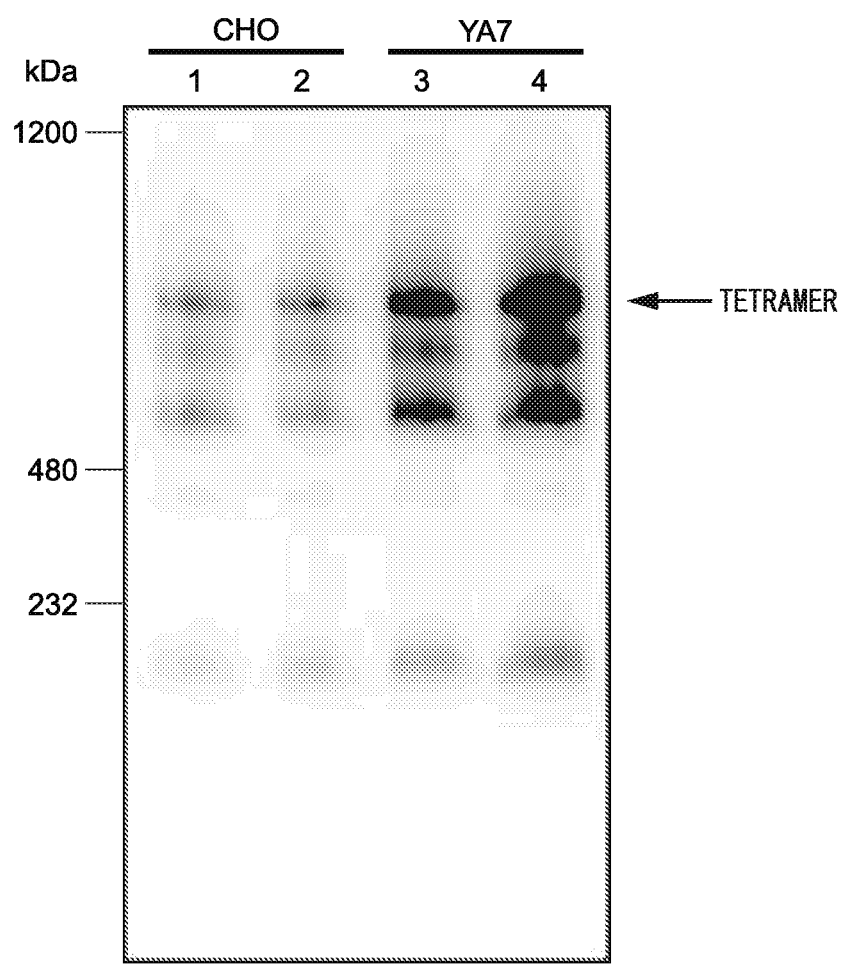
FIG. 6 is an image showing results of blue native polyacrylamide gel electrophoresis (BN-PAGE) to check an expression-enhancing effect of a polymeric antibody using CHO YA7 cells and a cis-element.

FIG. 6 is an image showing results of the BN-PAGE. Lanes 1 and 2 show the results of expressing the polymeric IgA-type antibody in the CHO cells, and lanes 3 and 4 show the results of expressing the polymeric IgA-type antibody in the CHO YA7 cells. Also, lanes 1 and 3 show the results obtained using the expression plasmid for the antibody J-chain protein having no cis-element, and the expression plasmid for the secretory component having no cis-elements as the controls, and lanes 2 and 4 show the results obtained using the expression plasmid for the antibody J-chain protein having the cis-element, and the expression plasmid for the secretory component having the cis-element. An arrow indicates a band of the tetrameric IgA-type antibody.

As a result, it was revealed that a secretion level of the polymeric IgA-type antibody in the CHO YA7 cells increased to approximately twice that of the CHO cells when the expression plasmid having no cis-element was used. Also, it was revealed that the secretion level of the polymeric IgA-type antibody in the CHO YA7 cells increased to 3.2 times that of the CHO cells when the expression plasmid having the cis-element was used.

The above-described results show that the polymeric IgA-type antibody can be expressed and secreted with high efficiency by coexpressing the p180 protein and the SF3b4 protein or using the expression plasmid having the cis-element.

Experimental Example 9: Examination of Effect of Polymerization on Binding Activity of Anti-RS Virus F Protein Antibody (Preparation of Anti-RS Virus F Protein Antibody)

DNA fragments coding for amino acid sequences, in which the amino acid sequences of the heavy chain and light chain variable regions of the amino acid sequence (PDB ID: 2HWZ) of the anti-RS virus F protein antibody registered in the public database RCSB PDB were codon-optimized for human beings, were artificially synthesized. The DNA fragment coding for the synthesized heavy chain variable region was cloned into the above-described α1 HC, and the DNA fragment coding for the light chain variable region was cloned into the above-described κ LC. Subsequently, the polymer of the anti-RS virus F protein antibody was expressed and purified in the same manner as in Experimental Example 4.

(Preparation of Viral Glycoprotein Expression Vector)

A DNA fragment coding for an amino acid sequence, in which a trimerization sequence and a coding sequence of a tag for purification (a foldon sequence for trimerization of bacteriophage T4 fibritin, a thrombin cleavage site (RSRSLVPRGSPGSGYIPEAPRDGQAYVRKDGEWV-LLSTFL, SEQ ID NO: 26), a Strep-tag (registered trademark) II sequence for purifications of proteins (WSHPQFEK, SEQ ID NO: 27), and a 6×His tag sequence (see Stevens J. et al., Structure of the uncleaved human H1 hemagglutinin from the extinct 1918 influenza virus., Science 303, 1866-1870, 2004)) were fused to the C-terminal sides of the amino acid sequences coding for extracellular regions of the influenza virus HA protein and the RS virus F protein ΔFP (a variant in which amino acid sequences at positions 137 to 146 are deleted; see McLellan J. S. et al., Structure of respiratory syncytial virus fusion glycoprotein in the postfusion conformation reveals preservation of neutralizing epitopes, J. Virol. 85(15), 7788-7796, 2011), was synthesized, and cloned into a vector pCXSN for expressing mammalian cells.

(Expression of Viral Glycoprotein)

An Expi293 (trademark) expression system (Life Technologies Inc.) was used according to the instructions to produce a recombinant viral glycoprotein. As one example, a 30 mL system will be described below.

It was confirmed that Expi293F cells subcultured had a density of more than $3.0 \times 10^6$ cells/mL and survival rate of more than 95%, and the cells were not aggregated. The number of cells was adjusted to $2.9 \times 10^6$ cells/mL using an Expi293 expression medium warmed at 37° C. 25.5 mL of the prepared cell suspension was transferred to a disposable Erlenmeyer flask equipped with a vent filter cap, returned to an incubator for cell culture set to 37° C. and 8% $CO_2$, and cultured by shaking at 125 rpm. 30 µg of plasmid DNA was added to 1.5 mL of an Opti-MEM I medium. 80 µL of an ExpiFectamine 293 reagent was added to 1.5 mL of a separately prepared Opti-MEM I medium. After a DNA solution and an ExpiFectamin soultion were incubated at room temperature for 5 minutes, a total volume of the DNA solution was added to an ExpiFectamine solution, and then incubated at room temperature for 20 to 30 minutes. After a transfection mix was added to the cells, the cells were returned to an incubator for cell culture set to 37° C. and 8% $CO_2$, and cultured by shaking at 125 rpm. After 16 to 18 hours of transfection, 150 µL of ExpiFectamine 293 Transfection Enhancer 1 and 1.5 mL of ExpiFectamine 293 Transfection Enhancer 2 were added. The cells were returned to an incubator for cell culture set to 37° C. and 8% $CO_2$, and cultured by shaking at 125 rpm. A supernatant was collected after 4 to 6 days of the transfection.

(Purification of Viral Glycoprotein)

First, debris of the cells in the collected supernatant was removed by centrifugation at 1,000×g for 10 minutes. Thereafter, the supernatant was filtered with a Millex-HV filter unit (Millipore Corporation). Subsequently, a viral glycoprotein was purified via affinity purification using AKTA explorer 10 (GE Healthcare). HisTrap excel (GE Healthcare) was used as the column. More specifically, 20 mM sodium phosphate, and 0.5M NaCl (pH 7.4) were used as an equilibration solution. Also, 20 mM sodium phosphate, 0.5M NaCl, and 10 mM imidazole (pH 7.4) were used as a washing solution. Also, 20 mM sodium phosphate, 0.5M NaCl, and 500 mM imidazole (pH 7.4) were used as an eluent. The purification conditions were as follows: a flow rate of 1 mL/min, column equilibration at 10 CV, column washing at 40 CV, elution at 1 mL/fraction (a total of 50 CV), and column re-equilibration at 5 CV. A Strep-tag (registered trademark)/Strep-Tactin (registered trademark) system was used to further purify the sample purified with the 6×His tag. The sample was purified according to the instructions using Strep-Tactin (registered trademark) Superflow (registered trademark) (IBA). More specifically, first, Buffer W (100 mM Tris-HCl, 150 mM NaCl, and 1 mM EDTA, pH 8.0), Buffer E (100 mM Tris-HCl, 150 mM NaCl, 1 mM EDTA, and 2.5 mM desthiobiotin, pH 8.0), and Buffer R (100 mM Tris-HCl, 150 mM NaCl, 1 mM EDTA, and 1 mM HABA, pH 8.0) were prepared as reagents. Subsequently, the column was equilibrated with 2 CV of the Buffer W, loaded with the sample, and washed 5 times with 1 CV of the Buffer W. Thereafter, the viral glycoprotein was eluted with 3 CV of the Buffer E. For regeneration, the column was then washed three times with 5 CV of the Buffer R, and equilibrated twice with 4 CV of the Buffer W. When the protein was concentrated, the protein was concentrated according to the instructions using an Amicon (registered trademark) ultra-centrifugal filter device. The concentration of the purified protein was determined by measuring the absorbance using NanoDrop (Thermo Scientific Ltd.).

(ELISA for RS Virus F Protein)

Figure 7:
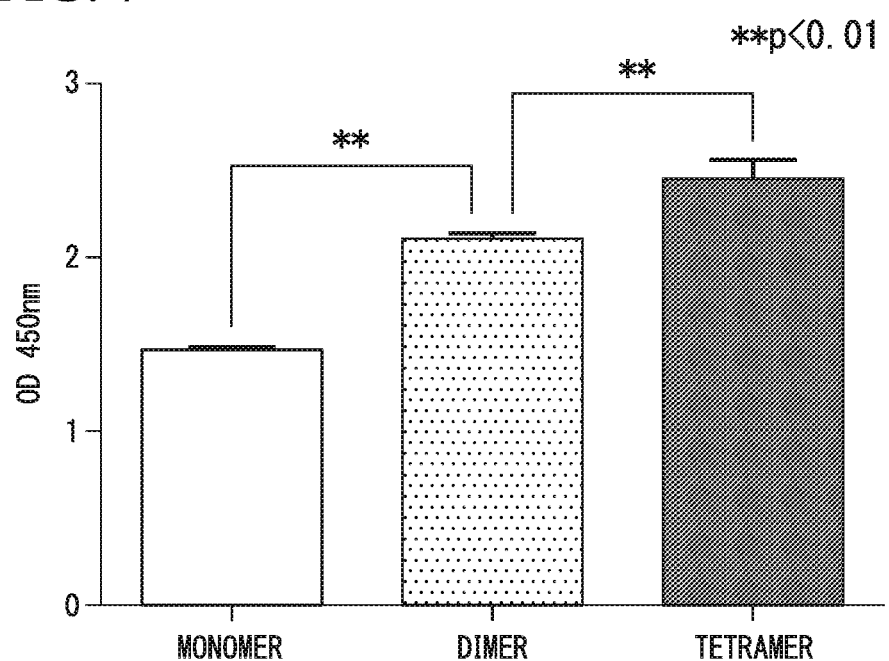
FIG. 7 is a graph illustrating results of Experimental Example 9.

Reactivity of a polymer of the anti-RS virus F protein antibody was examined using ELISA. First, 50 μL of a recombinant F protein (1 μg/mL) was immobilized on a 96-well half plate overnight at 4° C., and then blocked. Thereafter, two-fold serial dilutions of the anti-RS virus F protein antibody sample were reacted at room temperature for 2 hours. Subsequently, after the antibody sample was washed with PBST, an HRP-labeled goat anti-human IgA antibody (30,000 times) (BETHYL LABORATORIES) was reacted at room temperature for an hour. Then, a color reaction was performed using 1-Step (trademark) Ultra TMB-ELISA (Thermo Scientific Ltd.), 1M sulfuric acid was added to quench the reaction, and the absorbance was measured. The value at OD 450 nm (a mean valucistandard deviation) for the anti-RS virus F protein antibody sample at a concentration of 1 μg/mL is shown in FIG. 7. As a result, it was confirmed that the antigen-binding activity of the anti-RS virus F protein antibody significantly increased when the antibody was dimerized or tetramerized.

Experimental Example 10: Examination of Polymerization of IgA1 and Respective IgA2 Allotypes (Preparation of α2m1 HC, α2m2 HC and α2(n) HC Expression Vectors)

Genes of heavy chain constant regions of IgA2 allotypes were cloned. Specifically, a base sequence of each of a gene coding for a heavy chain constant region of IgA2m1 (α2m1 HC; accession no.: J00221), a gene coding for a heavy chain constant region of IgA2m2 (α2m2 HC; accession no.: M60192 and AJ012264), and a gene coding for a heavy chain constant region of IgA2(n) (α2(n) HC; accession no.: S71043) was obtained, codon-optimized for human beings, and then artificially synthesized based on the sequences registered in the public database IMGT/LIGM-DB. Codons for the last amino acid, alanine, of the variable region and the first amino acid, serine, of the constant region were changed to form a NheI cleavage site. The synthetic sequence digested with NheI and HindIII was cloned into a vector in which the above-described α1 HC had been digested with NheI and HindIII.

(Cloning of Antibody Variable Region Genes into Respective IgA2 Expression Vectors)

The antibody variable region gene of the above-described anti-influenza virus antibody clone B12 was subjected to PCR using PrimeSTAR (registered trademark) MAX DNA Polymerase. When the antibody gene cloned into a γ1 HC expression vector was used as a template, the same method as the cloning of the antibody gene into the α1 HC expression vector was used. When the antibody gene cloned into the α1 HC expression vector was used, a subcloning method using conventional restriction enzymes such as AgeI and NheI was used.

Subsequently, polymers of the anti-influenza antibody clone B12 of an IgA1 type and respective IgA2 allotypes were expressed and purified in the same manner as in Experimental Example 4.

(Analysis of Polymer Using Size Exclusion Chromatography)

Figure 8A:
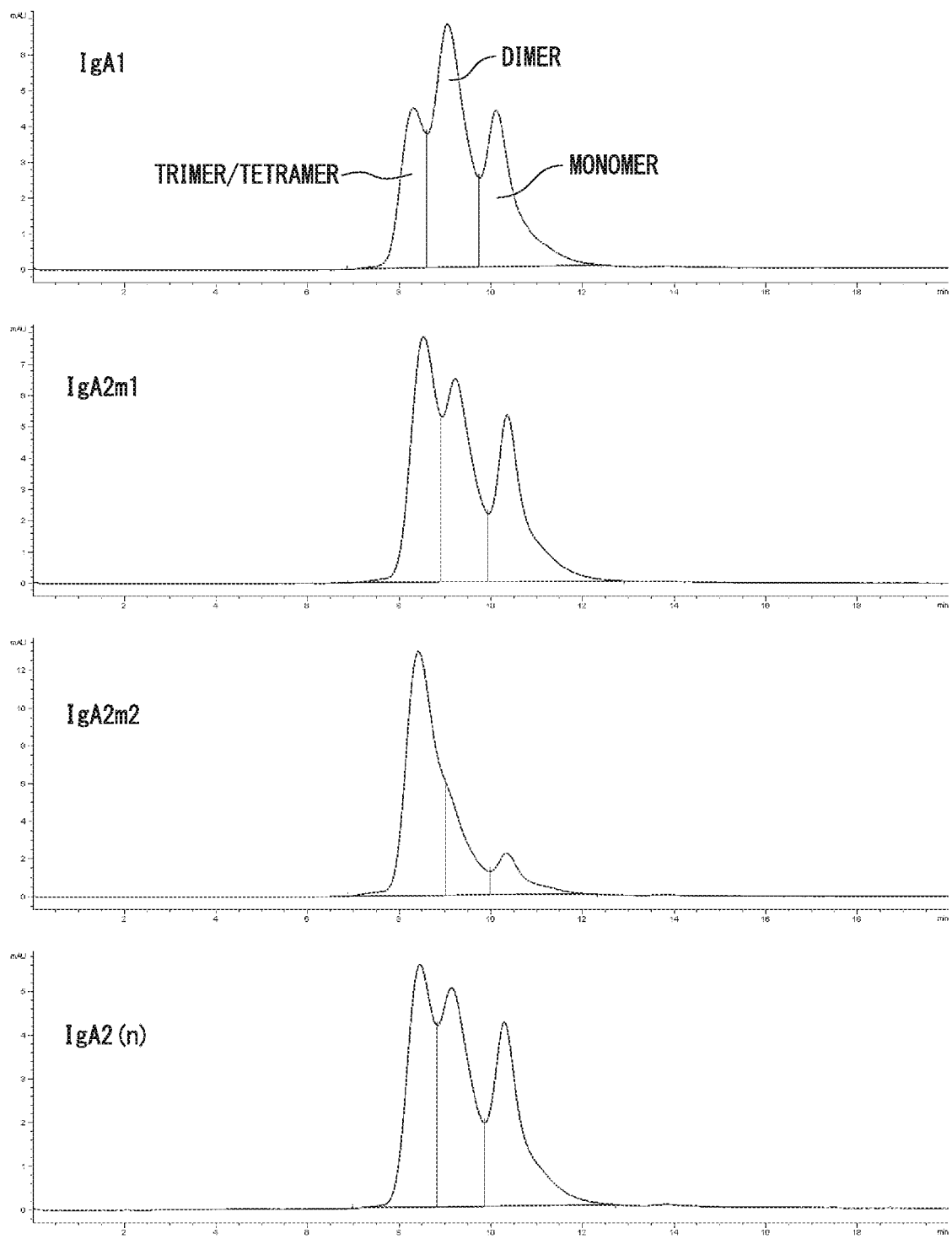
FIG. 8A is a graph illustrating results of Experimental Example 10.
Figure 8B:
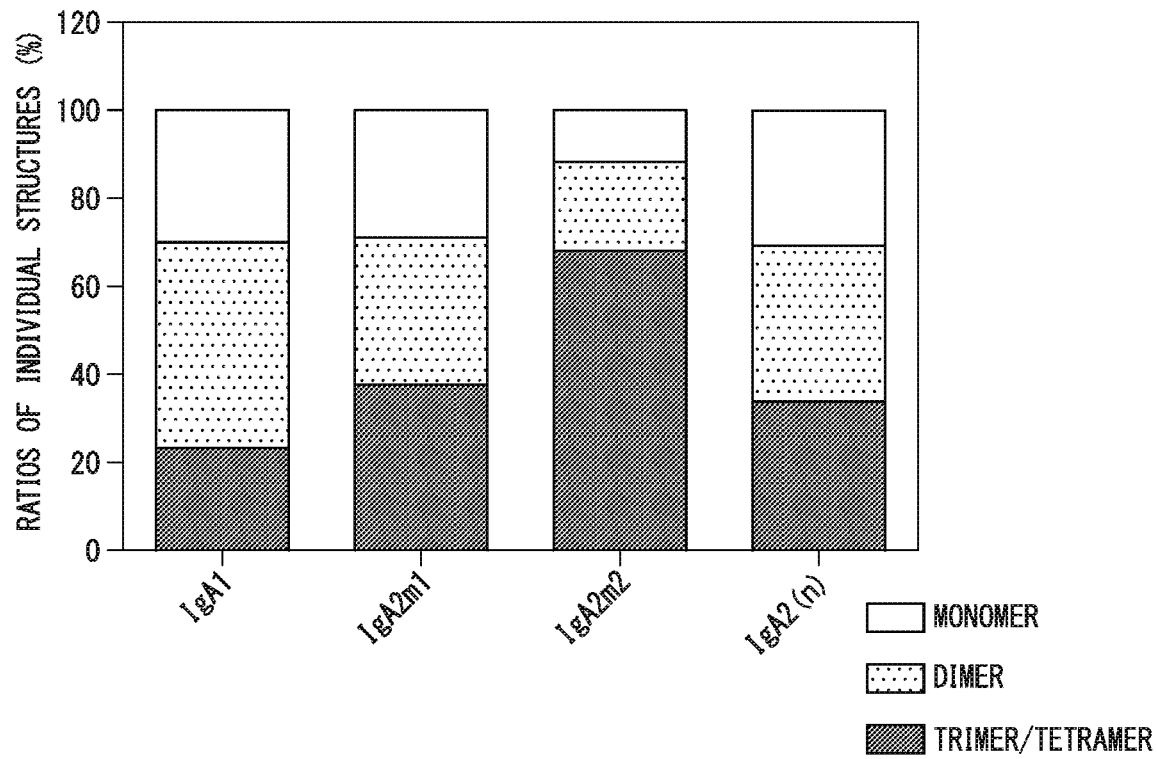
FIG. 8B is a graph illustrating results of Experimental Example 10.

Samples were pretreated with Cosmo spin filter H (Nacalai Tesque, Inc.), and separated based on the molecular size using size exclusion chromatography, and the structures of the antibodies were analyzed. Agilent 1260 Infinity (Agilent Technologies) was used as the HPLC system. Also, Agilent Bio SEC-5 500 Å (Agilent Technologies) was used as the column. PBS (pH 7.4) was used as an eluent, and an elution was performed at a flow rate of 1 mL/min. One μg or more of an antibody sample was used per analysis. Chromatograms were analyzed using OpenLAB CDS ChemStation Edition (Agilent Technologies) to calculate areas of peaks corresponding to trimers/tetramers, dimers, and monomers, and the peak areas were compared as area ratios. FIG. 8A shows representative results of the IgA1-type, IgA2m1-type, IgA2m2-type, and IgA2(n)-type antibodies on the chromatogram obtained by size exclusion chromatography. FIG. 8B is a graph illustrating results of calculating peak area ratios of the trimeric/tetrameric, dimeric, and monomeric antibodies based on the results of FIG. 8A. When valleys between the peaks shown in FIG. 8A was clear, a vertical line was drawn from local minimum point to the baseline in order to sort the respective fractions, and an area surrounded with the chromatogram, the vertical line and the baseline was calculated. When valleys between the peaks or separation of the peaks on the chromatogram shown in FIG. 8A was unclear, an inflection point of each of the peaks was inferred, a vertical line was drawn to the baseline in order to sort the respective fractions, and an area surrounded with the chromatogram, the vertical line and the baseline was calculated.

As a result, it was revealed that all the IgA isotypes and allotypes (IgA1, IgA2m1, IgA2m2, and IgA2(n)) reported so far could form polymers. Also, it was found that the IgA1 and respective IgA2 allotypes had different tendencies to be polymerized. In particular, it was revealed that the IgA2m2-type antibody had a high ability to form a polymer.

Experimental Example 11: Examination of Polymerization of Chimeric Antibody of IgA1-Type Antibody and IgA2m2-Type Antibody To analyze an activity of the IgA2m2-type antibody to promote polymerization, the following analysis was performed.

(Preparation of α1α2m2 Chimeric HC Expression Vector)

A sequence spanning from CH1 to CH2 of IgA1 HC (an α1 segment: spanning from the N-terminus of the constant region to G342) was PCR-amplified using a PrimeSTAR (registered trademark) MAX DNA Polymerase and the above-described α1 HC expression vector as a template. Also, a sequence spanning from CH3 to the C-terminus of IgA2m2 HC (an α2m2 segment: spanning from N343 to the C-terminus of the constant region) was PCR-amplified using the α2m2 HC expression vector as a template.

Subsequently, Overlap PCR using the α1 segment and the α2m2 segment as templates was performed using KOD-Plus-Neo (TOYOBO). Thereafter, the resulting DNA fragment was exchanged with the sequence of the constant region of α1 HC by a subcloning method using NheI and HindIII to obtain an IgA1A2m2 chimeric expression vector.

Subsequently, a variable region of the anti-influenza virus antibody clone B12 was cloned into the IgA1A2m2 chimeric HC expression vector in the same manner as in Experimental Example 10. Also, the polymeric antibody was expressed and purified in the same manner as in Experimental Example 4. In addition, the abundance ratios of the antibodies having monomeric, dimeric, trimeric/tetrameric structures were analyzed using size exclusion chromatography in the same manner as in Experimental Example 10.

Figure 9:
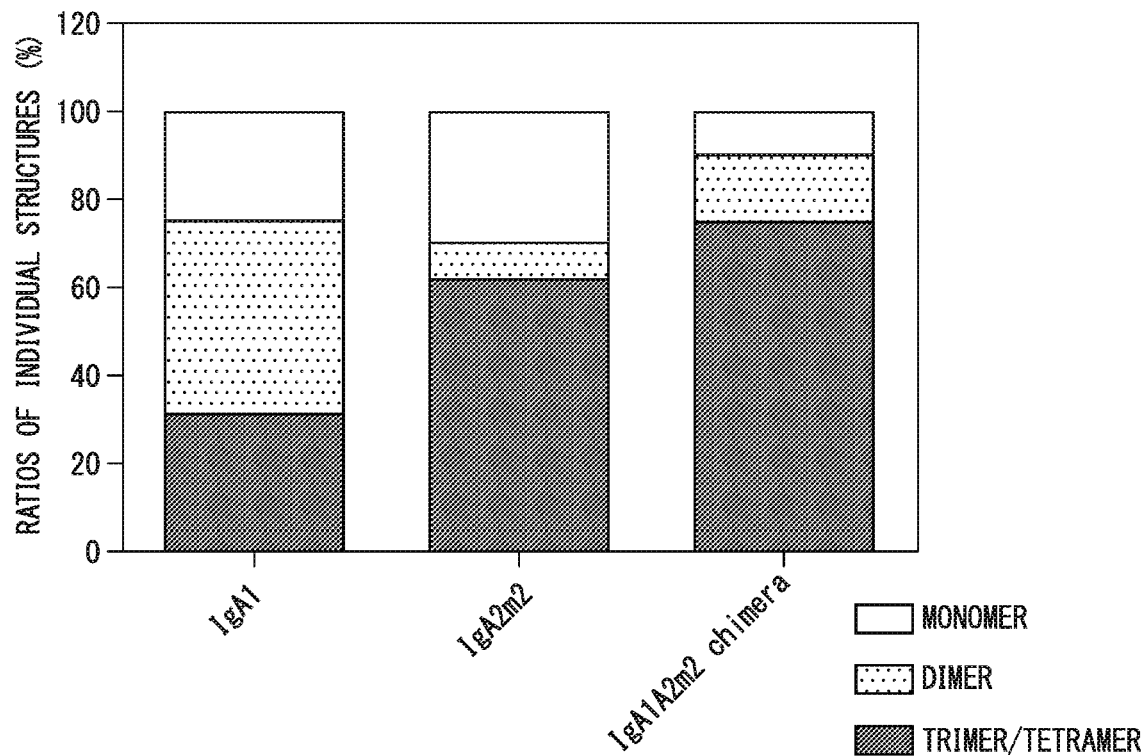
FIG. 9 is a graph illustrating results of Experimental Example 11.

FIG. 9 is a graph illustrating the results. As a result, it was revealed that the polymerization was promoted when the sequence spanning from the CH3 to the C-terminus of the heavy chain of the IgA1 antibody was exchanged with the IgA2m2-derived sequence.

Example 12: Analysis of Region Involved in Polymerization-Promoting Activity of IgA2m2

To analyze the polymerization-promoting activity of IgA2m2, various expression vectors were constructed, as follows.

(Construction of IgA Heavy Chain Constant Region-Modified Expression Vector)

To construct a mutant expression vector with the IgA heavy chain constant region, the fragments IgA1 H-NRE (SEQ ID NO: 28) and IgA2m2-NRE (SEQ ID NO: 29) of the constant region in which a restriction enzyme site was added to have no amino acid substitutions in the constant region were synthesized via artificial gene synthesis (Genscript). Thereafter, the IgA1H-NRE and IgA2m2-NRE were digested with restriction enzymes NheI and HindIII to prepare fragments for ligation.

Next, the expression plasmid (pIgA1H) of the IgA1-type heavy chain of the above-described anti-influenza virus antibody clone B12, and the expression plasmid (pIgA2m2H) of the IgA2m2-type heavy chain of the anti-influenza virus antibody clone B12 were digested with the restriction enzymes NheI and HindIII to prepare fragments for ligation in the same manner. The respective fragments were ligated to prepare plasmids pIgA1H-NRE and pIgA2m2H-NRE.

(Construction of IgA1/IgA2m2 Chimeric Heavy Chain Expression Vector)

Figure 10A:
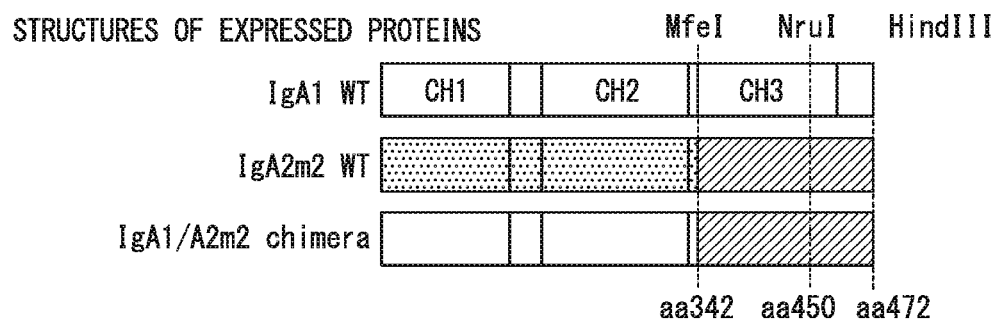
FIG. 10A is a schematic diagram showing structures of IgA antibody variants.

The IgA1/IgA2m2 chimeric heavy chain expression vector was constructed as follows. A fragment obtained by digesting pIgA2m2H-NRE with MfeI and HindIII was ligated to pIgA1H-NRE digested with MfeI and HindIII to construct a mutant pIgA1H/pIgA2m2-chimera in which a region of amino acids at positions 342 to 472 of the heavy chain of IgA1 was replaced with an IgA2m2 type. FIG. 10A is a schematic diagram showing the structures of the respective mutants.

(Construction of J/SC Stably Expressing Strain and Verification of IgA Polymer-Producing Ability)

To construct an expression vector for coexpressing the J chain and SC, cis#1-hJC ORF and cis#2-hSC ORF were excised from the pCXSN-cis#1-hJC and pCXSN-cis#2-hSC prepared in Example 5. The cis#1-hJC ORF and cis#2-hSC ORF were ligated between a promoter and poly A in an expression unit consisting of a human EF1 promoter and BGH polyA to construct expression vectors pEF-cis-hJC/Zeo and pEF/cis-hSC/Zeo, respectively.

Also, to construct vectors expressing mutants in which asparagine (N) to which an N-linked sugar chain covalently attached was substituted with glutamine (Q) for each of the J chain and SC proteins (hereinafter referred to as "$J_{NQ}$" and "$SC_{NQ}$," respectively), fragments coding for $J_{NQ}$ and $SC_{NQ}$ were prepared by artificial gene synthesis (Genscript) (SEQ ID NOs: 30 and 31). In the J chain, N59 was replaced with Q. Also, in the SC, N83, N90, N135, N186, N421, N469, and N499 were all replaced with Q. Subsequently, each of the synthesized fragments was digested with XhoI and NotI, and then ligated with the pCXSN-cis#1-hJC or pCXSN-cis#2-hSC digested with the same restriction enzymes XhoI and NotI, respectively, to construct pCXSN-cis#1-hJC$_{NQ}$ and pCXSN-cis#2-hSC$_{NQ}$.

Also, the expression vectors for p180 and SF3b4 were introduced into CHO-K1 cells according to the method disclosed in International Publication No. WO 2014/157429, and the drug selection using hygromycin was performed to prepare CHO-K1 cell line 1E26 stably expressing p180 and SF3b4. In this specification, a technique for enhancing gene expression by introducing an expression vector for two expression-enhancing factors (p180 and SF3b4) into cells is also referred to as the "spERt Technology."

The above-described pEF-cis-hJC/Zeo and pEF/cis-hSC/Zeo were introduced into CHO-K1 (1E26) cells, and drug selection was performed using Zeocin (400 μg/mL) to establish a CHO-K1 strain C23 stably expressing hJC and hSC. Similarly, the pCXSN-cis#1-hJC$_{NQ}$ and pCXSN-cis#2-hSC$_{NQ}$ were introduced into CHO-K1 (1E26) cells, and drug selection was performed using Zeocin (400 μg/mL) to establish a CHO-K1 strain C452 stably expressing hJC$_{NQ}$ and hSC$_{NQ}$.

Subsequently, C23 cells were transfected with the light chain expression vector (pIgA-LC) of the above-described anti-influenza virus antibody clone B12 and the IgA heavy chain expression vector of the anti-influenza virus antibody clone B12 using a lipofection method. The three above-described expression vectors (pIgA1H, pIgA2m2, and pIgA1H/pIgA2m2-chimera) were used as the IgA heavy chain expression vectors.

Subsequently, each of the cells was cultured for 72 hours in DMEM supplemented with 5% fetal bovine serum, and 10 μL each of the culture supernatants was then subjected to native polyacrylamide gel electrophoresis (BN-PAGE: 3-12%, Invitrogen) in the same manner as in Experimental Example 3 to separate proteins, and the separated proteins were transferred to a PVDF membrane, and then detected using a peroxidase-labeled anti-human IgA antibody (Bethyl Co.).

Figure 10B:
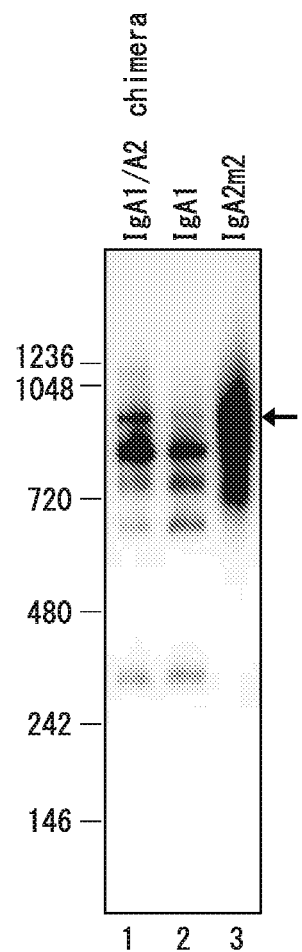
FIG. 10B is an image showing results of Experimental Example 12.

As a result, as shown in FIG. 10B, it was confirmed that the IgA1 polymer and the IgA2m2 polymer were detected in the culture supernatants of the C23 cells (FIG. 10B, Lanes 2 and 3, respectively), and the IgA polymeric antibody was able to be efficiently produced by introducing the genes of the heavy chain and light chain of the IgA antibody into the C23 cells.

Figure 16A:
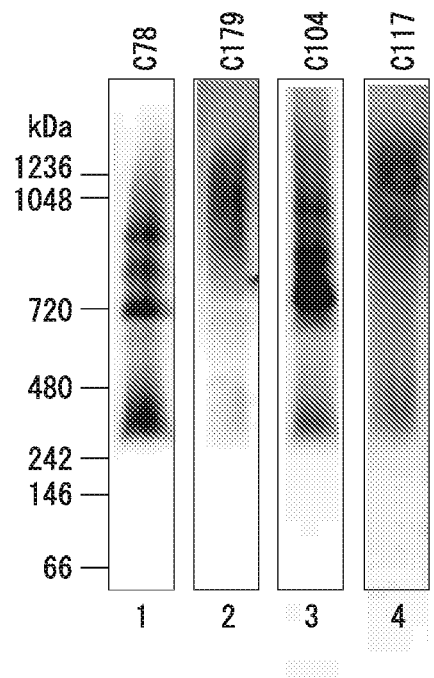
FIG. 16A is an image showing results of Experimental Example 18.
Figure 16B:
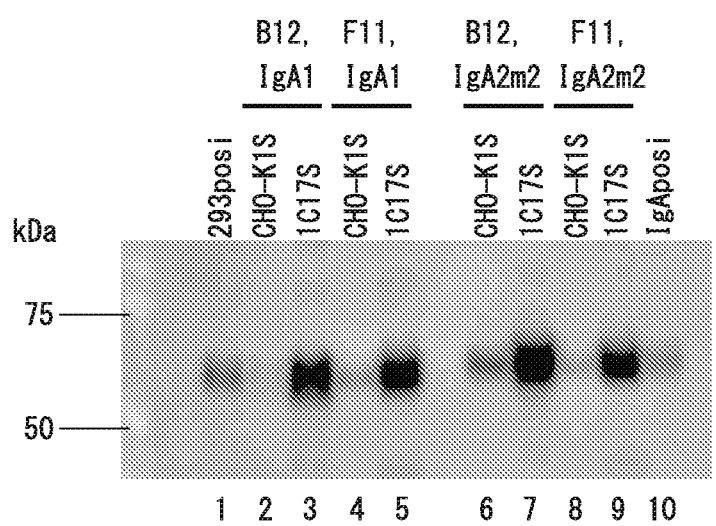
FIG. 16B is an image showing results of Experimental Example 19.
Figure 16C:
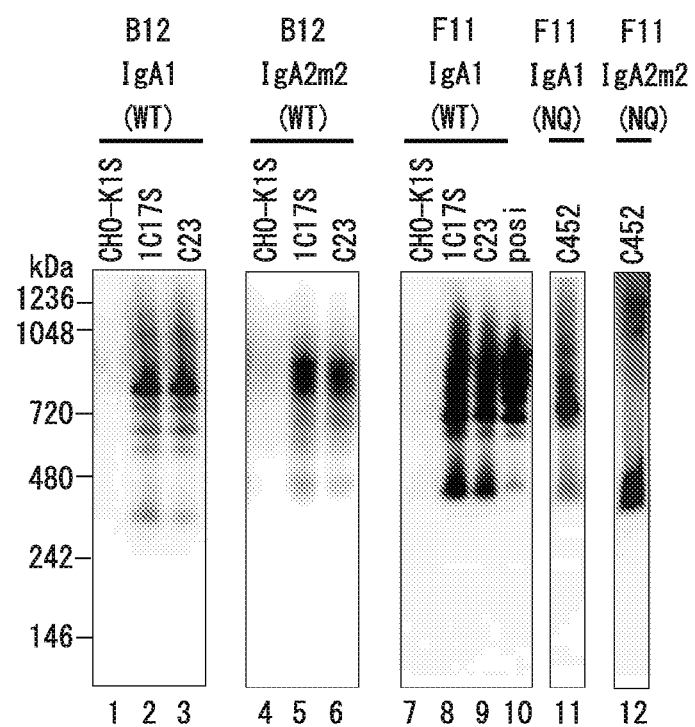
FIG. 16C is an image showing results of Experimental Example 19.

Also, as shown in Lanes 11 and 12 of FIG. 16C, the IgA1 polymer and the IgA2m2 polymer were detected in the culture supernatants, respectively, even in the same experiment conducted using the cells of the above-described anti-influenza virus antibody clones F11 and the C452 cells.

Based on the comparison of Lanes 2 and 3 in FIG. 10B, it was revealed that the IgA2m2 promoted polymerization, compared to the IgA1. Also, the pIgA1H/pIgA2m2 chimera increased a band shift toward a side of the polymer more than an IgA1 wild type (FIG. 10B, Arrow), and polymerization tendency like the IgA2m2 wild type was observed (FIG. 10B, Lane 1). Therefore, it was revealed that the C-terminal domain after the 342$^{nd}$ residue played an important role in polymerization of the IgA1 heavy chain, and that the polymerization was promoted in the CHO cells when the C-terminal domain was replaced with an IgA2m2-derived sequence.

Experimental Example 13: Examination of Polymerization of Single Amino Acid Substitution Mutants of IgA2m2 Antibody Since amino acid residues that differed between an amino acid sequence spanning from CH3 to the C-terminus of the IgA1 heavy chain and a corresponding amino acid sequence of the IgA2m2 heavy chain corresponding to the amino acid sequence were five residues: a 411$^{th}$ residue, a 428$^{th}$ residue, a 451$^{st}$ residue, a 458$^{th}$ residue, and a 467$^{th}$ residue, the following analysis was performed.

(Preparation of Amino Acid Substitution Mutants in Fc Region)

Mutants having an amino acid substitution in the constant region (Fc region) of the heavy chain were prepared. More specifically, inverse PCR was performed using an α2m2 HC expression vector as a template and using a PrimeSTAR (registered trademark) MAX DNA Polymerase and primers designed to introduce an amino acid substitution in the constant region (Fc region) of the heavy chain (Y411F, E428D, M451L, I458V, or A467V).

Subsequently, the 5'-terminus of the amplified PCR product was phosphorylated using a T4 polynucleotide kinase, and ligated in a circular form using a T4 DNA ligase. E. coli was transformed with the reaction product, and plasmids were extracted to check whether mutations causing the substitution of amino acids were introduced via sequencing.

Hereinafter, the prepared mutant is named "IgA2m2 Y411F." In this case, the amino acid tyrosine (Y) corresponding to the 411$^{th}$ residue in the constant region of IgA2m2 is replaced with phenylalanine (F). This nomenclature equally applies to the other mutants.

Figure 11:
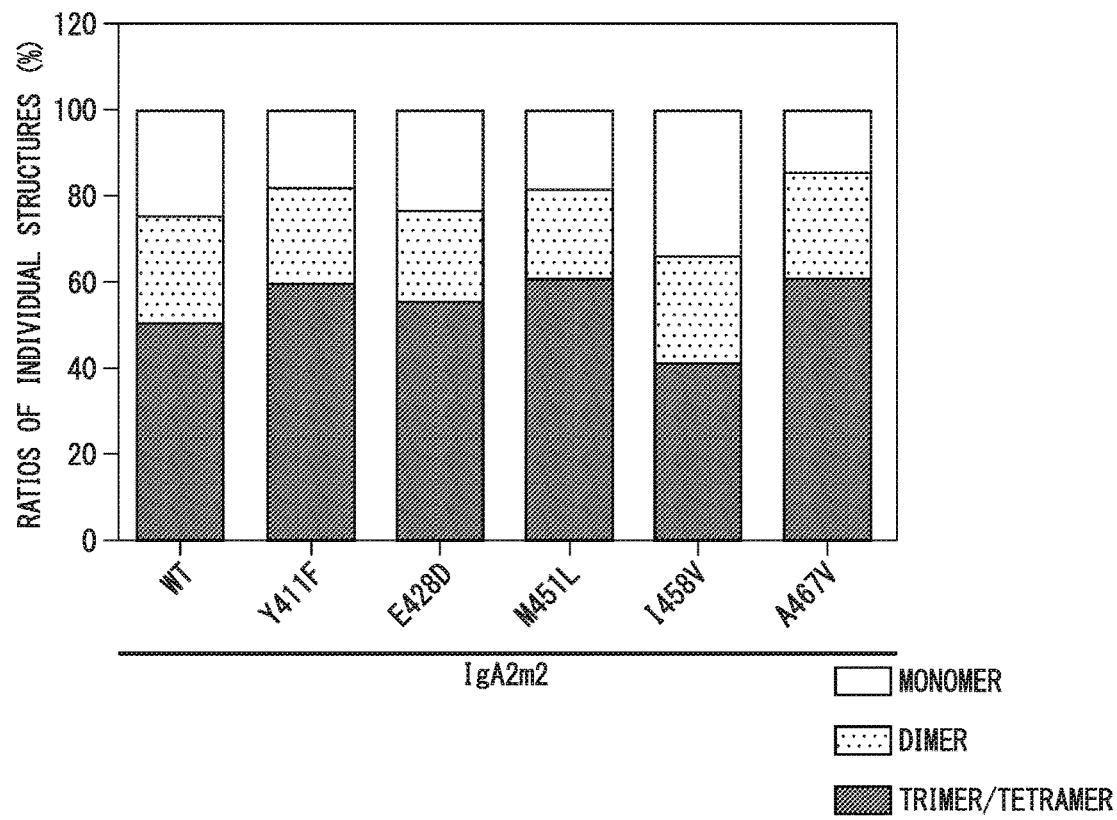
FIG. 11 is a graph illustrating results of Experimental Example 13.

Subsequently, an effect of each of the mutants on polymerization was analyzed in the same manner as in Experimental Example 11. FIG. 11 is a graph illustrating the examination results. As a result, it was revealed that, when I at position 458 of the IgA2m2 antibody was replaced with V, the polymerization was decreased, resulting in an increased ratio of the monomer.

Experimental Example 14: Examination of Polymerization of Single Amino Acid Substitution Mutants of IgA1 Antibody Mutants having an amino acid substitution in the Fc region were prepared and analyzed in the same manner as in Experimental Example 13. Hereinafter, the prepared mutant is named "IgA1 F411Y." In this case, the amino acid phenylalanine (F) corresponding to the 411$^{th}$ residue in the constant region of IgA1 is replaced with tyrosine (Y). This nomenclature equally applies to the other mutants.

Figure 12:
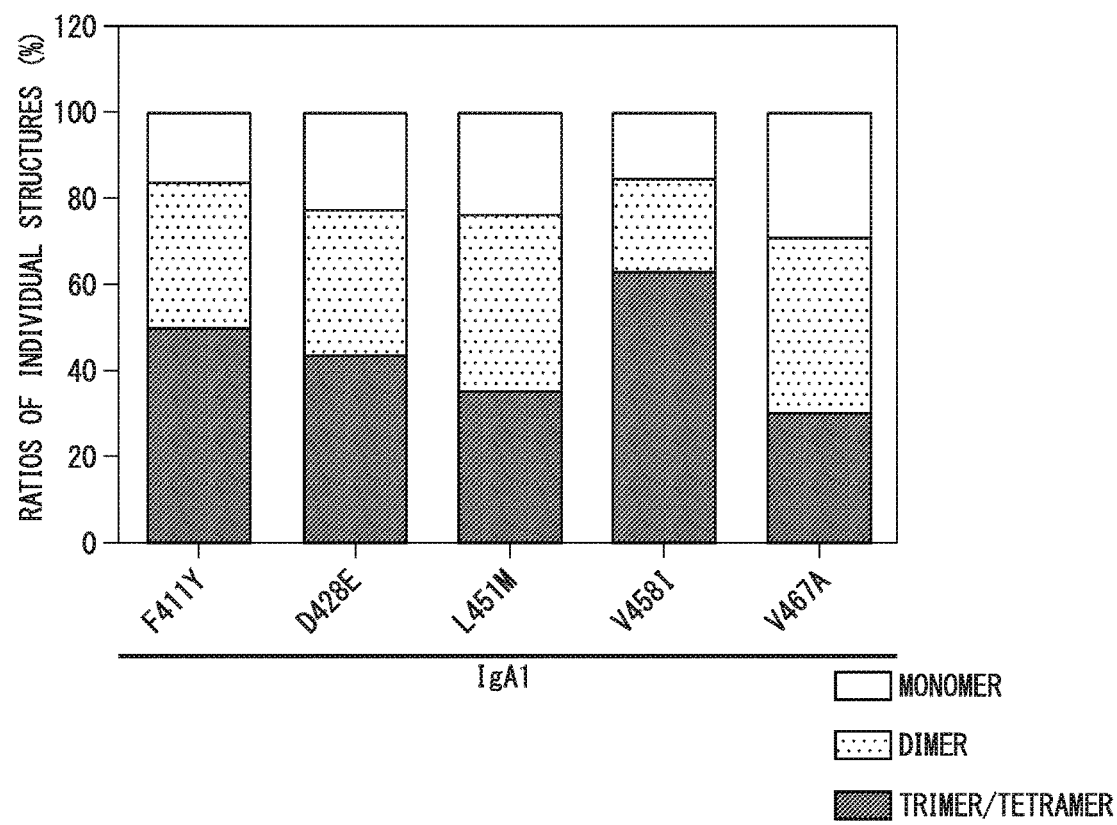
FIG. 12 is a graph illustrating results of Experimental Example 14.

Subsequently, an effect of each of the mutants on polymerization was analyzed in the same manner as in Experimental Example 11. FIG. 12 is a graph illustrating the examination results. As a result, it was revealed that, when V at position 458 of the IgA1 antibody was replaced with I, the polymerization was remarkably promoted.

Example 15: Analysis of V458 in IgA1 Heavy Chain on Polymerization-Promoting Activity of IgA To analyze the role of V458 in the IgA1 heavy chain on the polymerization-promoting activity of IgA, a V458 mutant expression vector was constructed, as follows.

(Construction of V458 Mutant Vector)

To construct mutants in which V at position 458 of the IgA1 heavy chain was replaced with various amino acids, pIgA1H-NRE was digested with restriction enzymes MfeI and HindIII to prepare a fragment for ligation. Also, to prepare insert linkers, each of the DNA fragments was thermally treated at 95° C. for 10 minutes in combination of V458I (SEQ ID NOs: 32 and 33), V458A (SEQ ID NOs: 34 and 35), V458W (SEQ ID NOs: 36 and 37), V458C (SEQ ID NOs: 38 and 39), V458D (SEQ ID NOs: 40 and 41), V458E (SEQ ID NOs: 42 and 43), V458F (SEQ ID NOs: 44 and 45), V458G (SEQ ID NOs: 46 and 47), V458H (SEQ ID NOs: 48 and 49), V458K (SEQ ID NOs: 50 and 51), V458L (SEQ ID NOs: 52 and 53), V458M (SEQ ID NOs: 54 and 55), V458N (SEQ ID NOs: 56 and 57), V458P (SEQ ID NOs: 58 and 59), V458Q (SEQ ID NOs: 60 and 61), V458R (SEQ ID NOs: 62 and 63), V458S (SEQ ID NOs: 64 and 65), V458T (SEQ ID NOs: 66 and 67), and V458Y (SEQ ID NOs: 68 and 69), and then annealed by gradually lowering the temperature to 25° C.

Subsequently, the respective linkers were ligated to the vector to construct pIgA1H-NRE-V458C, pIgA1H-NRE-V458A, pIgA1H-NRE-V458W, pIgA1H-NRE-V458C, pIgA1H-NRE-V458D, pIgA1H-NRE-V458E, pIgA1H-NRE-V458F, pIgA1H-NRE-V458G, pIgA1H-NRE-V458H, pIgA1H-NRE-V458K, pIgA1H-NRE-V458L, pIgA1H-NRE-V458M, pIgA1H-NRE-V458N, pIgA1H-NRE-V458P, pIgA1H-NRE-V458Q, pIgA1H-NRE-V458R, pIgA1H-NRE-V458S, pIgA1H-NRE-V458T, and pIgA1H-NRE-V458Y.

(Analysis of Gene Introduction and Expression of Various Mutant Expression Vectors)

Subsequently, C23 cells were transfected with a variety of the prepared V458 mutant expression vectors and the light chain expression vector (pIgA-LC) of the above-described anti-influenza virus antibody clone B12 using a lipofection method.

Subsequently, the transfected cells were cultured for 72 hours in DMEM supplemented with 5% fetal bovine serum, and 10 μL of each of the culture supernatants was then subjected to BN-PAGE and Western blotting analysis in the same manner as in Experimental Example 3 to evaluate an ability to produce the polymeric antibody.

Figure 13:
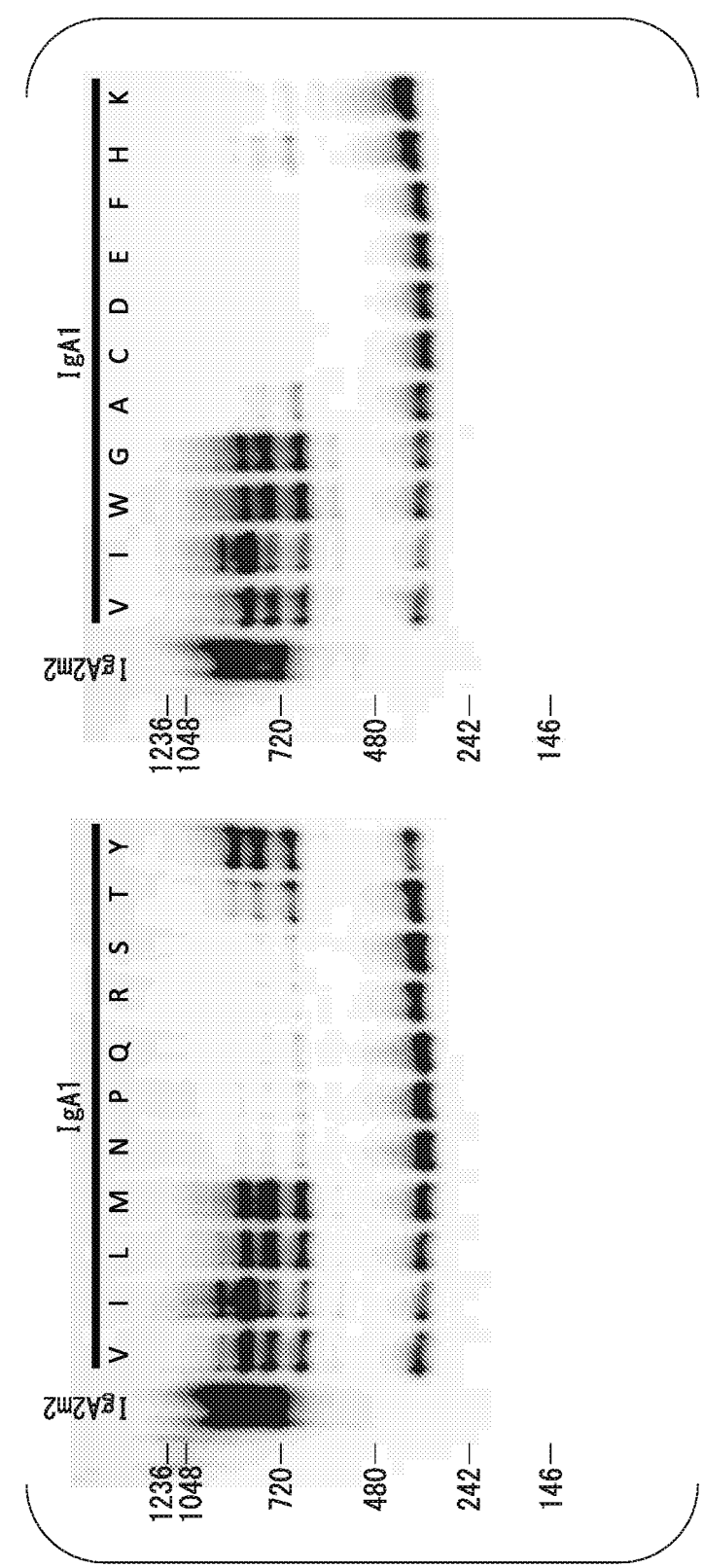
FIG. 13 is an image showing results of Experimental Example 15.

FIG. 13 is an image showing the results of Western blotting. As a result, the polymers were detected when the 458$^{th}$ residue was replaced with I, L, M, W, G, and Y. In particular, a shift toward a side of the polymer was observed when the 458$^{th}$ residue was replaced with I. When the 458$^{th}$ residue was replaced with amino acids other than the above amino acids, almost no formation of the polymer was observed. From these results, it was revealed that the 458$^{th}$ amino acid residue played an important role in formation of the polymer, and polymerization of the antibody was remarkably promoted when the 458$^{th}$ residue was a hydrophobic amino acid. Also, a strong activity to promote the polymerization was observed when the 458$^{th}$ residue was isoleucine.

Experimental Example 16: Examination of Polymerization of Amino Acid Substitution Mutants at 458$^{th}$ Residue of IgA1 Antibody in Expi293F Cells (Preparation of Amino Acid Substitution Mutants in Fc Region)

The same examination as in Experimental Example 15 was performed using Expi293F cells instead of the C23 cells. Specifically, the same experiments as in Experimental Example 13 were performed using the expression plasmids pIgA1H-NRE-V458I, pIgA1H-NRE-V458A, pIgA1H-NRE-V458W, pIgA1H-NRE-V458E, pIgA1H-NRE-V458G, pIgA1H-NRE-V458K, and pIgA1H-NRE-V458L prepared in Experimental Example 15.

Figure 14:
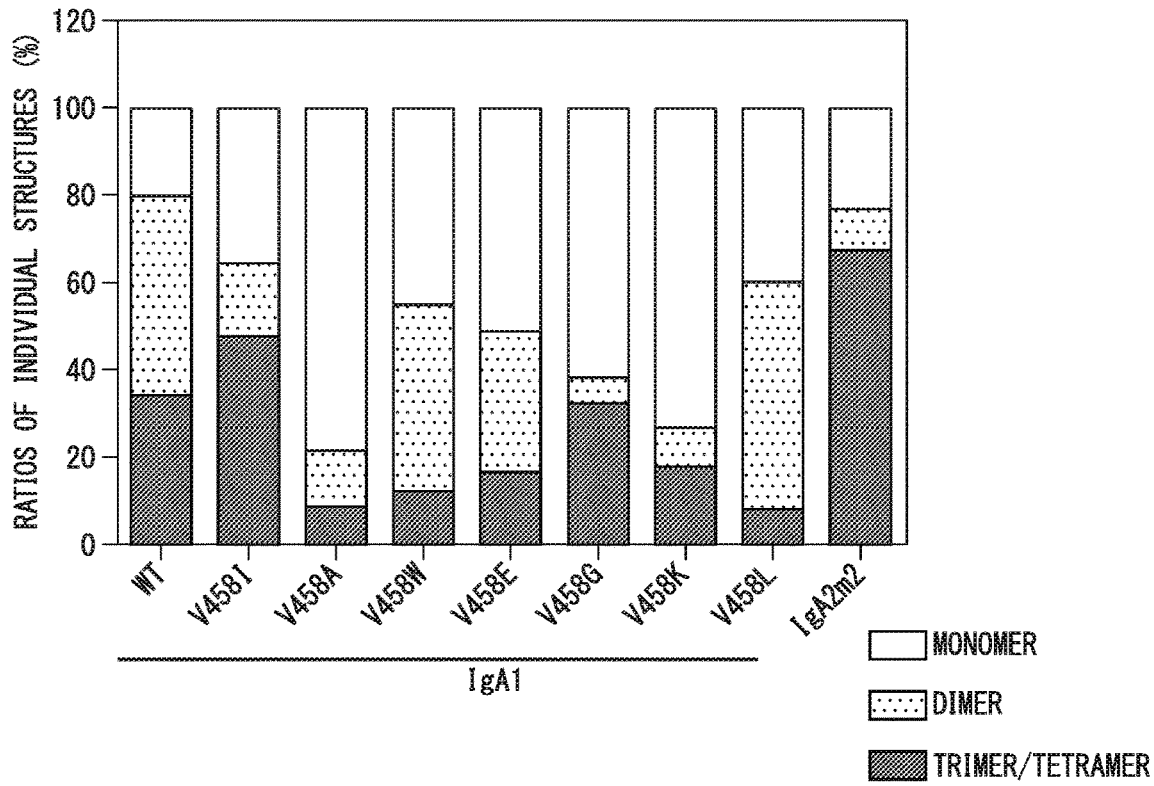
FIG. 14 is a graph illustrating results of Experimental Example 16.

FIG. 14 is a graph illustrating the examination results. As a result, it was revealed that the polymerization was remarkably promoted when V at position 458 of the IgA1 antibody was replaced with I.

Experimental Example 17: Examination of Role of V458 in Polymerization of IgA1 and Respective IgA2 Allotypes (Preparation of Amino Acid Substitution Mutants in Fc Region)

For IgA1, IgA2m1, IgA2m2, and IgA2(n), mutants in which the 458$^{th}$ residue was replaced were prepared, and the role of the mutations in polymerization was examined. To prepare amino acid substitution mutants of α2m1 HC, inverse PCR was performed using the α2m1 HC expression vector as a template and using a PrimeSTAR (registered trademark) MAX DNA Polymerase and primers designed to introduce an amino acid substitution (V458I) in the constant region (Fc region) of the heavy chain Subsequently, the 5'-terminus of the amplified PCR product was phosphorylated using a T4 polynucleotide kinase, and ligated in a circular form using a T4 DNA ligase. Then, *E. coli* was transformed with the reaction product, and plasmids were extracted to check whether a mutation causing the desired amino acid substitution was introduced via sequencing. For α2(n) HC, a mutant having an amino acid mutation at the 458$^{th}$ residue was prepared in the same manner. The mutants prepared in Experimental Examples 14 and 13 were used for the α1HC and α2m2 HC, respectively.

Figure 15:
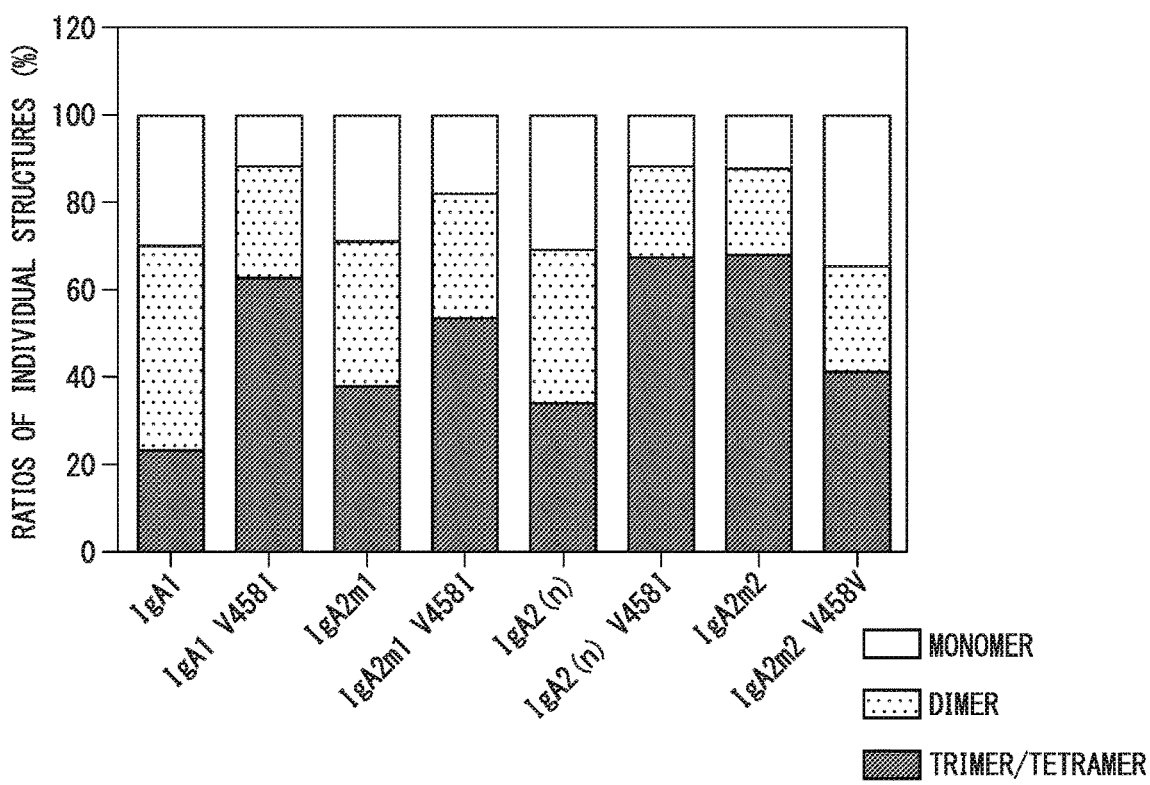
FIG. 15 is a graph illustrating results of Experimental Example 17.

Subsequently, an effect of each of the produced mutants on polymerization was analyzed in the same manner as in Experimental Example 13. FIG. 15 is a graph illustrating the examination results. As a result, remarkable polymerization-promoting activity was observed in the IgA1 and all the IgA2 allotypes when the 458$^{th}$ amino acid residue was substituted to I.

Experimental Example 18: Establishment of IgA Tetramer Stably Expressing Strains and Functional Analysis of Products Tetrameric IgA antibodies were prepared using the above-described spERt Technology, and analyzed according to the following method.

(Establishment of Strains Stably Expressing IgA Tetramer Using the spERt Technology)

A J/SC stably expressing CHO strain C23 was transfected with the light chain expression vector pIgA-LC of the anti-influenza virus antibody clone F11 and the IgA1 heavy chain expression vector pIgA1-HC of clone F11 or the IgA2m2 heavy chain expression vector pIgA2m2-HC of clone F11 using a lipofection method. A CHO strain C78 stably expressing the IgA1 heavy chain and light chain and a CHO strain C179 stably expressing the IgA2m2 heavy chain and light chain were established through drug selection using puromycin (10 μg/mL).

CHO-K1(1E26) cells were transfected with the above-described pCXSN-cis#1-hJC$_{NQ}$ and pCXSN-cis#2-hSC$_{NQ}$, the light chain expression vector pIgA-LC of the anti-influenza virus antibody clone F11, and the IgA1 heavy chain expression vector pIgA1-HC of clone F11 or the IgA2m2 heavy chain expression vector pIgA2m2-HC of clone F11 using a lipofection method, and drug selection was performed using Zeocin (400 μg/mL) and puromycin (10 μg/mL) to establish a CHO-K1 strain C104 stably expressing the IgA1 heavy and light chains, hJC$_{NQ}$ and hSC$_{NQ}$ and a CHO-K1 strain C117 stably expressing the IgA2m2 heavy and light chains, hJC$_{NQ}$ and hSC$_{NQ}$. The culture supernatant of each of the cells was analyzed using BN-PAGE and Western blotting. FIG. 16A is an image showing the results. It was confirmed that all of these cell lines efficiently secreted the IgA polymers.

(Analysis of Virus-Neutralizing Activity of IgA Polymeric Antibody)

Each of the above-described cell lines C78, C179, C104 and C117 was cultured for 7 days in DMEM supplemented with 5% fetal bovine serum, a culture medium was made clear using low-speed centrifugation and filtration using a filter having a pore size of 0.45 μm, and the IgA antibody was then purified with a CaptureSelect human Fc affinity matrix (commercially available from Life Technologies Inc.) in the same manner as in Experimental Examples 1 to 4.

The crudely purified IgA fraction was subjected to solvent substitution with PBS(−) using Vivaspin 20 (commercially available from GE Healthcare) to prepare IgA1 and IgA 2 m 2 polymeric antibody solutions.

The yields of the antibody were approximately 0.404 mg for C78, 0.712 mg for C179, approximately 0.298 mg for C104, and approximately 0.179 mg for C117 per 80 mL of the cell suspension. Also, the yield of the antibody could be raised by one to two orders of magnitude by performing suspension culture after serum-free conditioning of each of the cells, or checking culture conditions, a culture medium, etc.

The neutralizing activity of each of the prepared antibodies was determined by measuring the minimum neutralization concentration using a microneutralization test. Two-fold serial dilutions of an antibody sample were prepared, and mixed with a virus solution of 100 TCID$_{50}$ (100 times a 50% tissue culture infective dose), and the resulting mixture was then incubated at 37° C. for 30 minutes. Thereafter, this mixture was added to MDCK cells, and cultured for 5 days. Then, a value obtained by dividing a concentration of the sample by the maximum dilution ratio of the sample, in which a cytopathic effect by influenza viruses was not observed under a microscope, was used as the minimum neutralization concentration.

A vaccine-producing strain A/X-179A (H1N1pdm09) (hereinafter often referred to as "X-179A"), and a laboratory strain A/Puerto Rico/8/34 (H1N1) (hereinafter often referred to as "PR8") were used as the challenge viruses.

The results are listed in Table 7. As a result, the minimum neutralization concentrations of the IgA1 and IgA2m2 antibodies prepared from CHO cells with respect to X-179A were 0.44, 0.22, 0.63, and 0.22 μg/mL, the values of which were substantially the same as the minimum neutralization concentrations of the IgA1 and IgA2m2 antibodies prepared in the Expi293 cells. Also, the minimum neutralization concentrations of the IgA1 antibody with respect to the A/Puerto Rico/8/34 were 4.42 μg/mL, the values of which were substantially the same as the minimum neutralization concentrations of the IgA1 antibody prepared in the Expi 293 cells.

From the foregoing, it was revealed that the IgA1 and IgA2m2 antibodies prepared using the spERt Technology had the same neutralizing activity as the results measured in Experimental Example 7.

TABLE 7

Minimum neutralization concentration polymeric IgA antibody prepared in each CHO cell line against influenza viruses

| Clone name | Isotypes | JC/SC | Preparative CHO cell line name | Minimum neutralization concentration (μg/mL) | |
|---|---|---|---|---|---|
| | | | | X-179A | PR8 |
| F11 | IgA1 | WT/WT | C78 | 0.44 | 4.42 |
| | IgA2m2 | WT/WT | C179 | 0.22 | N.D. |
| | IgA1 | NQ/NQ | C104 | 0.63 | N.D. |
| | IgA2m2 | NQ/NQ | C117 | 0.22 | N.D. |

N.D.: Not determined

Experimental Example 19: Preparation of IgA Antibody Using the spERt Technology A productivity-enhancing effect of the IgA antibody using the spERt Technology was examined.

(Productivity-Enhancing Effect of Monomeric IgA Antibody)

A CHO-K1 cell line 1C17 stably expressing p180 and SF3b4 was established in the same manner as in the method disclosed in Experimental Example 12.

The cell lines C23, CHO-K1 and 1C17 were gradually conditioned under serum-free suspension culture conditions to establish cell lines C23S, CHO-K1S, and 1C17S. Also, expression vectors pIgA1-cis-HC and pIgA2m2-cis-HC in which cis #2 disclosed in International Publication No. WO 2014/157429 was inserted into pIgA1-HC or pIgA2m2-HC of the anti-influenza virus antibody clones B12 and clone F11, and an expression vector pIgA-cis-LC in which cis#1 was inserted into pIgA-LC of the anti-influenza virus antibody clone B12 and clone F11 were constructed.

CHO-K1S cells were transfected with the pIgA-LC and the pIgA1-HC or pIgA2m2-HC. Also, 1C17S cells were transfected with the pIgA-cis-LC and the pIgA1-cis-HC or pIgA2m2-cis-HC. After 48 hours, the culture supernatant was analyzed through SDS-PAGE and Western blotting. FIG. 16B is an image showing the results. In FIG. 16B, the term "293posi" represents a positive control of the polymeric IgA fraction prepared in the Expi293 cells as in Example 4, and the term "IgAposi" represents the standard of IgA.

As a result, it was revealed that the expression of IgA in the 1C17S cells dramatically increased compared to the CHO-K1S cells.

(Productivity-Enhancing Effect of Polymeric IgA Antibody)

To prepare a polymer of each of the clones, CHO-K1S cells were transfected with the above-described pIgA-LC, pEF-cis-hJC/Zeo, pEF/cis-hSC/Zeo, and pIgA1-HC or pIgA2m2-HC using a lipofection method.

Likewise, 1C17S cells were transfected with the above-described pIgA-cis-LC, pEF-cis-hJC/Zeo, pEF/cis-hSC/Zeo, and pIgA1-cis-HC or pIgA2m2-cis-HC.

Also, C23 cells were transfected with the pIgA-cis-LC and the pIgA1-cis-HC or pIgA2m2-cis-HC.

Subsequently, the culture supernatant after 48 hours was analyzed via BN-PAGE and Western blotting in the same manner as in Experimental Example 15. The results are shown in FIG. 16C. As a result, a positive band of the antibody against a human alpha chain was strongly detected in a range of 720 kDa or more for both of the clones B12 and F11 in the 1C17S cells and C23 cells, and an amount of the produced polymeric IgA1 antibody increased from 26 times to 35 times or more (FIG. 16 C, Lanes 1 to 3 and 7 to 9).

Also, an amount of the produced polymeric IgA2m2 antibody increased remarkably increased in the 1C17S cells and C23 cells. However, an expression of the polymeric IgA2m2 was hardly detected in the CHO-K1 S cells that were a parent strain of these cells (FIG. 16C, Lanes 4 to 6).

Figure 16D:
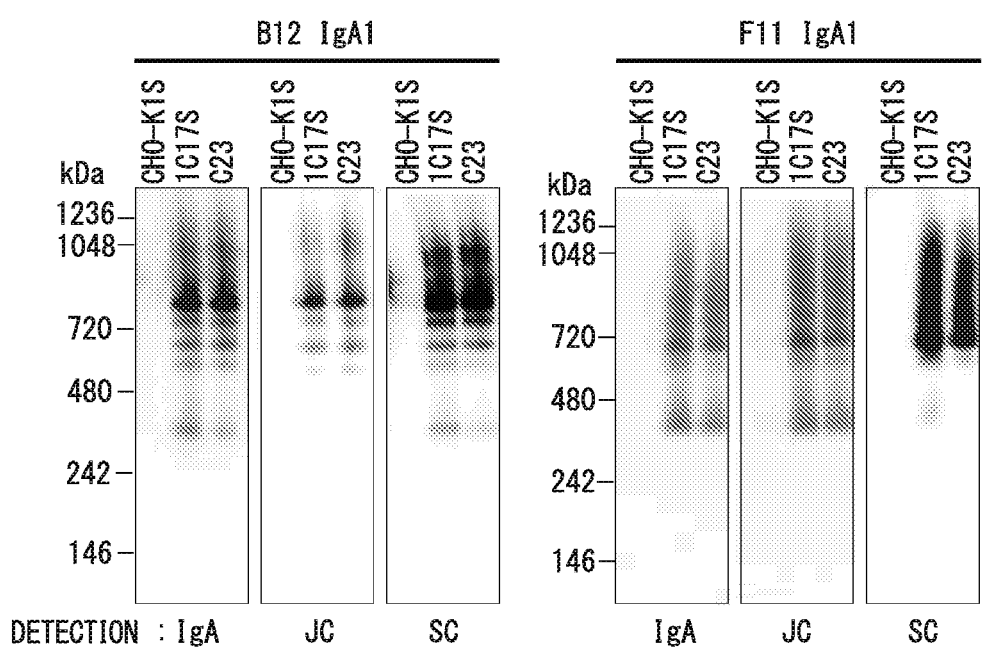
FIG. 16D is an image showing results of Experimental Example 19.

Also, as shown in FIG. 16D, Western blotting was performed using an anti-SC antibody and an anti-J chain antibody. As a result, it was confirmed that these polymer bands were positive for the SC and J chains.

From the above results, it was revealed that the productivity of the polymeric IgA antibody was able to be remarkably improved using the spERt Technology, and that the spERt Technology was highly useful for producing the IgA polymer.

Experimental Example 20: Mass Spectromic Analysis of IgA Polymer

The molecular weights of the polymeric (tetrameric) fraction components of the IgA1 and IgA2m2 prepared in the same manner as in Experimental Example 4 were measured using a mass spectrometer. Here, an untagged SC was prepared for IgA1 using the pCXSN-hSC. Also, a tagged SC was expressed for IgA2m2 using the pCXSN-hSC-HisTag to prepare each of the polymers.

First, a solvent of each of the IgA1 and IgA2m2 polymeric fractions was replaced with 12.5 mM ammonium acetate using a desalting column (commercially available from Thermo Fisher Scientific Inc., "Zeba Spin Desalting Columns," 7K MWCO, 0.5 mL). This sample was diluted 5 or 10 times with 50 mM or 100 mM ammonium acetate, introduced into a quadrupole-time-of-flight mass spectrometer maXis II (commercially available from Bruker Daltonics) using a nanoion source (commercially available from Advion, "Tri Versa NanoMate"), and then analyzed under the following conditions: ionization: ESI positive (high mass option), ion spray voltage: 1.4 to 1.8 kV, and ion source temperature: 80° C.

FIGS. 17A to 17D show examples of ion peaks corresponding to the tetramer measured under mild iontophoresis conditions using the high mass option and the monomer measured under nearly normal iontophoresis conditions.

Figure 17A:
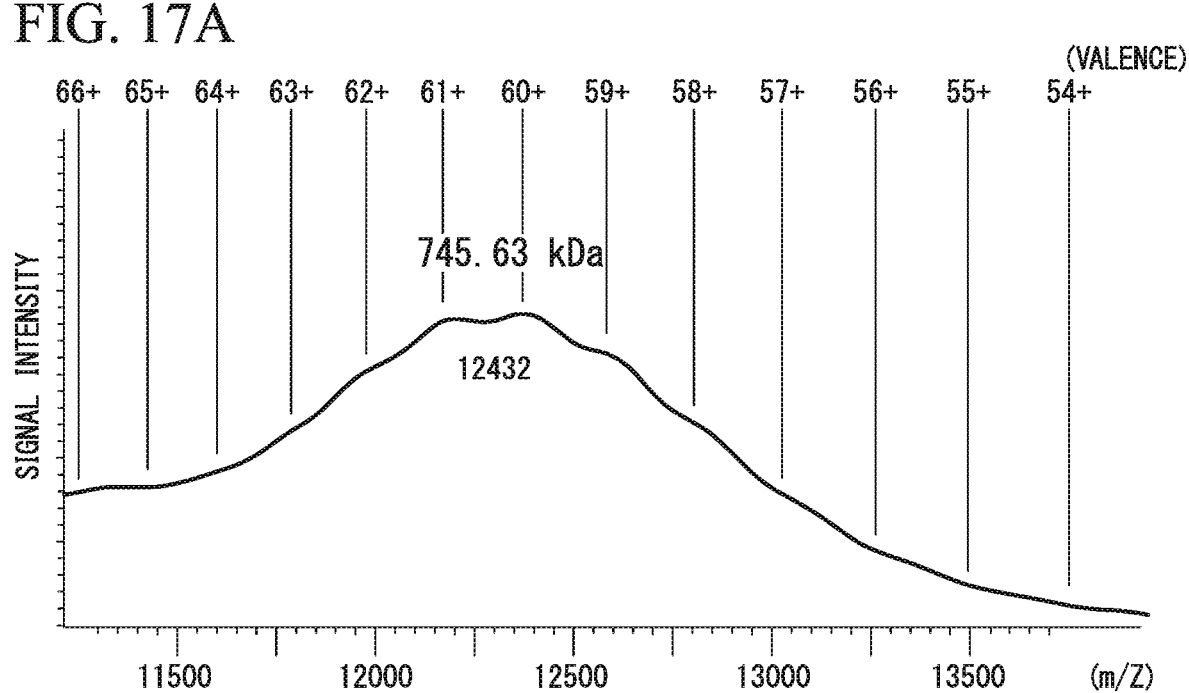
FIG. 17A is a graph illustrating results of Experimental Example 20.

As shown in FIG. 17A, a peak at an average molecular weight of 745.63 kDa corresponding to the tetramer and the like was detected in the polymeric fraction of IgA1 using mild iontophoresis.

Figure 17B:
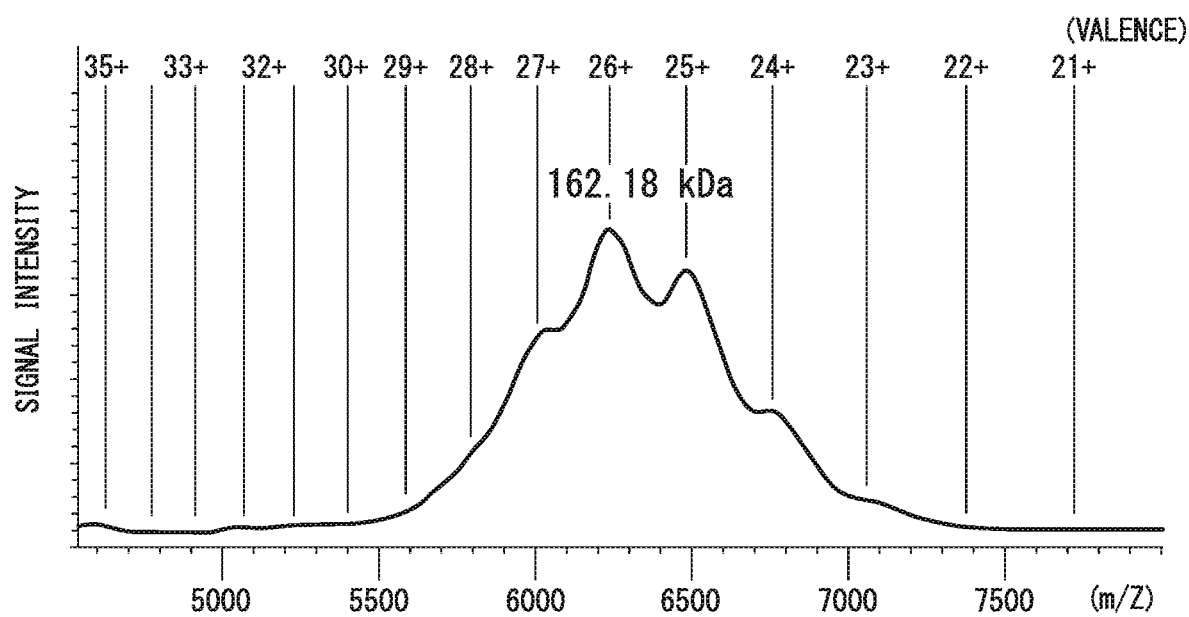
FIG. 17B is a graph illustrating results of Experimental Example 20.
Figure 17C:
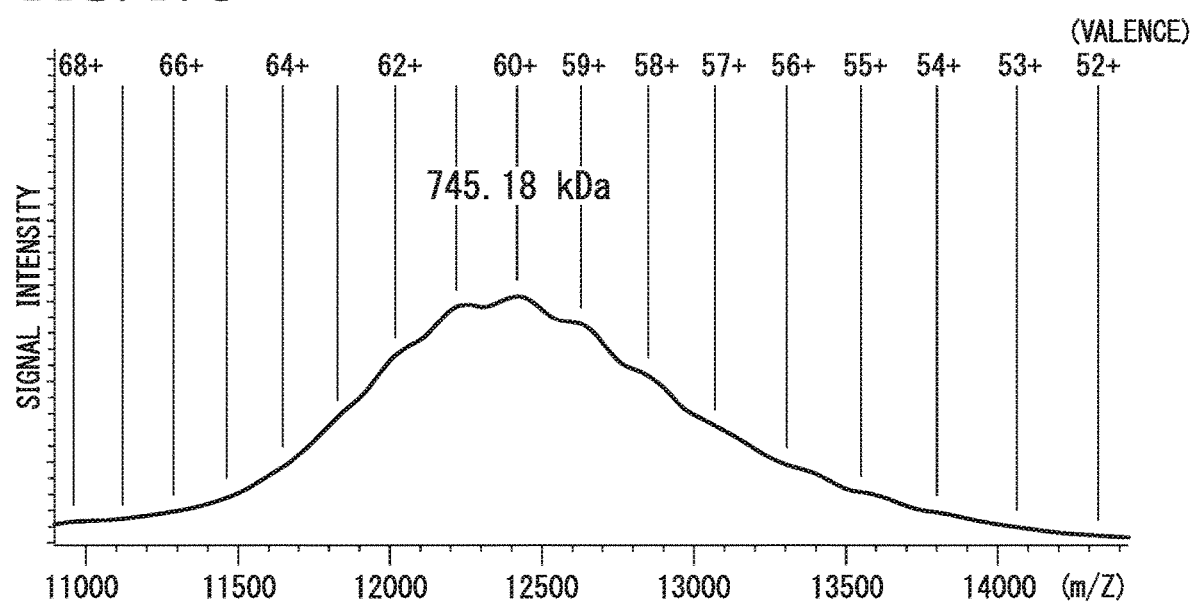
FIG. 17C is a graph illustrating results of Experimental Example 20.

As shown in FIG. 17C, a peak at 745.18 kDa corresponding to the tetramer and the like was detected in the polymeric fraction of IgA2m2 using mild iontophoresis.

When the complex was dissociated by introducing ions under nearly normal conditions, a peak at 162.18 kDa corresponding to the monomer of IgA1 and the like were detected, as shown in FIG. 17B.

Figure 17D:
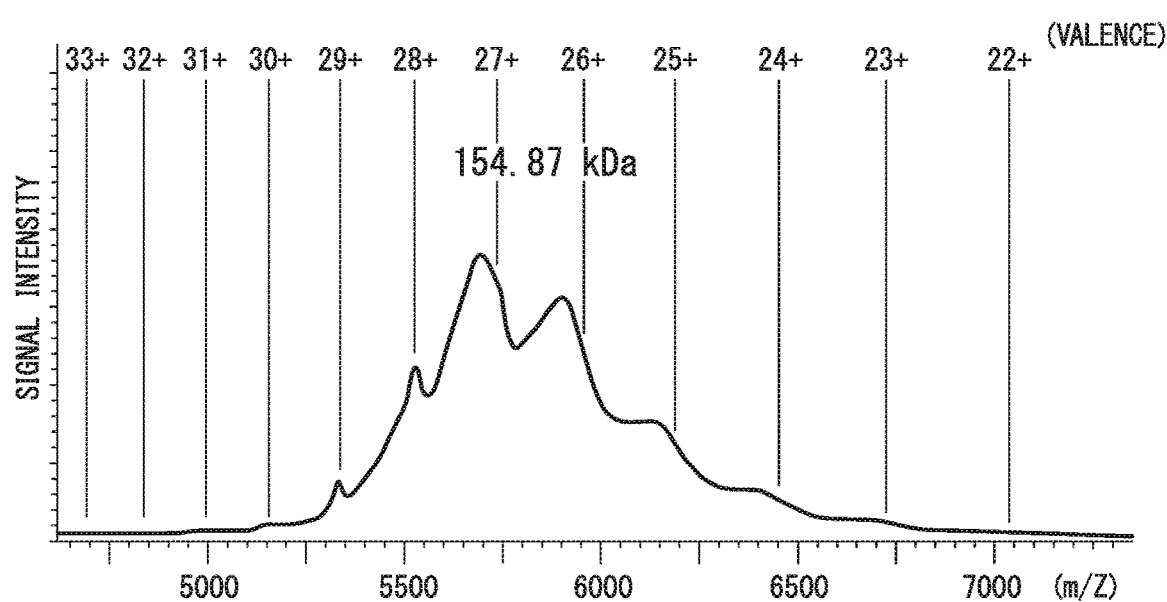
FIG. 17D is a graph illustrating results of Experimental Example 20.

Also, a peak at 154.87 kDa corresponding to the monomer of IgA2m2 and the like was detected by introducing ions under nearly normal conditions, as shown in FIG. 17D.

In addition, the ion peaks at 49.00 kDa and 49.21 kDa were detected from the analysis of the IgA1 polymeric fraction. Also, the ion peaks at 57.28 kDa, 23.03 kDa and 354.49 kDa were detected in the IgA2m2 polymeric fraction. The average molecular weights obtained from the respective samples are listed in Table 8.

TABLE 8

Summary of average molecular weights of polymeric (tetrameric) fractions observed in molecular weight analysis using the quadrupole-time-of-flight mass spectrometer

| | Average molecular weight of observed ion peaks (kDa) | | |
| --- | --- | --- | --- |
| Sample names | Tetramer peaks | Monomer peaks | Other peaks observed |
| Tetrameric IgA1 fraction | 745.63<br>745.85<br>748.09 | 162.18<br>163.38 | 49.00<br>49.21 |
| Tetrameric IgA2m2 fraction | 746.66<br>745.16 | 154.99<br>160.13<br>165.47 | 57.28<br>23.03<br>354.49 (dimer) |

Figure 18A:
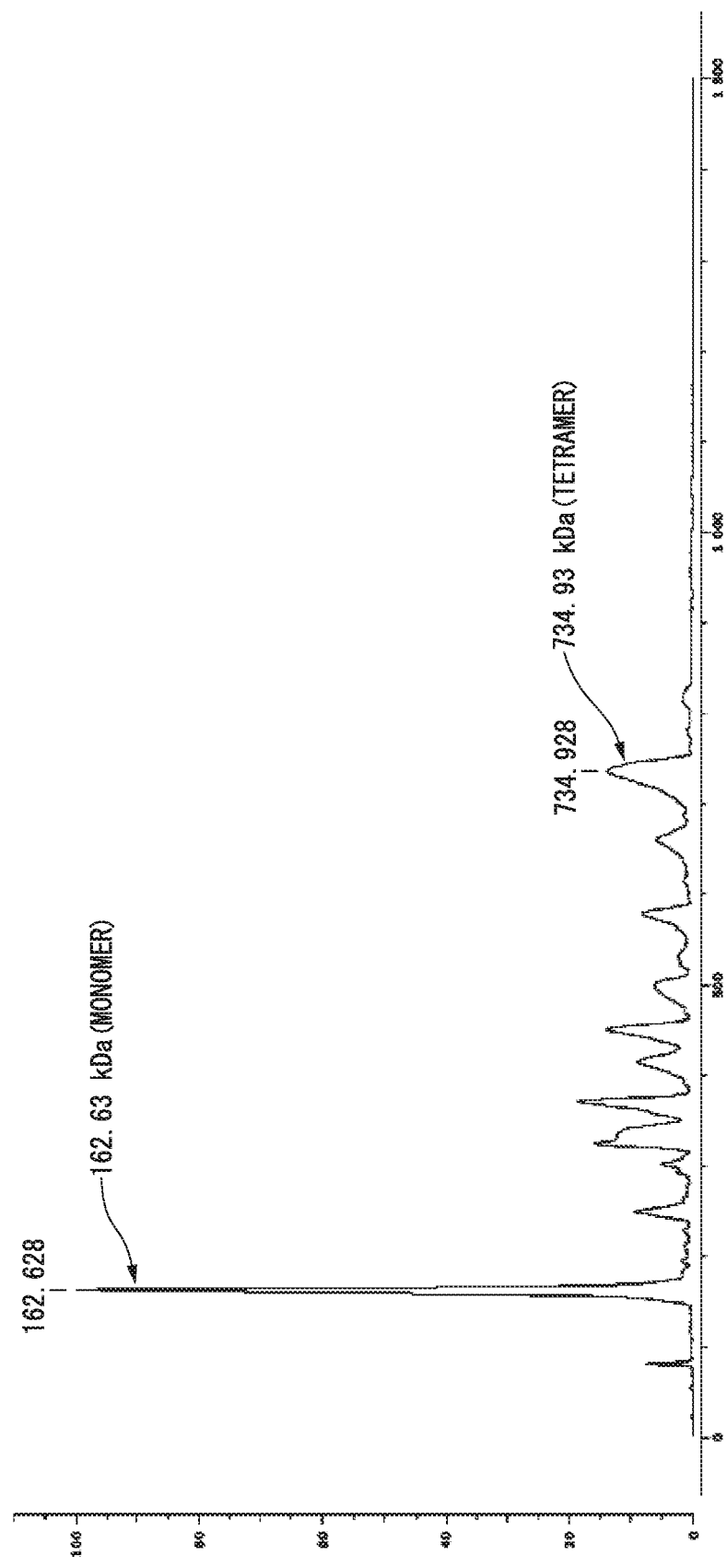
FIG. 18A is a graph illustrating results of Experimental Example 20.
Figure 18B:
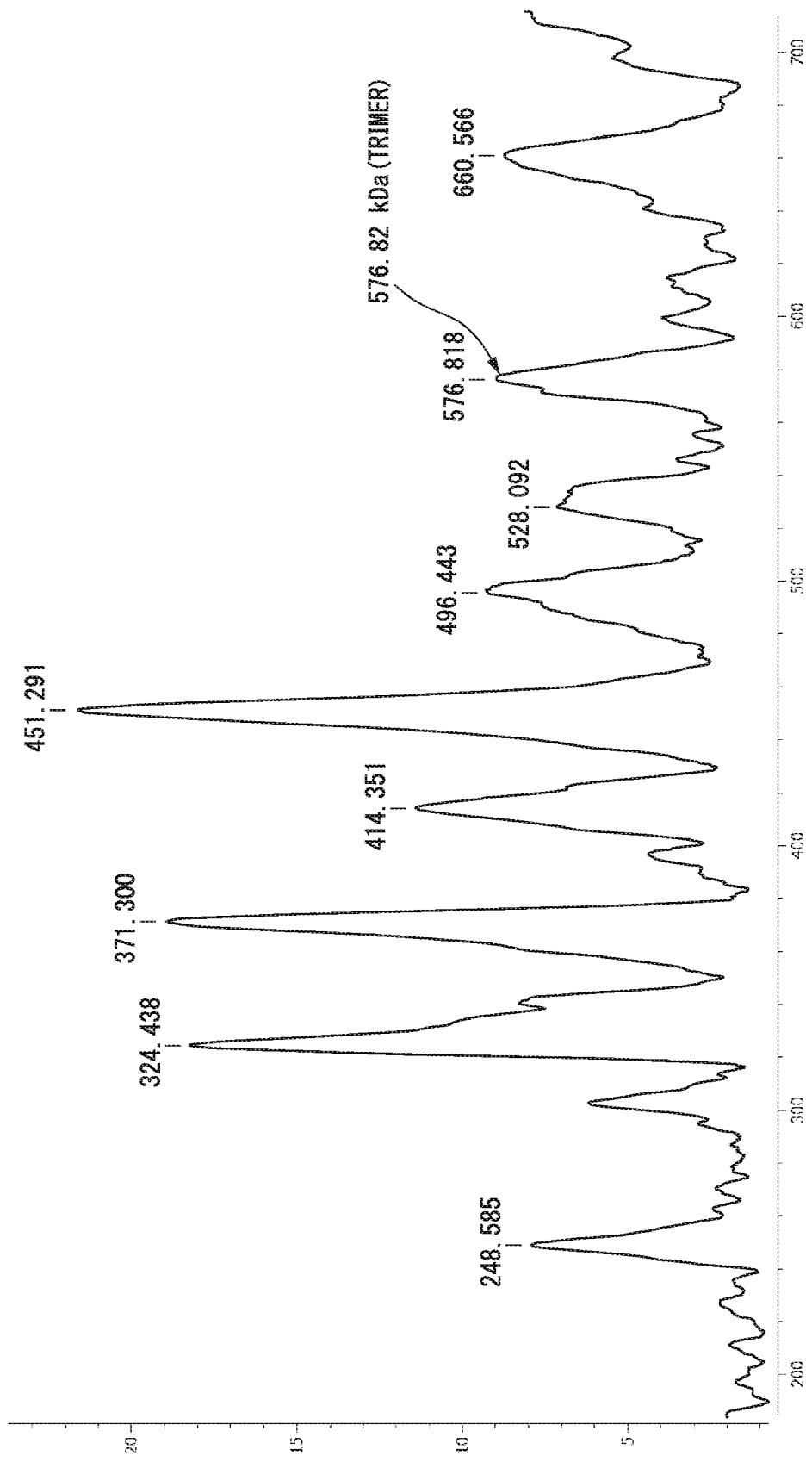
FIG. 18B is a graph illustrating results of Experimental Example 20.

Subsequently, for the polymeric (tetrameric) fraction of IgA2m2 prepared in the same manner as in Experimental Example 4, the molecular weight of the polymeric region was measured using a MALDI-TOF mass spectrometer TOF/TOF 5800 system (commercially available from AB Sciex) equipped with an HM3 interaction module (commercially available from CovalX). First, the sample was directly analyzed, and a peak at 162.63 kDa corresponding to the monomer and a peak at 734.93 kDa corresponding to the tetramer were detected, as shown in FIG. 18A. Also, a peak at 576.82 kDa was also detected, as shown in FIG. 18B. The peak at 576.82 kDa was believed to represent a trimeric type since the mass difference from the peak at 734.93 kDa corresponding to the tetramer was approximately 158 kDa.

Figure 18C:
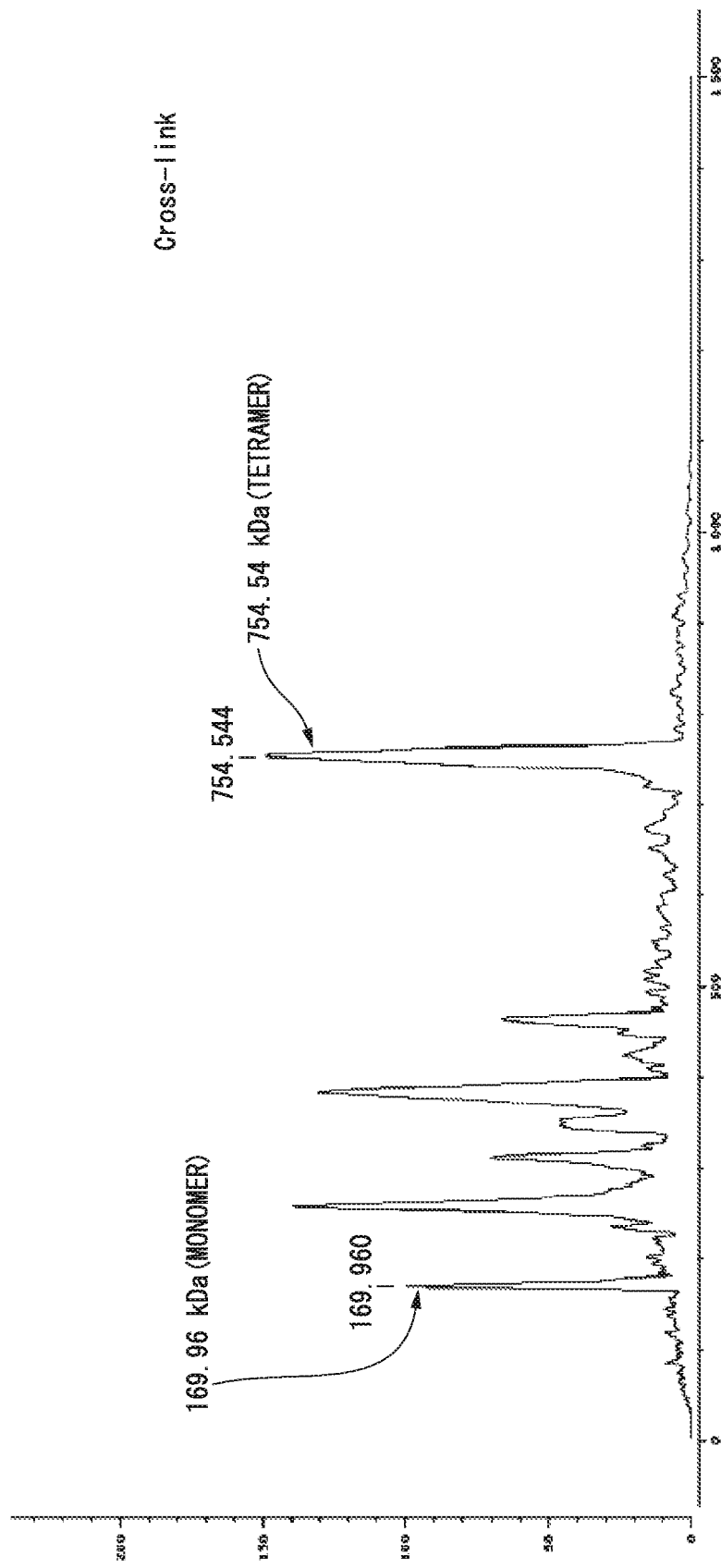
FIG. 18C is a graph illustrating results of Experimental Example 20.

Further, as shown in FIG. 18C, when the complex was stabilized using a crosslinking agent (see Bich C., et al., Reactivity and applications of new amine reactive crosslinkers for mass spectrometric detection of protein-protein complexes, Anal. Chem. 82, 172-179, 2010), an increase in the tetramer and a consequent decrease in the monomer were confirmed.

Example 21: Novel Quantitative Method Using Mass Spectrometry

To quantify the composition ratio of each of the subunits in the polymeric fraction with high accuracy, a novel quantitative method was established through mass spectrometry using stable isotope-labeled peptides as internal standards.

The peptides predicted to be generated by trypsin from amino acid sequences of the constant regions of each of the heavy chains ($\alpha1$, $\alpha2m1$, $\alpha2m2$, and $\alpha2n$) and each of light chains ($\lambda$ type and $\kappa$ type) of human IgA were compared to select candidates for IgA1 heavy chain ($\alpha1$)-specific sequences, IgA2 heavy chain ($\alpha2m1$, $\alpha2m2$, and $\alpha2n$)-specific sequences, IgA1/IgA2 consensus sequences, and $\lambda$ and $\kappa$ type-specific sequences of the light chain.

Here, to exclude an effect caused due to a difference in sequences of the constant region genes and alleles, which were different among individuals, for the light chains, the consensus sequences covering most of the subtypes were selected based on the information on the amino acid sequences registered in the public database IMGT.

Subsequently, the monomers of IgA1 and IgA2m2 prepared in the same manner as in Experimental Example 2 were digested with trypsin according to the following procedure, and then subjected to a high-performance liquid chromatography-mass spectrometer (LC-MS) to select sequences having good ion intensity from the candidate sequences, and stable isotope-labeled peptides in which lysine or arginine located at the C-terminus of each peptide was stable isotopically labeled ($^{13}C_6{}^{15}N_4$-Lys or $^{13}C_6{}^{15}N_4$-Arg) was synthesized via outsourcing (AnyGen Co., Ltd.). The selected amino acid sequences are listed in Table 9.

With respect to the J chain and SC, candidates were selected in the same manner, sequences having good ion intensity were selected based on the analysis results of tryptic digests of the polymeric fractions of IgA1 and IgA2m2 prepared in the same manner as in Experimental Example 4, and stable isotope-labeled peptides were synthesized via outsourcing (AnyGen Co., Ltd.). The selected amino acid sequences are listed in Table 9.

The human nasal mucosa-derived IgA dimeric fraction and the recombinant IgA1 polymeric fraction were analyzed using LC-MS. The human nasal mucosa-derived IgA dimeric fraction was prepared in the same manner as in the method disclosed in Suzuki T., et al., Relationship of the quaternary structure of human secretory IgA to neutralization of influenza virus, PNAS 112 (25), 7809-7817, 2015. Also, the recombinant IgA1 polymeric fraction was prepared in the same manner as in Experimental Example 4. For these samples, the subunit ratio of the IgA polymeric fraction was evaluated using LC-MS after trypsin digestion, as follows.

First, Tris-HCl (pH 7.6) and $CaCl_2$ were added to 10 µg of the IgA sample at concentrations of 100 mM and 1 mM, respectively, and 0.05 nmol of stable isotope-labeled peptides of each of the subunits were added as internal standards. DTT (commercially available from Wako) was added to such a solution at a concentration of 5 mM, and a reduction reaction was then performed by heating the solution at 56° C. for 30 minutes. Thereafter, iodoacetamide (commercially available from Wako) was added at a concentration of 25 mM, and an alkylation reaction of free SH groups was performed at room temperature for 30 minutes while shielding light. Then, 0.2 µg of trypsin (commercially available from Promega Corporation; "Sequencing Grade Modified Trypsin, Frozen") was added, and a degradation reaction was performed at 37° C. for 16 hours. Formic acid was added so that formic acid amounted for 1% of the resulting degradation solution, which was then used as a measurement sample.

The prepared peptide solution was analyzed using LC-MS (an LC part: Prominence manufactured by Shimadzu Corporation, and an MS part: maXis II manufactured by Bruker Daltonics). Separation was performed using an Ascentis Express C18 column (commercially available from Supleco; having a particle diameter of 5 µm. a diameter of 2.1 mm, and a length of 150 mm) at a column temperature of 25° C. and a flow rate of 0.5 mL/min under the following gradient conditions:

0 to 2 minutes: 98% Solution A (0.1% formic acid), and 2% Solution B (100% acetonitrile)

2.1 to 6 minutes: 98 to 50% Solution A, and 2 to 50% Solution B 6.1 to 8 minutes: 10% Solution A, and 90% Solution B 8.1 to 10 minutes: 98% Solution A, and 2% Solution B The separated peptide components were detected using the mass spectrometer under the following conditions. Ionization: ESI positive, ion spray voltage: 4.5 kV, and ion source temperature: 200° C.

The peak areas of the peptides derived from the respective subunits listed in Table 9 and the peak areas of corresponding stable isotope-labeled peptides were quantified. When it was assumed that the ratio of the heavy chain (consensus) was set to 1, the ratio of each of the subunits was calculated from the average of the peak area ratio of the two peptides.

Figure 19A:
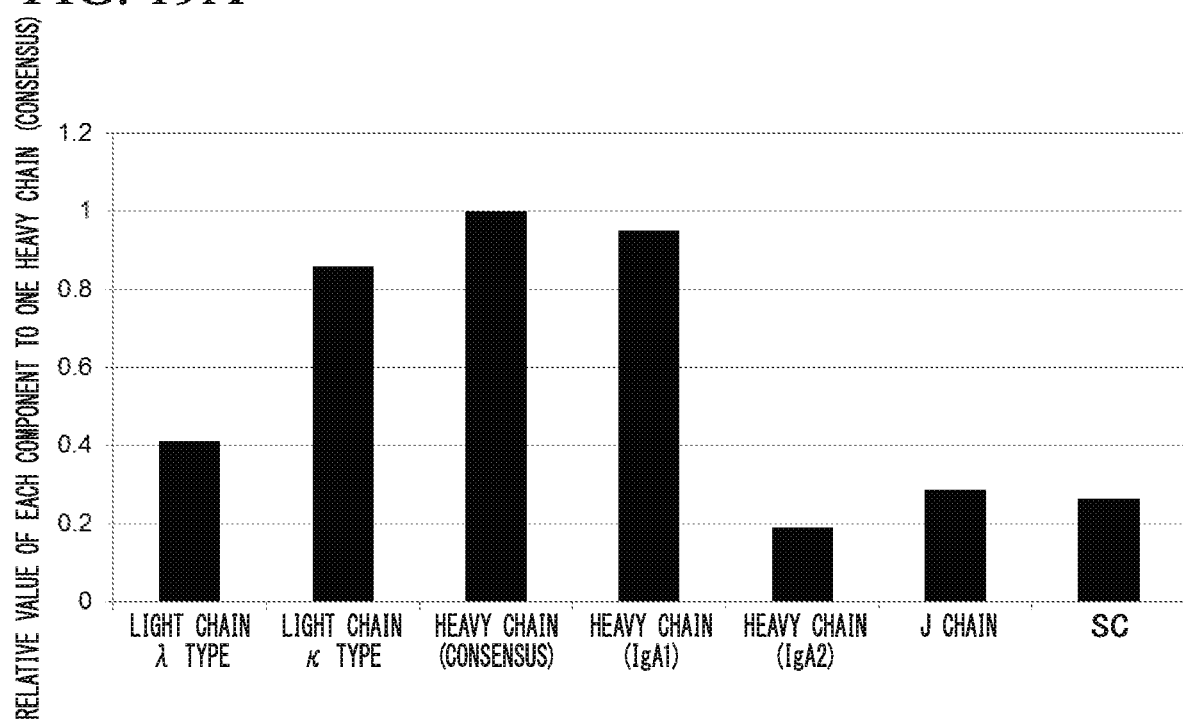
FIG. 19A is a graph illustrating results of Experimental Example 21.

FIG. 19A shows the analysis results of the human-derived IgA dimeric fraction. As a result, the ratio of the IgA1 and IgA2m2 in the heavy chain was approximately 5:1, and the ratio of the $\lambda$ type and $\kappa$ type in the light chain was approximately 1:2, indicating there are mixtures of subunits. Also, the ratio of the heavy chain and light chain as a whole was calculated to be approximately 1:1. On the other hand, the J chain and SC were clearly present at low quantities, and the ratio to the heavy chain and light chain was calculated to be approximately 1:4.

Figure 19B:
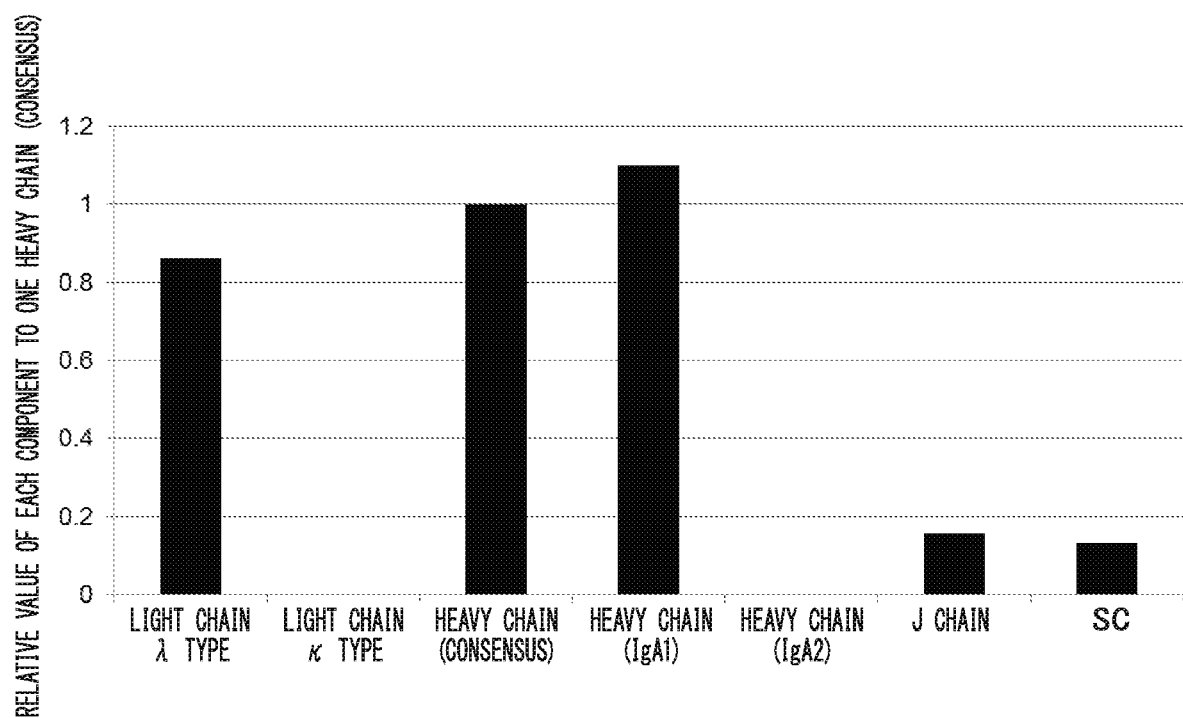
FIG. 19B is a graph illustrating results of Experimental Example 21.

FIG. 19B shows the analysis results of the recombinant IgA1 polymeric fraction. As a result, the $\lambda$ type of the light chain was detected at a ratio close to 1:1 with respect to the IgA1 heavy chain. On the other hand, the ratios of the J chain and SC to the IgA1 heavy chain were approximately 1:7 and approximately 1:8, respectively.

TABLE 9

| Subunit | Sequences | | m/z |
|---|---|---|---|
| Light chain λ type | YAASSYLSLTPEQWK (SEQ ID NO: 70) | Unlabeled | 872.4258 |
| | YAASSYLSLTPEQWK (SEQ ID NO: 71) | Labeled | 876.4329 |
| | SYSCQVTHEGSTVEK (SEQ ID NO: 72) | Unlabeled | 856.3760 |
| | SYSCQVTHEGSTVEK (SEQ ID NO: 73) | Labeled | 860.3831 |
| Light chain κ type | SGTASVVCLLNNFYPR (SEQ ID NO: 74) | Unlabeled | 899.4440 |
| | SGTASVVCLLNNFYPR (SEQ ID NO: 75) | Labeled | 904.4481 |
| | DSTYSLSSTLTLSK (SEQ ID NO: 76) | Unlabeled | 751.8756 |
| | DSTYSLSSTLTLSK (SEQ ID NO: 77) | Labeled | 755.8827 |
| Heavy chain (consensus) | WLQGSQELPR (SEQ ID NO: 78) | Unlabeled | 607.3126 |
| | WLQGSQELPR (SEQ ID NO: 79) | Labeled | 612.3167 |
| | YLTWASR (SEQ ID NO: 80) | Unlabeled | 448.7276 |
| | YLTWASR (SEQ ID NO: 81) | Labeled | 453.7317 |
| Heavy chain (IgA1) | NFPPSQDASGDLYTTSSQLTLPATQCLAGK (SEQ ID NO: 82) | Unlabeled | 1056.8360 |
| | NFPPSQDASGDLYTTSSQLTLPATQCLAGK (SEQ ID NO: 83) | Labeled | 1059.5074 |
| | DASGVTFTWTPSSGK (SEQ ID NO: 84) | Unlabeled | 770.8603 |
| | DASGVTFTWTPSSGK (SEQ ID NO: 85) | Labeled | 774.8674 |
| Heavy chain (IgA2) | NFPPSQDASGDLYTTSSQLTLPATQCPDGK (SEQ ID NO: 86) | Unlabeled | 1066.1555 |
| | NFPPSQDASGDLYTTSSQLTLPATQCPDGK (SEQ ID NO: 87) | Labeled | 1068.8269 |
| | DASGATFTWTPSSGK (SEQ ID NO: 88) | Unlabeled | 756.8446 |
| | DASGATFTWTPSSGK (SEQ ID NO: 89) | Labeled | 760.8517 |
| J chain | SSEDPNEDIVER (SEQ ID NO: 90) | Unlabeled | 695.3028 |
| | SSEDPNEDIVER (SEQ ID NO: 91) | Labeled | 700.3069 |
| | CYTAVVPLVYGGETK (SEQ ID NO: 92) | Unlabeled | 829.9115 |
| | CYTAVVPLVYGGETK (SEQ ID NO: 93) | Labeled | 832.9185 |
| SC | VYTVDLGR (SEQ ID NO: 94) | Unlabeled | 461.7460 |
| | VYTVDLGR (SEQ ID NO: 95) | Labeled | 466.7501 |
| | GSVTFHCALGPEVANVAK (SEQ ID NO: 96) | Unlabeled | 619.6417 |
| | GSVTFHCALGPEVANVAK (SEQ ID NO: 97) | Labeled | 622.3131 |

K and R represent stable isotope-labeled sites

INDUSTRIAL APPLICABILITY

According to the present invention, a polymeric IgA-type recombinant antibody can be provided. Also, a medicine containing the polymeric IgA-type recombinant antibody as an active ingredient can be provided. In addition, a method of producing the polymeric IgA-type antibody can be provided. Further, a method of improving the antigen-binding activity of the antibody can be provided.

ACCESSION NUMBER

NITE BP-01535

---

The invention claimed is:

1. A recombinant polymeric IgA-type antibody, wherein an amino acid residue at position 458 of a heavy chain constant region with the numbering of the amino acid residues of the corresponding human IgA1 antibody is an isoleucine and wherein the heavy chain constant region has an amino acid sequence which is at least partially derived from a non-IgA antibody or an IgA-type antibody other than IgA2m2.

2. A method of producing a polymeric IgA-type antibody, the method comprising:
coexpressing an IgA-type antibody heavy-chain protein wherein an amino acid residue at position 458 of the heavy chain constant region is an isoleucine and wherein the heavy chain constant region has an amino acid sequence which is at least partially derived from a non-IgA antibody or an IgA-type antibody other than IgA2m2, an antibody light chain protein, an antibody J-chain protein, and a secretory component protein in a single cell, to produce the recombinant polymeric IgA-type antibody according to claim 1.

3. The method according to claim 2, wherein the IgA-type antibody heavy-chain protein is converted from an IgG-type into an IgA-type by means of genetic recombination.

4. The method according to claim 2, wherein a p180 protein and an SF3b4 protein are further coexpressed in the single cell in the coexpressing.

5. The method according to claim 2, wherein the coexpressing is carried out by introducing an expression vector for expressing an IgA-type antibody heavy-chain protein wherein an amino acid residue at position 458 of the heavy chain constant region is an isoleucine, an antibody light-chain protein, an antibody J-chain protein, and a secretory component protein into the single cell, and
the expression vector has a cis-element, which an RNA-binding protein recognizes, binds to or interacts with, downstream from a promoter and also upstream from an initiation codon of nucleic acids coding for the IgA-type antibody heavy-chain protein, the antibody light-chain protein, the antibody J-chain protein, or the secretory component protein.

6. The method according to claim 5, wherein the cis-element comprises one to several base sequences consisting of a sequence motif $GAN_1-(X)_n-ACN_2$ (where n is an integer ranging from 3 to 6, and $N_1$ and $N_2$ are each independently any one selected from A, T, G, and C).

7. The method according to claim 5, wherein the cis-element consists of:
a base sequence set forth in any one selected from SEQ ID NOs: 21 to 23,
a base sequence wherein one to several bases are deleted, substituted or added in the base sequence set forth in any one selected from SEQ ID NOs: 21 to 23, and which the RNA-binding protein recognizes, binds to or interacts with,
a base sequence having an identity of 80% or more to the base sequence set forth in any one selected from SEQ ID NOs: 21 to 23, and which the RNA-binding protein recognizes, binds to or interacts with, or
a base sequence hybridizable under a stringent condition with a nucleic acid consisting of a base sequence complementary to the nucleic acid consisting of the base sequence set forth in any one selected from SEQ ID NOs: 21 to 23, and which the RNA-binding protein recognizes, binds to or interacts with.

8. A method of improving the antigen-binding activity or neutralizing activity of an antibody, the method comprising:
making antibody into the recombinant IgA-type antibody according to claim 1.

9. The method according to claim 8, wherein the antibody is an IgG-type antibody.

10. The method according to claim 8, wherein the making comprises:
coexpres sing an IgA-type antibody heavy-chain protein having a heavy-chain variable region of the antibody and wherein an amino acid residue at position 458 of the heavy chain constant region is an isoleucine, a light-chain protein of the antibody, an antibody J-chain protein, and a secretory component protein in a single cell.

11. The recombinant IgA-type antibody according to claim 1, wherein the IgA-type antibody comprises secretary component protein.

12. The recombinant polymeric IgA-type antibody according to claim 1, wherein the IgA-type antibody is an anti-virus antibody, wherein the virus causes mucosal infections.

13. The recombinant polymeric IgA-type antibody according to claim 12, wherein the mucosal infections are selected from the group consisting of influenza, RS virus infection, severe acute respiratory syndrome (SARS), Middle Eastern respiratory syndrome (MERS), and acquired immune deficiency syndrome (AIDS).

* * * * *

SEQUENCE LISTING

<160> NUMBER OF SEQ ID NOS: 101

<210> SEQ ID NO 1
<211> LENGTH: 10
<212> TYPE: PRT
<213> ORGANISM: Homo sapiens
<220> FEATURE:
<221> NAME/KEY: misc_feature
<223> OTHER INFORMATION: clone F11 CDR-H1

<400> SEQUENCE: 1

Gly Gly Ser Phe Thr Ser Phe Ala Ile Ser
1               5                   10

```
<210> SEQ ID NO 2
<211> LENGTH: 17
<212> TYPE: PRT
<213> ORGANISM: Homo sapiens
<220> FEATURE:
<221> NAME/KEY: misc_feature
<223> OTHER INFORMATION: clone F11 CDR-H2

<400> SEQUENCE: 2

Arg Ile Thr Arg Ile Leu Gly Val Pro Asn Tyr Ala Gln Lys Phe Gln
1               5                   10                  15

Gly

<210> SEQ ID NO 3
<211> LENGTH: 11
<212> TYPE: PRT
<213> ORGANISM: Homo sapiens
<220> FEATURE:
<221> NAME/KEY: misc_feature
<223> OTHER INFORMATION: clone F11 CDR-H3

<400> SEQUENCE: 3

Asp Ser Gly Thr Ser His Gly Asp Phe Asp Tyr
1               5                   10

<210> SEQ ID NO 4
<211> LENGTH: 11
<212> TYPE: PRT
<213> ORGANISM: Homo sapiens
<220> FEATURE:
<221> NAME/KEY: misc_feature
<223> OTHER INFORMATION: clone F11 CDR-L1

<400> SEQUENCE: 4

Arg Ala Ser Gln Asn Val Ile Asn Ser Leu Val
1               5                   10

<210> SEQ ID NO 5
<211> LENGTH: 7
<212> TYPE: PRT
<213> ORGANISM: Homo sapiens
<220> FEATURE:
<221> NAME/KEY: misc_feature
<223> OTHER INFORMATION: clone F11 CDR-L2

<400> SEQUENCE: 5

Gly Ala Ser Asn Arg Ala Thr
1               5

<210> SEQ ID NO 6
<211> LENGTH: 9
<212> TYPE: PRT
<213> ORGANISM: Homo sapiens
<220> FEATURE:
<221> NAME/KEY: misc_feature
<223> OTHER INFORMATION: clone F11 CDR-L3

<400> SEQUENCE: 6

Gln Gln Arg Gly Thr Trp Leu Trp Ser
1               5

<210> SEQ ID NO 7
<211> LENGTH: 120
<212> TYPE: PRT
<213> ORGANISM: Homo sapiens
<220> FEATURE:
<221> NAME/KEY: misc_feature
<223> OTHER INFORMATION: clone F11 heavy chain variable region
```

<400> SEQUENCE: 7

Gln Val Gln Leu Val Gln Ser Gly Ala Glu Val Lys Arg Pro Gly Ser
1               5                   10                  15

Ser Val Arg Val Ser Cys Arg Thr Ser Gly Gly Ser Phe Thr Ser Phe
            20                  25                  30

Ala Ile Ser Trp Val Arg Gln Ala Pro Gly Gln Gly Leu Glu Trp Met
        35                  40                  45

Gly Arg Ile Thr Arg Ile Leu Gly Val Pro Asn Tyr Ala Gln Lys Phe
    50                  55                  60

Gln Gly Arg Val Thr Ile Thr Ala Asp Met Pro Thr Thr Thr Ala Tyr
65                  70                  75                  80

Leu Asp Leu Thr Asn Leu Arg Ser Glu Asp Thr Ala Val Tyr Tyr Cys
                85                  90                  95

Ala Arg Asp Ser Gly Thr Ser His Gly Asp Phe Asp Tyr Trp Gly Gln
            100                 105                 110

Gly Thr Leu Val Thr Val Ser Ser
        115                 120

<210> SEQ ID NO 8
<211> LENGTH: 107
<212> TYPE: PRT
<213> ORGANISM: Homo sapiens
<220> FEATURE:
<221> NAME/KEY: misc_feature
<223> OTHER INFORMATION: clone F11 light chain variable region

<400> SEQUENCE: 8

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Asn Val Ile Asn Ser
            20                  25                  30

Leu Val Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Arg Gly
    50                  55                  60

Ser Gly Ser Gly Thr Asp Phe Thr Leu Thr Ile Asp Ser Leu Glu Pro
65                  70                  75                  80

Glu Asp Ile Ala Val Tyr Tyr Cys Gln Gln Arg Gly Thr Trp Leu Trp
                85                  90                  95

Ser Phe Gly Gln Gly Thr Lys Val Glu Ile Lys
            100                 105

<210> SEQ ID NO 9
<211> LENGTH: 10
<212> TYPE: PRT
<213> ORGANISM: Homo sapiens
<220> FEATURE:
<221> NAME/KEY: misc_feature
<223> OTHER INFORMATION: clone H5 CDR-H1

<400> SEQUENCE: 9

Gly Gly Thr Phe Ser Ser Tyr Ala Ile Ser
1               5                   10

<210> SEQ ID NO 10
<211> LENGTH: 17
<212> TYPE: PRT
<213> ORGANISM: Homo sapiens
<220> FEATURE:

```
<221> NAME/KEY: misc_feature
<223> OTHER INFORMATION: clone H5 CDR-H2

<400> SEQUENCE: 10

Gly Ile Ile Pro Ile Phe Gly Thr Ala Asn Tyr Ala Gln Lys Phe Gln
1               5                   10                  15

Gly

<210> SEQ ID NO 11
<211> LENGTH: 17
<212> TYPE: PRT
<213> ORGANISM: Homo sapiens
<220> FEATURE:
<221> NAME/KEY: misc_feature
<223> OTHER INFORMATION: clone H5 CDR-H3

<400> SEQUENCE: 11

Gly Gly Val Asn Ile Val Ala Thr Ile Ile Tyr Tyr Tyr Ala Leu Asp
1               5                   10                  15

Val

<210> SEQ ID NO 12
<211> LENGTH: 20
<212> TYPE: PRT
<213> ORGANISM: Homo sapiens
<220> FEATURE:
<221> NAME/KEY: misc_feature
<223> OTHER INFORMATION: clone H5 CDR-L1

<400> SEQUENCE: 12

Thr Gly Thr Ser Ser Asp Val Gly Gly Tyr Asn Tyr Val Ser Trp Tyr
1               5                   10                  15

Gln Tyr Val Ser
            20

<210> SEQ ID NO 13
<211> LENGTH: 7
<212> TYPE: PRT
<213> ORGANISM: Homo sapiens
<220> FEATURE:
<221> NAME/KEY: misc_feature
<223> OTHER INFORMATION: clone H5 CDR-L2

<400> SEQUENCE: 13

Asp Val Ser Asn Arg Pro Ser
1               5

<210> SEQ ID NO 14
<211> LENGTH: 11
<212> TYPE: PRT
<213> ORGANISM: Homo sapiens
<220> FEATURE:
<221> NAME/KEY: misc_feature
<223> OTHER INFORMATION: clone H5 CDR-L3

<400> SEQUENCE: 14

Ser Ser Tyr Thr Ser Ser Ser Thr Gln Val Val
1               5                   10

<210> SEQ ID NO 15
<211> LENGTH: 128
<212> TYPE: PRT
<213> ORGANISM: Homo sapiens
<220> FEATURE:
<221> NAME/KEY: misc_feature
<223> OTHER INFORMATION: clone H5 heavy chain variable region
```

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Val Asn Ile Val Ala Thr Ile Ile Tyr Tyr Tyr Ala
            100                 105                 110

Leu Asp Val Trp Gly Arg Gly Gln Gly Thr Thr Val Thr Val Ser Ser
        115                 120                 125

<210> SEQ ID NO 16
<211> LENGTH: 117
<212> TYPE: PRT
<213> ORGANISM: Homo sapiens
<220> FEATURE:
<221> NAME/KEY: misc_feature
<223> OTHER INFORMATION: clone H5 light chain variable region

<400> SEQUENCE: 16

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Tyr Val Ser Trp Tyr Gln Gln His Pro
        35                  40                  45

Gly Lys Ala Pro Lys Leu Met Ile Tyr Asp Val Ser Asn Arg Pro Ser
    50                  55                  60

Gly Val Ser Asn Arg Phe Ser Gly Ser Lys Ser Gly Asn Thr Ala Ser
65                  70                  75                  80

Leu Thr Ile Ser Gly Leu Gln Ala Glu Asp Glu Ala Asp Tyr Tyr Cys
                85                  90                  95

Ser Ser Tyr Thr Ser Ser Ser Thr Gln Val Val Phe Gly Gly Gly Thr
            100                 105                 110

Lys Leu Thr Val Leu
        115

<210> SEQ ID NO 17
<211> LENGTH: 361
<212> TYPE: DNA
<213> ORGANISM: Homo sapiens
<220> FEATURE:
<221> NAME/KEY: misc_feature
<223> OTHER INFORMATION: clone F11 heavy chain variable region

<400> SEQUENCE: 17
caggtgcagc tggtgcagtc tggggctgag gtaaagaggc ctggctcctc ggtgagggtc      60
tcctgcagga cttctggagg cagcttcacc agttttgcta tcagctgggt gcgacaggcc    120
cctggacaag ggcttgagtg gatgggaagg atcacccgta tacttggtgt cccaaactac    180

```
gcacagaagt tccagggcag agtcacgatt accgcggaca tgcctacgac cacagcctac    240
ttggacctga cgaacctgag atcggaagac acggccgttt attactgtgc aagagattcg    300
ggaaccagtc atggagattt tgactactgg ggccagggaa ccctggtcac cgtctcctca    360
g                                                                    361

<210> SEQ ID NO 18
<211> LENGTH: 322
<212> TYPE: DNA
<213> ORGANISM: Homo sapiens
<220> FEATURE:
<221> NAME/KEY: misc_feature
<223> OTHER INFORMATION: clone F11 light chain variable region

<400> SEQUENCE: 18
gaaattgtgt tgacacagtc tccagtcacc ctgtctttgt ctccagggga aagagccacc     60
ctctcctgca gggccagtca gaatgttatc aactccttag tctggtacca acagaaacct    120
ggccaggctc ccaggctcct catctatggt gcatccaaca gggccactgg catcccagcc    180
aggttccgtg gcagtgggtc tgggacagac ttcactctca ccatcgacag cctggagcct    240
gaagacattg cagtttatta ctgtcagcag cgcggcacct ggctttggtc gttcggccaa    300
gggaccaagg tggaaatcaa ac                                             322

<210> SEQ ID NO 19
<211> LENGTH: 385
<212> TYPE: DNA
<213> ORGANISM: Homo sapiens
<220> FEATURE:
<221> NAME/KEY: misc_feature
<223> OTHER INFORMATION: clone H5 heavy chain variable region

<400> SEQUENCE: 19
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagaggggggg    300 gtgaatatag tggctacgat tatttactac tacgctttgg acgtctgggg ccggggccaa    360
gggaccacgg tcaccgtctc ctcag                                          385

<210> SEQ ID NO 20
<211> LENGTH: 352
<212> TYPE: DNA
<213> ORGANISM: Homo sapiens
<220> FEATURE:
<221> NAME/KEY: misc_feature
<223> OTHER INFORMATION: clone H5 light chain variable region

<400> SEQUENCE: 20
cagtctgtgc tgacgcagcc tgcctccgtg tctgggtctc ctggacagtc gatcaccatc     60
tcctgcactg gaaccagcag tgacgttggt ggttataact atgtctcctg gtaccaaatat   120 gtctcctggt accaacaaca cccaggcaaa gccccccaaac tcatgattta tgatgtcagt   180
aatcggccct caggggtttc taatcgcttc tctggctcca agtctggcaa cacggcctcc    240
ctgaccatct ctgggctcca ggctgaggac gaggctgatt attactgcag ctcatataca    300
agcagcagca ctcaggtggt attcggcgga gggaccaagc tgaccgtcct ag            352
```

```
<210> SEQ ID NO 21
<211> LENGTH: 232
<212> TYPE: DNA
<213> ORGANISM: Homo sapiens
<220> FEATURE:
<221> NAME/KEY: misc_feature
<223> OTHER INFORMATION: cis element

<400> SEQUENCE: 21
gcaggattta gggcttggtc tctcagcatc ccacacttgt acagctgatg tggcatctgt      60
gttttcttcc tcatcgtaga tcaggctttg agctgtgaaa taccctgcct catgcatatg     120
caaataacct gaggtcttct gagataaata tagatatatt ggtgccctga gagcatcaca     180
taacaaccac attcctcctc taaagaagcc cctgggagca cagctcatca cc             232

<210> SEQ ID NO 22
<211> LENGTH: 126
<212> TYPE: DNA
<213> ORGANISM: Homo sapiens
<220> FEATURE:
<221> NAME/KEY: misc_feature
<223> OTHER INFORMATION: cis element #1

<400> SEQUENCE: 22
tcgtcggagc agacgggagt ttctcctcgg ggtcggagca ggaggcacgc ggagtgtgag      60
gccacgcatg agcggacgct aaccccctcc ccagccacaa agagtctaca tgtctagggt     120
ctagac                                                                126

<210> SEQ ID NO 23
<211> LENGTH: 266
<212> TYPE: DNA
<213> ORGANISM: Homo sapiens
<220> FEATURE:
<221> NAME/KEY: misc_feature
<223> OTHER INFORMATION: cis element #2

<400> SEQUENCE: 23
gcccgcgccg gctgtgctgc acaggggag gagagggaac cccaggcgcg agcgggaaga       60
ggggacctgc agccacaact tctctggtcc tctgcatccc ttctgtccct ccaccgtcc      120 ccttccccac cctctggccc ccaccttctt ggaggcgaca accccggga ggcattagaa      180 gggatttttc ccgcaggttg cgaagggaag caaacttggt ggcaacttgc ctcccggtgc    240
gggcgtctct cccccaccgt ctcaac                                          266

<210> SEQ ID NO 24
<211> LENGTH: 497
<212> TYPE: DNA
<213> ORGANISM: Homo sapiens
<220> FEATURE:
<221> NAME/KEY: misc_feature
<223> OTHER INFORMATION: J chain

<400> SEQUENCE: 24
ctcgagacca tgaagaacca tttgctttc tggggagtcc tggcggtttt tattaaggct       60
gttcatgtga aagcccaaga agatgaaagg attgttcttg ttgacaacaa atgtaagtgt    120
gcccggatta cttccaggat catccgttct tccgaagatc taatgagga cattgtggag     180 agaaacatcc gaattattgt tcctctgaac aacagggaga atatctctga tcccacctca    240
ccattgagaa ccagatttgt gtaccatttg tctgacctct gtaaaaaatg tgatcctaca    300
gaagtggagc tggataatca gatagttact gctacccaga gcaatatctg tgatgaagac    360
```

```
agtgctacag agacctgcta cacttatgac agaaacaagt gctacacagc tgtggtccca      420
ctcgtatatg gtggtgagac caaaatggtg gaaacagcct taaccccaga tgcctgctat      480
cctgactaag cggccgc                                                     497

<210> SEQ ID NO 25
<211> LENGTH: 1886
<212> TYPE: DNA
<213> ORGANISM: Homo sapiens
<220> FEATURE:
<221> NAME/KEY: misc_feature
<223> OTHER INFORMATION: secretory component

<400> SEQUENCE: 25
ctcgagacca tgctgctctt cgtgctcacc tgcctgctgg cggtcttccc agccatctcc       60
acgaagagtc ccatatttgg tcccgaggag gtgaatagtg tggaaggtaa ctcagtgtcc      120
atcacgtgct actacccacc cacctctgtc aaccggcaca cccggaagta ctggtgccgg      180
cagggagcta gaggtggctg cataaccctc atctcctcgg agggctacgt ctccagcaaa      240
tatgcaggca gggctaacct caccaacttc ccggagaacg gcacatttgt ggtgaacatt      300
gcccagctga gccaggatga ctcccgggcg tacaagtgtg gcctgggcat caatagccga      360
ggcctgtcct ttgatgtcag cctggaggtc agccagggtc ctgggctcct aaatgacact      420
aaagtctaca cagtggacct gggcagaacg gtgaccatca actgcccttt caagactgag      480
aatgctcaaa agaggaagtc cttgtacaag cagataggcc tgtaccctgt gctggtcatc      540
gactccagtg gttatgtaaa tcccaactat acaggaagaa tacgccttga tattcagggt      600
actggccagt tactgttcag cgttgtcatc aaccaactca ggctcagcga tgctgggcag      660
tatctctgcc aggctgggga tgattccaat agtaataaga gaatgctga ccctccaagtg      720 ctaaagcccg agcccgagct ggtttatgaa gacctgaggg gctcagtgac cttccactgt      780
gccctgggcc ctgaggtggc aaacgtggcc aaatttctgt gccgacagag cagtgggaa      840 aactgtgacg tggtcgtcaa caccctgggg aagagggccc cagcctttga gggcaggatc      900
ctgctcaacc cccaggacaa ggatggctca ttcagtgtgg tgatcacagg cctgaggaag      960
gaggatgcag ggcgctacct gtgtggagcc cattcggatg gtcagctgca ggaaggctcg     1020
cctatccagg cctggcaact cttcgtcaat gaggagtcca cgattccccg cagccccact     1080
gtggtgaagg gggtggcagg aggctctgtg ccgtgctct gccctacaa ccgtaaggaa     1140 agcaaaagca tcaagtactg gtgtctctgg aaggggccc agaatggccg ctgcccctg     1200 ctggtggaca gcgagggtg ggttaaggcc cagtacgagg gccgcctctc cctgctggag     1260
gagccaggca acggcacctt cactgtcatc ctcaaccagc tcaccagccg ggacgccggc     1320
ttctactggt gtctgaccaa cggcgatact ctctggagga ccaccgtgga gatcaagatt     1380
atcgaaggag aaccaaacct caaggtacca gggaatgtca cggctgtgct gggagagact     1440
ctcaaggtcc cctgtcactt tccatgcaaa ttctcctcgt acgagaaata ctggtgcaag     1500
tggaataaca cgggctgcca ggccctgccc agccaagacg aaggcccag caaggccttc     1560 gtgaactgtg acgagaacag ccggcttgtc ccctgaccc tgaacctggt gaccagggct     1620
gatgagggct ggtactggtg tggagtgaag cagggccact ctatggaga gactgcagcc     1680 gtctatgtgg cagttgaaga gaggaaggca gcgggtccc gcgatgtcag cctagcgaag     1740
gcagacgctc tcctgatga aaggtgcta gactctggtt ttcggagat tgagaacaaa     1800 gccattcagg atcccaggct ttttgcagag aagcttctgg tgcctcgcgg ttcccctcac     1860
```
caccaccacc accactaagc ggccgc                                          1886

<210> SEQ ID NO 26
<211> LENGTH: 40
<212> TYPE: PRT
<213> ORGANISM: Artificial Sequence
<220> FEATURE:
<223> OTHER INFORMATION: synthesized foldon and thrombin cleavage site

<400> SEQUENCE: 26

Arg Ser Arg Ser Leu Val Pro Arg Gly Ser Pro Gly Ser Gly Tyr Ile
1               5                   10                  15

Pro Glu Ala Pro Arg Asp Gly Gln Ala Tyr Val Arg Lys Asp Gly Glu
            20                  25                  30

Trp Val Leu Leu Ser Thr Phe Leu
        35                  40

<210> SEQ ID NO 27
<211> LENGTH: 8
<212> TYPE: PRT
<213> ORGANISM: Artificial Sequence
<220> FEATURE:
<223> OTHER INFORMATION: synthesized Strep-tag

<400> SEQUENCE: 27

Trp Ser His Pro Gln Phe Glu Lys
1               5

<210> SEQ ID NO 28
<211> LENGTH: 1074
<212> TYPE: DNA
<213> ORGANISM: Artificial Sequence
<220> FEATURE:
<223> OTHER INFORMATION: synthesized IgA1H-NRE

<400> SEQUENCE: 28
gctagcccta cctcccccaa ggtgttcccc ctgtccctgt gctctaccca gcctgacggc        60
aacgtcgtga tcgcctgtct ggtgcaggga ttctttccac aagagcccct gtccgtgact       120
tggagcgaat ctggccaggg cgtgaccgcg cgcaacttcc caccttctca ggacgcctcc       180
ggcgacctct acaccacctc gagtcagctg accctgcccg ccacccagtg tctggctggc       240
aagtctgtga cctgccacgt gaagcactac accaaccccc tccaggatgt gaccgtgcct       300
tgccctgtgc cttccacccc tcctaccct agcccttcta caccccccac cccttcccca        360
tcttgctgcc accctcgctt aagcctgcac agacccgccc tggaggatct gctgctggga       420
tccgaggcca acctgacctg taccctgacc ggcctgagag atgcctctgg cgtgaccttc       480
acctggaccc cttccagcgg aaagtccgct gtgcagggcc ccctgagag ggacctgtgc        540 ggctgctact ctgtgtcctc cgtgctgccc gggtgcgccg agccttggaa tcacggcaag       600 accttacct gcaccgccgc ttaccccgag tccaagaccc tctctgaccgc caccctgtcc       660 aagtccggca caccttccg gcccgaagtg catctgctgc cccctccatc tgaggaactg       720
gccctgaacg agctcgtgac cctgacatgc ctggctcggg gcttcagccc taaggatgtg       780
ctcgtgcgtt ggctgcaggg ctcccaggaa ctgcccagag agaagtatct gacctgggcc       840
tcgcgacagg aaccttccca gggcacaacc accttcgccg tgacctctat cctacgcgtg       900
gccgccgagg actggaagaa gggcgacacc ttcagctgca tggtgggaca cgaggccctg       960
ccactggcct tcacccagaa aacaattgac cggctggccg gcaagcccac ccatgtgaat      1020

```
gtgtccgtcg tgatggccga ggtggacggc acctgttact gagtatacaa gctt        1074
```

```
<210> SEQ ID NO 29
<211> LENGTH: 1041
<212> TYPE: DNA
<213> ORGANISM: Artificial Sequence
<220> FEATURE:
<223> OTHER INFORMATION: synthesized IgA2m2H-NRE

<400> SEQUENCE: 29
gctagcgcta gccctacctc ccccaaggtg ttccctctgt ccctggacag cacccccag     60
gatggcaatg tggtggtggc ctgtctggtg cagggattct ttccacaaga gcccctgtcc   120
gtgacttgga gcgagtccgg ccagaacgtg accgcgcgca acttcccacc tagccaggac   180
gcctccggcg acctgtacac cacctcgagt cagctgaccc tgcccgccac ccagtgccct   240
gatggcaagt ctgtgacctg ccacgtgaag cactacacca actcctccca ggatgtgacc   300
gtgccttgca gagtgccccc tcctcctcct tgctgccacc ctcgcttaag tctgcacaga   360
cccgccctgg aagatctgct gctgggatcc gaggccaacc tgacctgtac cctgaccggc   420
ctgagagatg cctctggcgc caccttttacc tggacccctt ccagcggaaa gtccgccgtg   480
caggggcccc ctgagaggga cctgtgcggc tgctactccg tgtcctctgt gctgcccggg   540
tgtgcccagc cttggaacca cggcgagaca ttcacctgta ccgccgctca ccccgagctg   600
aaaacccctc tgaccgccaa catcaccaag tccggcaaca ccttccggcc cgaagtgcat   660
ctgctgcccc caccttccga ggaactggcc ctgaacgagc tcgtgaccct gacatgcctg   720
gccagaggct tcagcccaaa ggatgtgctc gtgcggtggc tgcagggctc caggaactg    780
cccagagaga agtatctgac ctgggcctcg cgacaggaac cttctcaggg caccacaacc   840
tacgccgtga cctccatcct acgcgtgcc ggcgaggact ggaagaaggg cgagactttc    900
tcctgcatgg tgggacacga ggccctgcca ctggccttca cccagaaaac aattgaccgg   960
atggccggca gcccacccca catcaatgtg tccgtcgtga tggccgaggc cgacggcacc  1020
tgttactgag tatacaagct t                                            1041
```

```
<210> SEQ ID NO 30
<211> LENGTH: 503
<212> TYPE: DNA
<213> ORGANISM: Artificial Sequence
<220> FEATURE:
<223> OTHER INFORMATION: synthesized J-chain named JCNQ

<400> SEQUENCE: 30
ctcgaggccg ccaccatgaa gaaccatctg ctgttctggg gcgtgctggc cgtgttcatc    60
aaggccgtgc acgtgaaggc ccaggaagat gagcggatcg tgctggtgga caacaagtgc   120
aagtgcgccc ggatcacctc ccggatcatc cggtccagcg aggaccccaa cgaggacatc   180
gtggaacggc aaatcagaat catcgtgccc ctgaacaacc gcgagaacat ctccgaccct   240
acctccccac tgcggaccag attcgtgtac cacctgtccg acctgtgcaa gaagtgcgac   300
cccaccgagg tggaactgga caaccagatc gtgaccgcca cccagtccaa catctgcgac   360
gaggactccg ccaccgagac atgctacacc tacgaccgga caagtgcta caccgccgtg   420
gtgcctctgg tgtacggcgg cgagacaaag atggtggaaa ccgccctgac ccccgacgcc   480
tgctaccctg attgagcggc cgc                                          503
```

```
<210> SEQ ID NO 31
<211> LENGTH: 1892
```

<212> TYPE: DNA
<213> ORGANISM: Artificial Sequence
<220> FEATURE:
<223> OTHER INFORMATION: synthesized secretory component named SCNQ

<400> SEQUENCE: 31

```
ctcgaggccg ccaccatgct gctgttcgtg ctgacctgtc tgctggccgt gttccccgcc      60
atctccacca gagccctat cttcggcccc gaggaagtga actccgtgga aggcaactcc      120
gtgtccatca cctgttacta cccccccacc tccgtgaacc ggcacacgcg taagtactgg      180
tgccggcagg gtgccagagg cggctgtatc accctgatct ccagcgaggg ctacgtgtcc      240
tctaagtacg ccggcagagc ccaactgacc aacttccccg agcaaggcac cttcgtcgtg      300
aatatcgccc agctgtccca ggacgactcc ggcagataca agtgcggcct gggcatcaac      360
tctcggggcc tgtctttcga cgtgtccctc gaggtgtctc agggcccagg cctgctgcaa      420
gacaccaagg tgtacacagt ggacctgggc cggaccgtga ccatcaactg ccccttcaag      480
accgagaacg cccagaagcg gaagtccctg tacaagcaga tcggcctgta ccccgtgctc      540
gtgatcgact cctccggcta cgtgaacccc caatacaccg gtcggatcag actggacatc      600
cagggcacag acagctgct gttttccgtc gtgatcaacc agctgcggct gtccgatgcc      660
ggccagtacc tgtgtcaggc cggcgacgac tccaactcca acaagaagaa cgctgatctg      720
caggtgctga gcccgagcc cgagctggtg tacgaggacc tgagaggctc cgtgacccttt      780
cactgcgccc tgggacctga ggtggccaac gtggccaagt tcctgtgcag acagtcctcc      840
ggcgagaact gcgacgtggt cgtgaacacc ctgggcaaga gagcccctgc cttcgagggc      900
agaatcctgc tgaatcccca ggacaaggac ggctccttct ccgtcgtgat taccggcctg      960
cggaaagagg acgctggcag atacctgtgt ggcgcccact ctgatggcca gctgcaggaa      1020
ggcagcccca tccaggcttg cagctgtttt gtgaacgagg aatccaccat ccccagatct      1080
cccaccgtcg tgaaggcgt ggcagggga tctgtggccg tgctgtgccc ctacaaccgg      1140
aaagagtcca agtccatcaa gtattggtgc ctgtgggagg gcgcccagaa cggcagatgt      1200
cctctgctgg tggactccga gggctgggtc aaggctcagt atgagggccg gctgtccctg      1260
ctggaagaac ctggccaagg caccttcacc gtgatcctga accagctgac tagtcgggac      1320
gccggcttct actggtgtct gaccaacggc gataccctgt ggcggaccac cgtggaaatc      1380
aagatcatcg agggcgagcc caacctgaaa gtgcccggcc aagtgaccgc cgtgctgggc      1440
gaaacactga ggtgccctg ccacttcccc tgcaagttct ccagctacga gaaatattgg      1500
tgcaagtggc aaaacaccgg ctgccaggcc ctgcctagcc aggatgaggg accttccaag      1560
gccttcgtga actgtgacga gaactcccgg ctggtgtccc tgaccctgaa cctcgtgacc      1620
agagccgatg agggctggta ttggtgtggc gtgaagcagg gccacttcta cggcgagaca      1680
gccgctgtgt acgtggccgt ggaagagaga aaggccgctg ctctcgggga tgtgtctctg      1740
gccaaggctg atgccgcccc tgacgagaag gtgctggact ccggcttcag agagatcgag      1800
aacaaggcca tccaggaccc gcggctgttc gccgaaaagc ttctggtgcc tcggggctcc      1860
cctcaccacc accatcacca ttgagcggcc gc                                   1892
```

<210> SEQ ID NO 32
<211> LENGTH: 86
<212> TYPE: DNA
<213> ORGANISM: Artificial Sequence
<220> FEATURE:
<223> OTHER INFORMATION: synthesized V458I linker

```
<400> SEQUENCE: 32
aattgaccgg ctggccggca agcccaccca tattaatgtg tccgtcgtga tggccgaggt    60
ggacggcacc tgttactgag tataca                                         86

<210> SEQ ID NO 33
<211> LENGTH: 86
<212> TYPE: DNA
<213> ORGANISM: Artificial Sequence
<220> FEATURE:
<223> OTHER INFORMATION: synthesized V458I linker

<400> SEQUENCE: 33
agcttgtata ctcagtaaca ggtgccgtcc acctcggcca tcacgacgga cacattaata    60
tgggtgggct tgccggccag ccggtc                                         86

<210> SEQ ID NO 34
<211> LENGTH: 86
<212> TYPE: DNA
<213> ORGANISM: Artificial Sequence
<220> FEATURE:
<223> OTHER INFORMATION: synthesized V458A linker

<400> SEQUENCE: 34
aattgaccgg ctggccggca agcccaccca tgccaatgtg tccgtcgtga tggccgaggt    60
ggacggcacc tgttactgag tataca                                         86

<210> SEQ ID NO 35
<211> LENGTH: 86
<212> TYPE: DNA
<213> ORGANISM: Artificial Sequence
<220> FEATURE:
<223> OTHER INFORMATION: synthesized V458A linker

<400> SEQUENCE: 35
agcttgtata ctcagtaaca ggtgccgtcc acctcggcca tcacgacgga cacattggca    60
tgggtgggct tgccggccag ccggtc                                         86

<210> SEQ ID NO 36
<211> LENGTH: 86
<212> TYPE: DNA
<213> ORGANISM: Artificial Sequence
<220> FEATURE:
<223> OTHER INFORMATION: synthesized V458W linker

<400> SEQUENCE: 36
aattgaccgg ctggccggca agcccaccca ttggaatgtg tccgtcgtga tggccgaggt    60
ggacggcacc tgttactgag tataca                                         86

<210> SEQ ID NO 37
<211> LENGTH: 86
<212> TYPE: DNA
<213> ORGANISM: Artificial Sequence
<220> FEATURE:
<223> OTHER INFORMATION: synthesized V458W linker

<400> SEQUENCE: 37
agcttgtata ctcagtaaca ggtgccgtcc acctcggcca tcacgacgga cacattccaa    60
tgggtgggct tgccggccag ccggtc                                         86

<210> SEQ ID NO 38
<211> LENGTH: 86
```

```
<212> TYPE: DNA
<213> ORGANISM: Artificial Sequence
<220> FEATURE:
<223> OTHER INFORMATION: synthesized V458C linker

<400> SEQUENCE: 38
aattgaccgg ctggccggca agcccaccca ttgtaatgtg tccgtcgtga tggccgaggt    60
ggacggcacc tgttactgag tataca                                        86

<210> SEQ ID NO 39
<211> LENGTH: 86
<212> TYPE: DNA
<213> ORGANISM: Artificial Sequence
<220> FEATURE:
<223> OTHER INFORMATION: synthesized V458C linker

<400> SEQUENCE: 39
agcttgtata ctcagtaaca ggtgccgtcc acctcggcca tcacgacgga cacattacaa    60
tgggtgggct tgccggccag ccggtc                                        86

<210> SEQ ID NO 40
<211> LENGTH: 86
<212> TYPE: DNA
<213> ORGANISM: Artificial Sequence
<220> FEATURE:
<223> OTHER INFORMATION: synthesized V458D linker

<400> SEQUENCE: 40
aattgaccgg ctggccggca agcccaccca tgacaatgtg tccgtcgtga tggccgaggt    60
ggacggcacc tgttactgag tataca                                        86

<210> SEQ ID NO 41
<211> LENGTH: 86
<212> TYPE: DNA
<213> ORGANISM: Artificial Sequence
<220> FEATURE:
<223> OTHER INFORMATION: synthesized V458D linker

<400> SEQUENCE: 41
agcttgtata ctcagtaaca ggtgccgtcc acctcggcca tcacgacgga cacattacaa    60
tgggtgggct tgccggccag ccggtc                                        86

<210> SEQ ID NO 42
<211> LENGTH: 86
<212> TYPE: DNA
<213> ORGANISM: Artificial Sequence
<220> FEATURE:
<223> OTHER INFORMATION: synthesized V458E linker

<400> SEQUENCE: 42
aattgaccgg ctggccggca agcccaccca tgagaatgtg tccgtcgtga tggccgaggt    60
ggacggcacc tgttactgag tataca                                        86

<210> SEQ ID NO 43
<211> LENGTH: 86
<212> TYPE: DNA
<213> ORGANISM: Artificial Sequence
<220> FEATURE:
<223> OTHER INFORMATION: synthesized V458E linker

<400> SEQUENCE: 43
agcttgtata ctcagtaaca ggtgccgtcc acctcggcca tcacgacgga cacattgtca    60
```
tgggtgggct tgccggccag ccggtc                                            86

<210> SEQ ID NO 44
<211> LENGTH: 86
<212> TYPE: DNA
<213> ORGANISM: Artificial Sequence
<220> FEATURE:
<223> OTHER INFORMATION: synthesized V458F linker

<400> SEQUENCE: 44
aattgaccgg ctggccggca agcccaccca ttttaatgtg tccgtcgtga tggccgaggt      60
ggacggcacc tgttactgag tataca                                            86

<210> SEQ ID NO 45
<211> LENGTH: 86
<212> TYPE: DNA
<213> ORGANISM: Artificial Sequence
<220> FEATURE:
<223> OTHER INFORMATION: synthesized V458F linker

<400> SEQUENCE: 45
agcttgtata ctcagtaaca ggtgccgtcc acctcggcca tcacgacgga cacattctca      60
tgggtgggct tgccggccag ccggtc                                            86

<210> SEQ ID NO 46
<211> LENGTH: 86
<212> TYPE: DNA
<213> ORGANISM: Artificial Sequence
<220> FEATURE:
<223> OTHER INFORMATION: synthesized V458G linker

<400> SEQUENCE: 46
aattgaccgg ctggccggca agcccaccca tggcaatgtg tccgtcgtga tggccgaggt      60
ggacggcacc tgttactgag tataca                                            86

<210> SEQ ID NO 47
<211> LENGTH: 86
<212> TYPE: DNA
<213> ORGANISM: Artificial Sequence
<220> FEATURE:
<223> OTHER INFORMATION: synthesized V458G linker

<400> SEQUENCE: 47
agcttgtata ctcagtaaca ggtgccgtcc acctcggcca tcacgacgga cacattaaaa      60
tgggtgggct tgccggccag ccggtc                                            86

<210> SEQ ID NO 48
<211> LENGTH: 86
<212> TYPE: DNA
<213> ORGANISM: Artificial Sequence
<220> FEATURE:
<223> OTHER INFORMATION: synthesized V458H linker

<400> SEQUENCE: 48
aattgaccgg ctggccggca agcccaccca tcataatgtg tccgtcgtga tggccgaggt      60
ggacggcacc tgttactgag tataca                                            86

<210> SEQ ID NO 49
<211> LENGTH: 86
<212> TYPE: DNA
<213> ORGANISM: Artificial Sequence
<220> FEATURE:
<223> OTHER INFORMATION: synthesized V458H linker

<400> SEQUENCE: 49
agcttgtata ctcagtaaca ggtgccgtcc acctcggcca tcacgacgga cacattatga    60
tgggtgggct tgccggccag ccggtc                                        86

<210> SEQ ID NO 50
<211> LENGTH: 86
<212> TYPE: DNA
<213> ORGANISM: Artificial Sequence
<220> FEATURE:
<223> OTHER INFORMATION: synthesized V458K linker

<400> SEQUENCE: 50
aattgaccgg ctggccggca agcccaccca taagaatgtg tccgtcgtga tggccgaggt    60
ggacggcacc tgttactgag tataca                                        86

<210> SEQ ID NO 51
<211> LENGTH: 86
<212> TYPE: DNA
<213> ORGANISM: Artificial Sequence
<220> FEATURE:
<223> OTHER INFORMATION: synthesized V458K linker

<400> SEQUENCE: 51
agcttgtata ctcagtaaca ggtgccgtcc acctcggcca tcacgacgga cacattctta    60
tgggtgggct tgccggccag ccggtc                                        86

<210> SEQ ID NO 52
<211> LENGTH: 86
<212> TYPE: DNA
<213> ORGANISM: Artificial Sequence
<220> FEATURE:
<223> OTHER INFORMATION: synthesized V458L linker

<400> SEQUENCE: 52
aattgaccgg ctggccggca agcccaccca tctgaatgtg tccgtcgtga tggccgaggt    60
ggacggcacc tgttactgag tataca                                        86

<210> SEQ ID NO 53
<211> LENGTH: 86
<212> TYPE: DNA
<213> ORGANISM: Artificial Sequence
<220> FEATURE:
<223> OTHER INFORMATION: synthesized V458L linker

<400> SEQUENCE: 53
agcttgtata ctcagtaaca ggtgccgtcc acctcggcca tcacgacgga cacattcaga    60
tgggtgggct tgccggccag ccggtc                                        86

<210> SEQ ID NO 54
<211> LENGTH: 86
<212> TYPE: DNA
<213> ORGANISM: Artificial Sequence
<220> FEATURE:
<223> OTHER INFORMATION: synthesized V458M linker

<400> SEQUENCE: 54
aattgaccgg ctggccggca agcccaccca tatgaatgtg tccgtcgtga tggccgaggt    60
ggacggcacc tgttactgag tataca                                        86

<210> SEQ ID NO 55

<210> SEQ ID NO 56
<211> LENGTH: 86
<212> TYPE: DNA
<213> ORGANISM: Artificial Sequence
<220> FEATURE:
<223> OTHER INFORMATION: synthesized V458M linker

<400> SEQUENCE: 55
agcttgtata ctcagtaaca ggtgccgtcc acctcggcca tcacgacgga cacattcata    60
tgggtgggct tgccggccag ccggtc    86

<210> SEQ ID NO 56
<211> LENGTH: 86
<212> TYPE: DNA
<213> ORGANISM: Artificial Sequence
<220> FEATURE:
<223> OTHER INFORMATION: synthesized V458N linker

<400> SEQUENCE: 56
aattgaccgg ctggccggca agcccaccca taataatgtg tccgtcgtga tggccgaggt    60
ggacggcacc tgttactgag tataca    86

<210> SEQ ID NO 57
<211> LENGTH: 86
<212> TYPE: DNA
<213> ORGANISM: Artificial Sequence
<220> FEATURE:
<223> OTHER INFORMATION: synthesized V458N linker

<400> SEQUENCE: 57
agcttgtata ctcagtaaca ggtgccgtcc acctcggcca tcacgacgga cacattatta    60
tgggtgggct tgccggccag ccggtc    86

<210> SEQ ID NO 58
<211> LENGTH: 86
<212> TYPE: DNA
<213> ORGANISM: Artificial Sequence
<220> FEATURE:
<223> OTHER INFORMATION: synthesized V458P linker

<400> SEQUENCE: 58
aattgaccgg ctggccggca agcccaccca tcccaatgtg tccgtcgtga tggccgaggt    60
ggacggcacc tgttactgag tataca    86

<210> SEQ ID NO 59
<211> LENGTH: 86
<212> TYPE: DNA
<213> ORGANISM: Artificial Sequence
<220> FEATURE:
<223> OTHER INFORMATION: synthesized V458P linker

<400> SEQUENCE: 59
agcttgtata ctcagtaaca ggtgccgtcc acctcggcca tcacgacgga cacattggga    60
tgggtgggct tgccggccag ccggtc    86

<210> SEQ ID NO 60
<211> LENGTH: 86
<212> TYPE: DNA
<213> ORGANISM: Artificial Sequence
<220> FEATURE:
<223> OTHER INFORMATION: synthesized V458Q linker

<400> SEQUENCE: 60
aattgaccgg ctggccggca agcccaccca tcagaatgtg tccgtcgtga tggccgaggt    60
ggacggcacc tgttactgag tataca            86

<210> SEQ ID NO 61
<211> LENGTH: 86
<212> TYPE: DNA
<213> ORGANISM: Artificial Sequence
<220> FEATURE:
<223> OTHER INFORMATION: synthesized V458Q linker

<400> SEQUENCE: 61
agcttgtata ctcagtaaca ggtgccgtcc acctcggcca tcacgacgga cacattctga   60
tgggtgggct gccggccag ccggtc            86

<210> SEQ ID NO 62
<211> LENGTH: 86
<212> TYPE: DNA
<213> ORGANISM: Artificial Sequence
<220> FEATURE:
<223> OTHER INFORMATION: synthesized V458R linker

<400> SEQUENCE: 62
aattgaccgg ctggccggca agcccaccca tcggaatgtg tccgtcgtga tggccgaggt   60
ggacggcacc tgttactgag tataca            86

<210> SEQ ID NO 63
<211> LENGTH: 86
<212> TYPE: DNA
<213> ORGANISM: Artificial Sequence
<220> FEATURE:
<223> OTHER INFORMATION: synthesized V458R linker

<400> SEQUENCE: 63
agcttgtata ctcagtaaca ggtgccgtcc acctcggcca tcacgacgga cacattccga   60
tgggtgggct gccggccag ccggtc            86

<210> SEQ ID NO 64
<211> LENGTH: 86
<212> TYPE: DNA
<213> ORGANISM: Artificial Sequence
<220> FEATURE:
<223> OTHER INFORMATION: synthesized V458S linker

<400> SEQUENCE: 64
aattgaccgg ctggccggca agcccaccca ttccaatgtg tccgtcgtga tggccgaggt   60
ggacggcacc tgttactgag tataca            86

<210> SEQ ID NO 65
<211> LENGTH: 86
<212> TYPE: DNA
<213> ORGANISM: Artificial Sequence
<220> FEATURE:
<223> OTHER INFORMATION: synthesized V458S linker

<400> SEQUENCE: 65
agcttgtata ctcagtaaca ggtgccgtcc acctcggcca tcacgacgga cacattggaa   60
tgggtgggct gccggccag ccggtc            86

<210> SEQ ID NO 66
<211> LENGTH: 86
<212> TYPE: DNA
<213> ORGANISM: Artificial Sequence
<220> FEATURE:

<223> OTHER INFORMATION: synthesized V458T linker

<400> SEQUENCE: 66
aattgaccgg ctggccggca agcccaccca taccaatgtg tccgtcgtga tggccgaggt    60
ggacggcacc tgttactgag tataca    86

<210> SEQ ID NO 67
<211> LENGTH: 86
<212> TYPE: DNA
<213> ORGANISM: Artificial Sequence
<220> FEATURE:
<223> OTHER INFORMATION: synthesized V458T linker

<400> SEQUENCE: 67
agcttgtata ctcagtaaca ggtgccgtcc acctcggcca tcacgacgga cacattggta    60
tgggtgggct tgccggccag ccggtc    86

<210> SEQ ID NO 68
<211> LENGTH: 86
<212> TYPE: DNA
<213> ORGANISM: Artificial Sequence
<220> FEATURE:
<223> OTHER INFORMATION: synthesized V458Y linker

<400> SEQUENCE: 68
aattgaccgg ctggccggca agcccaccca ttacaatgtg tccgtcgtga tggccgaggt    60
ggacggcacc tgttactgag tataca    86

<210> SEQ ID NO 69
<211> LENGTH: 86
<212> TYPE: DNA
<213> ORGANISM: Artificial Sequence
<220> FEATURE:
<223> OTHER INFORMATION: synthesized V458Y linker

<400> SEQUENCE: 69
agcttgtata ctcagtaaca ggtgccgtcc acctcggcca tcacgacgga cacattgtaa    60
tgggtgggct tgccggccag ccggtc    86

<210> SEQ ID NO 70
<211> LENGTH: 15
<212> TYPE: PRT
<213> ORGANISM: Homo sapiens

<400> SEQUENCE: 70

Tyr Ala Ala Ser Ser Tyr Leu Ser Leu Thr Pro Glu Gln Trp Lys
1               5                   10                  15

<210> SEQ ID NO 71
<211> LENGTH: 15
<212> TYPE: PRT
<213> ORGANISM: Homo sapiens
<220> FEATURE:
<221> NAME/KEY: misc_feature
<222> LOCATION: (15)..(15)
<223> OTHER INFORMATION: labeled with stable isotope

<400> SEQUENCE: 71

Tyr Ala Ala Ser Ser Tyr Leu Ser Leu Thr Pro Glu Gln Trp Lys
1               5                   10                  15

<210> SEQ ID NO 72
<211> LENGTH: 15

```
<212> TYPE: PRT
<213> ORGANISM: Homo sapiens

<400> SEQUENCE: 72

Ser Tyr Ser Cys Gln Val Thr His Glu Gly Ser Thr Val Glu Lys
1               5                   10                  15

<210> SEQ ID NO 73
<211> LENGTH: 15
<212> TYPE: PRT
<213> ORGANISM: Homo sapiens
<220> FEATURE:
<221> NAME/KEY: misc_feature
<222> LOCATION: (15)..(15)
<223> OTHER INFORMATION: labeled with stable isotope

<400> SEQUENCE: 73

Ser Tyr Ser Cys Gln Val Thr His Glu Gly Ser Thr Val Glu Lys
1               5                   10                  15

<210> SEQ ID NO 74
<211> LENGTH: 16
<212> TYPE: PRT
<213> ORGANISM: Homo sapiens

<400> SEQUENCE: 74

Ser Gly Thr Ala Ser Val Val Cys Leu Leu Asn Asn Phe Tyr Pro Arg
1               5                   10                  15

<210> SEQ ID NO 75
<211> LENGTH: 16
<212> TYPE: PRT
<213> ORGANISM: Homo sapiens
<220> FEATURE:
<221> NAME/KEY: misc_feature
<222> LOCATION: (16)..(16)
<223> OTHER INFORMATION: labeled with stable isotope

<400> SEQUENCE: 75

Ser Gly Thr Ala Ser Val Val Cys Leu Leu Asn Asn Phe Tyr Pro Arg
1               5                   10                  15

<210> SEQ ID NO 76
<211> LENGTH: 14
<212> TYPE: PRT
<213> ORGANISM: Homo sapiens

<400> SEQUENCE: 76

Asp Ser Thr Tyr Ser Leu Ser Ser Thr Leu Thr Leu Ser Lys
1               5                   10

<210> SEQ ID NO 77
<211> LENGTH: 14
<212> TYPE: PRT
<213> ORGANISM: Homo sapiens
<220> FEATURE:
<221> NAME/KEY: misc_feature
<222> LOCATION: (14)..(14)
<223> OTHER INFORMATION: labeled with stable isotope

<400> SEQUENCE: 77

Asp Ser Thr Tyr Ser Leu Ser Ser Thr Leu Thr Leu Ser Lys
1               5                   10

<210> SEQ ID NO 78
<211> LENGTH: 10
<212> TYPE: PRT
```

<213> ORGANISM: Homo sapiens

<400> SEQUENCE: 78

Trp Leu Gln Gly Ser Gln Glu Leu Pro Arg
1               5                   10

<210> SEQ ID NO 79
<211> LENGTH: 10
<212> TYPE: PRT
<213> ORGANISM: Homo sapiens
<220> FEATURE:
<221> NAME/KEY: misc_feature
<222> LOCATION: (10)..(10)
<223> OTHER INFORMATION: labeled with stable isotope

<400> SEQUENCE: 79

Trp Leu Gln Gly Ser Gln Glu Leu Pro Arg
1               5                   10

<210> SEQ ID NO 80
<211> LENGTH: 7
<212> TYPE: PRT
<213> ORGANISM: Homo sapiens

<400> SEQUENCE: 80

Tyr Leu Thr Trp Ala Ser Arg
1               5

<210> SEQ ID NO 81
<211> LENGTH: 7
<212> TYPE: PRT
<213> ORGANISM: Homo sapiens
<220> FEATURE:
<221> NAME/KEY: misc_feature
<222> LOCATION: (7)..(7)
<223> OTHER INFORMATION: labeled with stable isotope

<400> SEQUENCE: 81

Tyr Leu Thr Trp Ala Ser Arg
1               5

<210> SEQ ID NO 82
<211> LENGTH: 30
<212> TYPE: PRT
<213> ORGANISM: Homo sapiens

<400> SEQUENCE: 82

Asn Phe Pro Pro Ser Gln Asp Ala Ser Gly Asp Leu Tyr Thr Thr Ser
1               5                   10                  15

Ser Gln Leu Thr Leu Pro Ala Thr Gln Cys Leu Ala Gly Lys
            20                  25                  30

<210> SEQ ID NO 83
<211> LENGTH: 30
<212> TYPE: PRT
<213> ORGANISM: Homo sapiens
<220> FEATURE:
<221> NAME/KEY: misc_feature
<222> LOCATION: (30)..(30)
<223> OTHER INFORMATION: labeled with stable isotope

<400> SEQUENCE: 83

Asn Phe Pro Pro Ser Gln Asp Ala Ser Gly Asp Leu Tyr Thr Thr Ser
1               5                   10                  15

Ser Gln Leu Thr Leu Pro Ala Thr Gln Cys Leu Ala Gly Lys
            20                  25                  30

```
<210> SEQ ID NO 84
<211> LENGTH: 15
<212> TYPE: PRT
<213> ORGANISM: Homo sapiens

<400> SEQUENCE: 84

Asp Ala Ser Gly Val Thr Phe Thr Trp Thr Pro Ser Ser Gly Lys
1               5                   10                  15

<210> SEQ ID NO 85
<211> LENGTH: 15
<212> TYPE: PRT
<213> ORGANISM: Homo sapiens
<220> FEATURE:
<221> NAME/KEY: misc_feature
<222> LOCATION: (15)..(15)
<223> OTHER INFORMATION: labeled with stable isotope

<400> SEQUENCE: 85

Asp Ala Ser Gly Val Thr Phe Thr Trp Thr Pro Ser Ser Gly Lys
1               5                   10                  15

<210> SEQ ID NO 86
<211> LENGTH: 30
<212> TYPE: PRT
<213> ORGANISM: Homo sapiens

<400> SEQUENCE: 86

Asn Phe Pro Pro Ser Gln Asp Ala Ser Gly Asp Leu Tyr Thr Thr Ser
1               5                   10                  15

Ser Gln Leu Thr Leu Pro Ala Thr Gln Cys Pro Asp Gly Lys
            20                  25                  30

<210> SEQ ID NO 87
<211> LENGTH: 30
<212> TYPE: PRT
<213> ORGANISM: Homo sapiens
<220> FEATURE:
<221> NAME/KEY: misc_feature
<222> LOCATION: (30)..(30)
<223> OTHER INFORMATION: labeled with stable isotope

<400> SEQUENCE: 87

Asn Phe Pro Pro Ser Gln Asp Ala Ser Gly Asp Leu Tyr Thr Thr Ser
1               5                   10                  15

Ser Gln Leu Thr Leu Pro Ala Thr Gln Cys Pro Asp Gly Lys
            20                  25                  30

<210> SEQ ID NO 88
<211> LENGTH: 15
<212> TYPE: PRT
<213> ORGANISM: Homo sapiens

<400> SEQUENCE: 88

Asp Ala Ser Gly Ala Thr Phe Thr Trp Thr Pro Ser Ser Gly Lys
1               5                   10                  15

<210> SEQ ID NO 89
<211> LENGTH: 15
<212> TYPE: PRT
<213> ORGANISM: Homo sapiens
<220> FEATURE:
<221> NAME/KEY: misc_feature
<222> LOCATION: (15)..(15)
<223> OTHER INFORMATION: labeled with stable isotope
```

<400> SEQUENCE: 89

Asp Ala Ser Gly Ala Thr Phe Thr Trp Thr Pro Ser Ser Gly Lys
1               5                   10                  15

<210> SEQ ID NO 90
<211> LENGTH: 12
<212> TYPE: PRT
<213> ORGANISM: Homo sapiens

<400> SEQUENCE: 90

Ser Ser Glu Asp Pro Asn Glu Asp Ile Val Glu Arg
1               5                   10

<210> SEQ ID NO 91
<211> LENGTH: 12
<212> TYPE: PRT
<213> ORGANISM: Homo sapiens
<220> FEATURE:
<221> NAME/KEY: misc_feature
<222> LOCATION: (12)..(12)
<223> OTHER INFORMATION: labeled with stable isotope

<400> SEQUENCE: 91

Ser Ser Glu Asp Pro Asn Glu Asp Ile Val Glu Arg
1               5                   10

<210> SEQ ID NO 92
<211> LENGTH: 15
<212> TYPE: PRT
<213> ORGANISM: Homo sapiens

<400> SEQUENCE: 92

Cys Tyr Thr Ala Val Val Pro Leu Val Tyr Gly Gly Glu Thr Lys
1               5                   10                  15

<210> SEQ ID NO 93
<211> LENGTH: 15
<212> TYPE: PRT
<213> ORGANISM: Homo sapiens
<220> FEATURE:
<221> NAME/KEY: misc_feature
<222> LOCATION: (15)..(15)
<223> OTHER INFORMATION: labeled with stable isotope

<400> SEQUENCE: 93

Cys Tyr Thr Ala Val Val Pro Leu Val Tyr Gly Gly Glu Thr Lys
1               5                   10                  15

<210> SEQ ID NO 94
<211> LENGTH: 8
<212> TYPE: PRT
<213> ORGANISM: Homo sapiens

<400> SEQUENCE: 94

Val Tyr Thr Val Asp Leu Gly Arg
1               5

<210> SEQ ID NO 95
<211> LENGTH: 8
<212> TYPE: PRT
<213> ORGANISM: Homo sapiens
<220> FEATURE:
<221> NAME/KEY: misc_feature
<222> LOCATION: (8)..(8)
<223> OTHER INFORMATION: labeled with stable isotope

```
<400> SEQUENCE: 95

Val Tyr Thr Val Asp Leu Gly Arg
1               5

<210> SEQ ID NO 96
<211> LENGTH: 18
<212> TYPE: PRT
<213> ORGANISM: Homo sapiens

<400> SEQUENCE: 96

Gly Ser Val Thr Phe His Cys Ala Leu Gly Pro Glu Val Ala Asn Val
1               5                   10                  15

Ala Lys

<210> SEQ ID NO 97
<211> LENGTH: 18
<212> TYPE: PRT
<213> ORGANISM: Homo sapiens
<220> FEATURE:
<221> NAME/KEY: misc_feature
<222> LOCATION: (18)..(18)
<223> OTHER INFORMATION: labeled with stable isotope

<400> SEQUENCE: 97

Gly Ser Val Thr Phe His Cys Ala Leu Gly Pro Glu Val Ala Asn Val
1               5                   10                  15

Ala Lys

<210> SEQ ID NO 98
<211> LENGTH: 1540
<212> TYPE: PRT
<213> ORGANISM: Homo sapiens
<220> FEATURE:
<221> NAME/KEY: misc_feature
<223> OTHER INFORMATION: p180

<400> SEQUENCE: 98

Met Asp Ile Tyr Asp Thr Gln Thr Leu Gly Val Val Phe Gly Gly
1               5                   10                  15

Phe Met Val Val Ser Ala Ile Gly Ile Phe Leu Val Ser Thr Phe Ser
                20                  25                  30

Met Lys Glu Thr Ser Tyr Glu Glu Ala Leu Ala Asn Gln Arg Lys Glu
            35                  40                  45

Met Ala Lys Thr His His Gln Lys Val Glu Lys Lys Lys Glu Lys
        50                  55                  60

Thr Val Glu Lys Lys Gly Lys Thr Lys Lys Glu Glu Lys Pro Asn
65                  70                  75                  80

Gly Lys Ile Pro Asp His Asp Pro Ala Pro Asn Val Thr Val Leu Leu
                85                  90                  95

Arg Glu Pro Val Arg Ala Pro Ala Val Ala Val Ala Pro Thr Pro Val
                100                 105                 110

Gln Pro Pro Ile Ile Val Ala Pro Val Ala Thr Val Pro Ala Met Pro
            115                 120                 125

Gln Glu Lys Leu Ala Ser Ser Pro Lys Asp Lys Lys Lys Glu Lys
        130                 135                 140

Lys Val Ala Lys Val Glu Pro Ala Val Ser Ser Val Val Asn Ser Ile
145                 150                 155                 160

Gln Val Leu Thr Ser Lys Ala Ala Ile Leu Glu Thr Ala Pro Lys Glu
                165                 170                 175
```

```
Val Pro Met Val Val Pro Pro Val Gly Ala Lys Gly Asn Thr Pro
            180                 185                 190

Ala Thr Gly Thr Thr Gln Gly Lys Lys Ala Glu Gly Thr Gln Asn Gln
        195                 200                 205

Ser Lys Lys Ala Glu Gly Ala Pro Asn Gln Gly Arg Lys Ala Glu Gly
    210                 215                 220

Thr Pro Asn Gln Gly Lys Lys Thr Glu Gly Thr Pro Asn Gln Gly Lys
225                 230                 235                 240

Lys Ala Glu Gly Thr Pro Asn Gln Gly Lys Ala Glu Gly Thr Pro
                245                 250                 255

Asn Gln Gly Lys Lys Ala Glu Gly Ala Gln Asn Gln Gly Lys Lys Val
            260                 265                 270

Asp Thr Thr Pro Asn Gln Gly Lys Lys Val Glu Gly Ala Pro Thr Gln
        275                 280                 285

Gly Arg Lys Ala Glu Gly Ala Gln Asn Gln Ala Lys Lys Val Glu Gly
        290                 295                 300

Ala Gln Asn Gln Gly Lys Lys Ala Glu Gly Ala Gln Asn Gln Gly Lys
305                 310                 315                 320

Lys Gly Glu Gly Ala Gln Asn Gln Gly Lys Lys Ala Glu Gly Ala Gln
            325                 330                 335

Asn Gln Gly Lys Lys Ala Glu Gly Ala Gln Asn Gln Gly Lys Lys Ala
            340                 345                 350

Glu Gly Ala Gln Asn Gln Gly Lys Lys Ala Glu Gly Ala Gln Asn Gln
        355                 360                 365

Gly Lys Lys Ala Glu Gly Ala Gln Asn Gln Gly Lys Lys Ala Glu Gly
    370                 375                 380

Ala Gln Asn Gln Gly Lys Lys Val Glu Gly Ala Gln Asn Gln Gly Lys
385                 390                 395                 400

Lys Ala Glu Gly Ala Gln Asn Gln Gly Lys Lys Ala Glu Gly Ala Gln
            405                 410                 415

Asn Gln Gly Lys Lys Ala Glu Gly Ala Gln Asn Gln Gly Lys Lys Ala
            420                 425                 430

Glu Gly Ala Gln Asn Gly Lys Lys Ala Glu Gly Ala Gln Asn Gln
        435                 440                 445

Asp Lys Lys Ala Glu Gly Ala Gln Asn Gln Gly Arg Lys Ala Glu Gly
    450                 455                 460

Ala Gln Asn Gln Gly Arg Lys Ala Glu Gly Ala Gln Asn Gln Gly Lys
465                 470                 475                 480

Lys Ala Glu Gly Ala Gln Asn Gln Gly Lys Lys Ala Glu Gly Thr Pro
            485                 490                 495

Asn Gln Gly Lys Lys Ala Glu Gly Thr Pro Asn Gln Gly Lys Lys Ala
        500                 505                 510

Glu Gly Ala Gln Asn Gly Lys Lys Ala Glu Gly Ala Gln Asn
    515                 520                 525

Gly Lys Lys Ala Glu Gly Thr Pro Asn Gln Gly Lys Lys Ala Glu Gly
    530                 535                 540

Ala Gln Asn Gln Gly Lys Lys Ala Glu Gly Ala Gln Asn Gln Gly Lys
545                 550                 555                 560

Lys Ala Glu Gly Ala Gln Asn Gln Gly Lys Lys Ala Glu Gly Ala Gln
            565                 570                 575

Asn Gln Gly Lys Lys Ala Glu Gly Ala Gln Asn Gln Gly Lys Lys Ala
            580                 585                 590

Glu Gly Ala Gln Asn Gln Gly Lys Lys Val Glu Gly Ala Gln Asn Gln
```

```
                        595                 600                 605
    Gly Lys Lys Ala Glu Gly Ala Gln Asn Gln Gly Lys Lys Ala Glu Gly
                    610                 615                 620

Ala Gln Asn Gln Gly Lys Lys Ala Glu Gly Ala Gln Asn Gln Gly Gln
    625                 630                 635                 640

Lys Gly Glu Gly Ala Gln Asn Gln Gly Lys Lys Thr Glu Gly Ala Gln
                    645                 650                 655

Gly Lys Lys Ala Glu Arg Ser Pro Asn Gln Gly Lys Lys Gly Glu Gly
                    660                 665                 670

Ala Pro Ile Gln Gly Lys Lys Ala Asp Ser Val Ala Asn Gln Gly Thr
                    675                 680                 685

Lys Val Glu Gly Ile Thr Asn Gln Gly Lys Lys Ala Glu Gly Ser Pro
                690                 695                 700

Ser Glu Gly Lys Lys Ala Glu Gly Ser Pro Asn Gln Gly Lys Lys Ala
    705                 710                 715                 720

Asp Ala Ala Asn Gln Gly Lys Lys Thr Glu Ser Ala Ser Val Gln
                    725                 730                 735

Gly Arg Asn Thr Asp Val Ala Gln Ser Pro Glu Ala Pro Lys Gln Glu
                    740                 745                 750

Ala Pro Ala Lys Lys Ser Gly Ser Lys Lys Gly Glu Pro Gly
                    755                 760                 765

Pro Pro Asp Ala Asp Gly Pro Leu Tyr Leu Pro Tyr Lys Thr Leu Val
    770                 775                 780

Ser Thr Val Gly Ser Met Val Phe Asn Glu Gly Glu Ala Gln Arg Leu
    785                 790                 795                 800

Ile Glu Ile Leu Ser Glu Lys Ala Gly Ile Ile Gln Asp Thr Trp His
                    805                 810                 815

Lys Ala Thr Gln Lys Gly Asp Pro Val Ala Ile Leu Lys Arg Gln Leu
                    820                 825                 830

Glu Glu Lys Glu Lys Leu Leu Ala Thr Glu Gln Glu Asp Ala Ala Val
                    835                 840                 845

Ala Lys Ser Lys Leu Arg Glu Leu Asn Lys Glu Met Ala Ala Glu Lys
    850                 855                 860

Ala Lys Ala Ala Ala Gly Glu Ala Lys Val Lys Lys Gln Leu Val Ala
    865                 870                 875                 880

Arg Glu Gln Glu Ile Thr Ala Val Gln Ala Arg Met Gln Ala Ser Tyr
                    885                 890                 895

Arg Glu His Val Lys Glu Val Gln Gln Leu Gln Gly Lys Ile Arg Thr
                    900                 905                 910

Leu Gln Glu Gln Leu Glu Asn Gly Pro Asn Thr Gln Leu Ala Arg Leu
                    915                 920                 925

Gln Gln Glu Asn Ser Ile Leu Arg Asp Ala Leu Asn Gln Ala Thr Ser
                    930                 935                 940

Gln Val Glu Ser Lys Gln Asn Ala Glu Leu Ala Lys Leu Arg Gln Glu
    945                 950                 955                 960

Leu Ser Lys Val Ser Lys Glu Leu Val Glu Lys Ser Glu Ala Val Arg
                    965                 970                 975

Gln Asp Glu Gln Gln Arg Lys Ala Leu Glu Ala Lys Ala Ala Phe
                    980                 985                 990

Glu Lys Gln Val Leu Gln Leu Gln Ala Ser His Arg Glu Ser Glu Glu
                995                 1000                1005

Ala Leu Gln Lys Arg Leu Asp Glu Val Ser Arg Glu Leu Cys His
                1010                1015                1020
```

```
Thr Gln Ser Ser His Ala Ser Leu Arg Ala Asp Ala Glu Lys Ala
    1025            1030                1035

Gln Glu Gln Gln Gln Gln Met Ala Glu Leu His Ser Lys Leu Gln
    1040            1045                1050

Ser Ser Glu Ala Glu Val Arg Ser Lys Cys Glu Glu Leu Ser Gly
    1055            1060                1065

Leu His Gly Gln Leu Gln Glu Ala Arg Ala Glu Asn Ser Gln Leu
    1070            1075                1080

Thr Glu Arg Ile Arg Ser Ile Glu Ala Leu Leu Glu Ala Gly Gln
    1085            1090                1095

Ala Arg Asp Ala Gln Asp Val Gln Ala Ser Gln Ala Glu Ala Asp
    1100            1105                1110

Gln Gln Gln Thr Arg Leu Lys Glu Leu Glu Ser Gln Val Ser Gly
    1115            1120                1125

Leu Glu Lys Glu Ala Ile Glu Leu Arg Glu Ala Val Glu Gln Gln
    1130            1135                1140

Lys Val Lys Asn Asn Asp Leu Arg Glu Lys Asn Trp Lys Ala Met
    1145            1150                1155

Glu Ala Leu Ala Thr Ala Glu Gln Ala Cys Lys Glu Lys Leu His
    1160            1165                1170

Ser Leu Thr Gln Ala Lys Glu Glu Ser Glu Lys Gln Leu Cys Leu
    1175            1180                1185

Ile Glu Ala Gln Thr Met Glu Ala Leu Leu Ala Leu Leu Pro Glu
    1190            1195                1200

Leu Ser Val Leu Ala Gln Gln Asn Tyr Thr Glu Trp Leu Gln Asp
    1205            1210                1215

Leu Lys Glu Lys Gly Pro Thr Leu Leu Lys His Pro Pro Ala Pro
    1220            1225                1230

Ala Glu Pro Ser Ser Asp Leu Ala Ser Lys Leu Arg Glu Ala Glu
    1235            1240                1245

Glu Thr Gln Ser Thr Leu Gln Ala Glu Cys Asp Gln Tyr Arg Ser
    1250            1255                1260

Ile Leu Ala Glu Thr Glu Gly Met Leu Arg Asp Leu Gln Lys Ser
    1265            1270                1275

Val Glu Glu Glu Gln Val Trp Arg Ala Lys Val Gly Ala Ala
    1280            1285                1290

Glu Glu Glu Leu Gln Lys Ser Arg Val Thr Val Lys His Leu Glu
    1295            1300                1305

Glu Ile Val Glu Lys Leu Lys Gly Glu Leu Glu Ser Ser Asp Gln
    1310            1315                1320

Val Arg Glu His Thr Ser His Leu Glu Ala Glu Leu Glu Lys His
    1325            1330                1335

Met Ala Ala Ala Ser Ala Glu Cys Gln Asn Tyr Ala Lys Glu Val
    1340            1345                1350

Ala Gly Leu Arg Gln Leu Leu Leu Glu Ser Gln Ser Gln Leu Asp
    1355            1360                1365

Ala Ala Lys Ser Glu Ala Gln Lys Gln Ser Asp Glu Leu Ala Leu
    1370            1375                1380

Val Arg Gln Gln Leu Ser Glu Met Lys Ser His Val Glu Asp Gly
    1385            1390                1395

Asp Ile Ala Gly Ala Pro Ala Ser Ser Pro Glu Ala Pro Pro Ala
    1400            1405                1410
```

| | | | | | | | | | | |
|---|---|---|---|---|---|---|---|---|---|---|
| Glu | Gln | Asp | Pro | Val | Gln | Leu | Lys | Thr | Gln | Leu | Glu | Trp | Thr | Glu |
| | 1415 | | | | 1420 | | | | 1425 | |
| Ala | Ile | Leu | Glu | Asp | Glu | Gln | Thr | Gln | Arg | Gln | Lys | Leu | Thr | Ala |
| 1430 | | | | | 1435 | | | | | 1440 |
| Glu | Phe | Glu | Glu | Ala | Gln | Thr | Ser | Ala | Cys | Arg | Leu | Gln | Glu | Glu |
| 1445 | | | | | 1450 | | | | | 1455 |
| Leu | Glu | Lys | Leu | Arg | Thr | Ala | Gly | Pro | Leu | Glu | Ser | Ser | Glu | Thr |
| 1460 | | | | | 1465 | | | | | 1470 |
| Glu | Glu | Ala | Ser | Gln | Leu | Lys | Glu | Arg | Leu | Glu | Lys | Glu | Lys | Lys |
| 1475 | | | | | 1480 | | | | | 1485 |
| Leu | Thr | Ser | Asp | Leu | Gly | Arg | Ala | Ala | Thr | Arg | Leu | Gln | Glu | Leu |
| 1490 | | | | | 1495 | | | | | 1500 |
| Leu | Lys | Thr | Thr | Gln | Glu | Gln | Leu | Ala | Arg | Glu | Lys | Asp | Thr | Val |
| 1505 | | | | | 1510 | | | | | 1515 |
| Lys | Lys | Leu | Gln | Glu | Gln | Leu | Glu | Lys | Ala | Glu | Asp | Gly | Ser | Ser |
| 1520 | | | | | 1525 | | | | | 1530 |
| Ser | Lys | Glu | Gly | Thr | Ser | Val |
| 1535 | | | | | 1540 |

```
<210> SEQ ID NO 99
<211> LENGTH: 4623
<212> TYPE: DNA
<213> ORGANISM: Homo sapiens
<220> FEATURE:
<221> NAME/KEY: misc_feature
<223> OTHER INFORMATION: p180

<400> SEQUENCE: 99
atggatattt acgacactca aaccttgggg gttgtggtct ttggaggatt catggttgtt    60
tctgccattg gcatcttcct ggtgtcgact ttctccatga aggaaacgtc atatgaagaa   120
gccctagcca accagcgcaa ggagatggcg aaaactcacc accagaaagt cgagaagaaa   180
aagaaggaga aaacagtgga gaagaaggaa agaccaagaa aaaggaagaa gaaacctaat   240
gggaagatac ctgatcatga tccagccccc aatgtgactg tcctccttcg agaaccagtg   300
cgggctcctg ctgtggctgt ggctccaacc ccagtgcagc ccccattat cgttgctcct   360
gtcgccacag ttccagccat gccccaggag aagctggcct cctcccccaa ggacaaaaag   420
aagaaggaga aaaagtggc aaaagtggaa ccagctgtca gctctgtagt gaattccatc   480
caggttctca cttcgaaggc tgccatcttg gaaactgctc caaggaggt gccgatggtg   540
gtggtgcccc cagtgggtgc caagggcaac acaccagcca ctggcactac tcagggcaaa   600
aaggcggagg ggactcagaa tcaaagcaaa aaggctgaag gagccccaaa ccagggcaga   660
aaggcagagg gaaccccaaa ccagggcaaa agacagagg gaaccccaaa ccaagggaaa   720
aaggcagagg gaacccaaa ccaaggcaaa aaggcagaag gaaccccaaa ccaaggcaaa   780
aaggcggagg gggcccagaa ccaggtaaa aaggtagata aaccccaaa ccaggggaaa   840
aaggtggagg gggccccaac ccagggcaga aaggccgagg ggctcagaa ccaggccaaa   900
aaggtagaag gggcccagaa caagggcaaa aaggcagagg gggcccagaa tcaggggcaaa   960
aagggagagg gggcccagaa ccagggcaag aaggccgagg gggcccagaa tcagggcaag  1020
aaggccgagg gggcccagaa tcagggcaag aaggccgagg gggcccagaa tcagggcaag  1080
aaggccgagg gggcccagaa tcagggcaag aaggctgagg gggctcagaa ccaggggcaaa  1140
aaggccgagg gggctcagaa ccaggggcaaa aagtagaag gggcccagaa ccaggggcaag  1200
aaggctgagg gtgcccagaa ccagggcaaa aaggccgagg gggcccagaa tcagggcaaa  1260
```

```
aaggccgagg gggcccagaa ccagggcaag aaggcagagg gggcccagaa ccagggcaag    1320
aaggccgagg gggcccagaa ccaggacaag aaggccgagg gggcccagaa ccagggcagg    1380
aaggccgagg gggcccagaa ccagggcagg aaggccgagg gggcccagaa ccagggcaag    1440
aaggccgagg gggcccagaa ccagggcaag aaggccgagg ggaccccgaa ccagggcaag    1500
aaggccgagg ggaccccgaa ccagggcaag aaggccgagg gggcccagaa ccagggcaag    1560
aaggccgagg gggcccagaa ccagggcaag aaggccgagg ggaccccgaa ccagggcaag    1620
aaggccgagg gggcccagaa ccagggcaag aaggccgagg gggcccagaa ccagggcaag    1680
aaggccgagg gggcccagaa ccagggcaag aaggccgagg gggcccagaa ccagggcaag    1740
aaggccgagg gggcccagaa ccagggcaag aaggccgagg gtgctcagaa ccagggcaaa    1800
aaagtagaag gggcccagaa ccagggcaag aaggctgagg gggcccagaa ccagggcaag    1860
aaggccgagg gggctcagaa ccagggcaaa aaggccgagg gagcccagaa ccagggccaa    1920
aaaggagagg gagcccagaa tcagggtaaa aagacagaag gggctcaggg caaaaaggca    1980
gaaaggagtc ccaaccaagg caaaaaggga gagggagctc ccatccaggg caaaaaggca    2040
gattcggttg ctaatcaggg cacaaaggta gagggtatta caaaccaggg gaaaaaagca    2100
gaagggtccc ccagtgaagg caaaaaggca gaagggtccc ccaaccaagg caaaaaggca    2160
gacgcagctg ccaatcaggg taaaaagaca gagtcagctt ctgtccaggg cagaaataca    2220
gatgtggccc agagcccaga ggcaccaaag caagaggctc ctgccaagaa gaagtctggt    2280
tcaaagaaaa aaggtgagcc tgggccccca gatgccgacg ccctctcta cctcccctac     2340 aagacgctgg tctccacggt tgggagcatg gtgttcaacg agggcgaggc ccagcggctc    2400
atcgagatcc tgtccgagaa ggctggcatc attcaggaca cctggcacaa ggccactcag    2460
aagggtgacc ctgtggcgat tctgaaacgc agctggaag agaaggaaaa actgctggcc     2520
acagaacagg aagatgcggc tgtcgccaag agcaaactga gggagctcaa caaggagatg    2580
gcagcagaaa aggccaaagc agcagccggg gaggccaaag tgaaaaagca gctggtggcc    2640
cgggagcagg agatcacggc tgtgcaggca cgcatgcagg ccagctaccg ggagcacgtg    2700
aaggaggtgc agcagctgca gggcaagatc cggactcttc aggagcagct ggagaatggc    2760
cccaacacgc agctggcccg cctgcagcag gagaactcca tcctgcggga tgccttgaac    2820
caggccacga gccaggtgga gagcaagcag aacgcagagc tggccaagct tcggcaggag    2880
ctcagcaagg tcagcaaaga gctggtggag aagtcagagg ctgtgcggca agatgagcag    2940
cagcggaaag ctctggaagc caaggcagct gccttcgaga agcaggtcct gcagctgcag    3000
gcgtcccaca gggagagtga ggaggccctg cagaagcgcc tggacgaggt cagccgggag    3060
ctgtgccaca cgcagagcag ccacgccagc ctccgggcgg atgccgagaa ggcccaggag    3120
caacagcagc agatggccga gctgcacagc aagttacagt cctccgaggc agaggtgcgc    3180
agcaaatgcg aggagctgag tggcctccac gggcagctcc aggaggccag gcggagaac    3240 tcccagctca cagagagaat ccgttccatt gaggccctgc tggaggcggg ccaggcgcgg    3300
gatgcccagg acgtccaggc cagccaggcg gaggctgacc agcagcagac tcgcctcaag    3360
gagctggagt cccaggtgtc gggtctggag aaggaggcca tcgagctcag ggaggccgtc    3420
gagcagcaga aagtgaagaa caatgacctc cgggagaaga actggaaggc catggaggca    3480
ctggccacgg ccgagcaggc ctgcaaggag aagctgcact ccctgacccca ggccaaggag    3540 gaatcggaga agcagctctg tctgattgag gcgcagacca tggaggccct gctggctctg    3600
```

-continued

```
ctcccagaac tctctgtctt ggcacaacag aattacaccg agtggctgca ggatctcaaa    3660
gagaaaggcc ccacgctgct gaagcacccg ccagctcccg cggagccttc ctcggacctg    3720
gcctccaagt tgagggaggc cgaggagacg cagagcacac tgcaggccga gtgtgaccag    3780
taccgcagca tcctggcgga gacggagggc atgctcagag acctgcagaa gagcgtggag    3840
gaggaggagc aggtgtggag ggccaaggtg ggcgccgcag aggaggagct ccagaagtcc    3900
cgggtcacag tgaagcatct cgaagagatt gtagagaagc taaaaggaga acttgaaagt    3960
tcggaccagg tgagggagca cacgtcgcat ttggaggcag agctggaaaa gcacatggcg    4020
gccgccagcg ccgagtgcca gaactacgcc aaggaggtgg cagggctgag gcaacttctc    4080
ctagaatctc aatctcagct cgatgccgcc aagagcgaag cccagaaaca gagcgatgag    4140
cttgccctgg tcaggcagca gttgagtgaa atgaagagcc acgtagagga tggtgacatt    4200 gctgggccc cagcttcctc cccagaggcg cccccagccg agcaggaccc cgttcagctg    4260
aagacgcagc tggagtggac agaagccatc ctggaggatg agcagacaca gcggcagaag    4320
ctcacggccg agtttgagga ggctcagacc tcggcatgtc ggttacaaga agaattggag    4380
aagctccgca cagccggccc cctagagtct tcagaaacag aggaggcctc acagctgaag    4440
gagagactag aaaaagagaa gaagttaaca agtgacctgg ggcgcgccgc cacgagactg    4500
caggagcttc tgaagacgac ccaggagcag ctggcaaggg agaaggacac ggtgaagaag    4560
ctgcaggaac agctggaaaa ggcagaggac ggcagcagct caaaggaggg cacctctgtc    4620
tga                                                                   4623
```

<210> SEQ ID NO 100
<211> LENGTH: 424
<212> TYPE: PRT
<213> ORGANISM: Homo sapiens
<220> FEATURE:
<221> NAME/KEY: misc_feature
<223> OTHER INFORMATION: SF3B4

<400> SEQUENCE: 100

```
Met Ala Ala Gly Pro Ile Ser Glu Arg Asn Gln Asp Ala Thr Val Tyr
1               5                   10                  15

Val Gly Gly Leu Asp Glu Lys Val Ser Glu Pro Leu Leu Trp Glu Leu
            20                  25                  30

Phe Leu Gln Ala Gly Pro Val Val Asn Thr His Met Pro Lys Asp Arg
        35                  40                  45

Val Thr Gly Gln His Gln Gly Tyr Gly Phe Val Glu Phe Leu Ser Glu
    50                  55                  60

Glu Asp Ala Asp Tyr Ala Ile Lys Ile Met Asn Met Ile Lys Leu Tyr
65                  70                  75                  80

Gly Lys Pro Ile Arg Val Asn Lys Ala Ser Ala His Asn Lys Asn Leu
                85                  90                  95

Asp Val Gly Ala Asn Ile Phe Ile Gly Asn Leu Asp Pro Glu Ile Asp
            100                 105                 110

Glu Lys Leu Leu Tyr Asp Thr Phe Ser Ala Phe Gly Val Ile Leu Gln
        115                 120                 125

Thr Pro Lys Ile Met Arg Asp Pro Asp Thr Gly Asn Ser Lys Gly Tyr
    130                 135                 140

Ala Phe Ile Asn Phe Ala Ser Phe Asp Ala Ser Asp Ala Ala Ile Glu
145                 150                 155                 160

Ala Met Asn Gly Gln Tyr Leu Cys Asn Arg Pro Ile Thr Val Ser Tyr
                165                 170                 175
```

```
Ala Phe Lys Lys Asp Ser Lys Gly Glu Arg His Gly Ser Ala Ala Glu
            180                 185                 190

Arg Leu Leu Ala Ala Gln Asn Pro Leu Ser Gln Ala Asp Arg Pro His
        195                 200                 205

Gln Leu Phe Ala Asp Ala Pro Pro Pro Ser Ala Pro Asn Pro Val
    210                 215                 220

Val Ser Ser Leu Gly Ser Gly Leu Pro Pro Gly Met Pro Pro
225                 230                 235                 240

Gly Ser Phe Pro Pro Pro Val Pro Pro Gly Ala Leu Pro Pro Gly
                245                 250                 255

Ile Pro Pro Ala Met Pro Pro Pro Met Pro Pro Gly Ala Ala Gly
            260                 265                 270

His Gly Pro Pro Ser Ala Gly Thr Pro Gly Ala Gly His Pro Gly His
            275                 280                 285

Gly His Ser His Pro His Pro Phe Pro Pro Gly Gly Met Pro His Pro
    290                 295                 300

Gly Met Ser Gln Met Gln Leu Ala His His Gly Pro His Gly Leu Gly
305                 310                 315                 320

His Pro His Ala Gly Pro Pro Gly Ser Gly Gln Pro Pro Arg
                325                 330                 335

Pro Pro Pro Gly Met Pro His Pro Gly Pro Pro Met Gly Met Pro
                340                 345                 350

Pro Arg Gly Pro Pro Phe Gly Ser Pro Met Gly His Pro Gly Pro Met
            355                 360                 365

Pro Pro His Gly Met Arg Gly Pro Pro Leu Met Pro Pro His Gly
            370                 375                 380

Tyr Thr Gly Pro Pro Arg Pro Pro Pro Tyr Gly Tyr Gln Arg Gly Pro
385                 390                 395                 400

Leu Pro Pro Pro Arg Pro Thr Pro Arg Pro Pro Val Pro Pro Arg Gly
                405                 410                 415

Pro Leu Arg Gly Pro Leu Pro Gln
            420

<210> SEQ ID NO 101
<211> LENGTH: 1275
<212> TYPE: DNA
<213> ORGANISM: Homo sapiens
<220> FEATURE:
<221> NAME/KEY: misc_feature
<223> OTHER INFORMATION: SF3B4

<400> SEQUENCE: 101
atggctgccg ggccgatctc cgagcggaat caggatgcca ctgtgtacgt ggggggcctg    60
gatgagaagg ttagtgaacc gctgctgtgg gaactgtttc tccaggctgg accagtagtc   120
aacacccaca tgccaaagga tagagtcact ggccagcacc aaggctatgg ctttgtggaa   180
ttcttgagtg aggaagatgc tgactatgcc attaagatca tgaacatgat caaactctat   240
gggaagccaa tacgggtgaa caaagcatca gctcacaaca aaaacctgga tgtaggggcc   300
aacattttca ttgggaacct ggaccctgag attgatgaga agttgcttta tgatactttc   360
agcgcctttg gggtcatctt acaaaccccc aaaattatgc gggaccctga cacaggcaac   420
tccaaaggtt atgcctttat taattttgct tcatttgatg cttcggatgc agcaattgaa   480
gccatgaatg gcagtaccct ctgtaaccgt cctatcaccg tatcttatgc cttcaagaag   540
gactccaagg gtgagcgcca tggctcagca gccgaacgac ttctggcagc tcagaacccg   600
```

-continued

```
ctctcccagg ctgatcgccc tcatcagctg tttgcagatg cacctcctcc accctctgct      660
cccaatcctg tggtatcatc attggggtct gggcttcctc caccaggcat gcctcctcct      720
ggctccttcc caccccagt gccacctcct ggagccctcc cacctgggat accccagcc       780 atgcccccac cacctatgcc tcctggggct gcaggacatg gcccccatc ggcaggaacc      840 ccaggggcag gacatcctgg tcatggacac tcacatcctc acccattccc accgggtggg    900
atgccccatc cagggatgtc tcagatgcag cttgcacacc atggccctca tggcttagga    960 catcccacg ctggaccccc aggctctggg ggccagccac cgccccgacc accacctgga     1020
atgcctcatc ctggacctcc tccaatgggc atgcccccc gagggcctcc attcggatct     1080
cccatgggtc acccaggtcc tatgcctccg catggtatgc gtggacctcc tccactgatg    1140 ccccccatg gatacactgg ccctccacga ccccacct atggctacca gcggggcct        1200 ctccctccac ccagacccac tccccggcca ccagttcccc ctcgaggccc acttcgaggc    1260
cctctccctc agtaa                                                     1275
```